(12) United States Patent
Darwish et al.

(10) Patent No.: US 11,860,156 B2
(45) Date of Patent: Jan. 2, 2024

(54) BIOANALYTICAL ANALYSIS OF SITE-SPECIFIC ANTIBODY DRUG CONJUGATES

(71) Applicant: Genentech, Inc., South San Francisco, CA (US)

(72) Inventors: Martine Darwish, San Francisco, CA (US); Surinder Kaur, Lafayette, CA (US); Dian Su, Redwood City, CA (US); Keyang Xu, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 519 days.

(21) Appl. No.: 16/883,152

(22) Filed: May 26, 2020

(65) Prior Publication Data

US 2021/0011000 A1    Jan. 14, 2021

Related U.S. Application Data

(63) Continuation of application No. 15/606,304, filed on May 26, 2017, now abandoned.

(60) Provisional application No. 62/342,825, filed on May 27, 2016.

(51) Int. Cl.
| | |
|---|---|
| *G01N 33/50* | (2006.01) |
| *G01N 33/68* | (2006.01) |
| *C12Q 1/37* | (2006.01) |
| *A61K 38/02* | (2006.01) |
| *A61K 39/395* | (2006.01) |
| *G01N 33/53* | (2006.01) |
| *C07K 14/00* | (2006.01) |

(52) U.S. Cl.
CPC ......... *G01N 33/5005* (2013.01); *A61K 38/02* (2013.01); *A61K 39/395* (2013.01); *C12Q 1/37* (2013.01); *G01N 33/53* (2013.01); *G01N 33/6848* (2013.01); *G01N 33/6857* (2013.01); *C07K 14/00* (2013.01)

(58) Field of Classification Search
CPC ...... A61K 38/02; A61K 39/395; C07K 14/00; C12Q 1/37; G01N 33/5005; G01N 33/53; G01N 33/6848; G01N 33/6857
See application file for complete search history.

(56) References Cited

U.S. PATENT DOCUMENTS

| | | |
|---|---|---|
| 7,521,541 B2 | 4/2009 | Eigenbrot et al. |
| 7,666,582 B2 | 2/2010 | Pawel-Rammingen et al. |
| 7,723,485 B2 | 5/2010 | Junutula et al. |
| 8,541,178 B2 | 9/2013 | Kaur et al. |
| 8,679,767 B2 | 3/2014 | Kaur et al. |
| 2009/0286258 A1 | 11/2009 | Kaur et al. |
| 2010/0015652 A1 | 1/2010 | Granda et al. |
| 2012/0315645 A1 | 12/2012 | Kaur et al. |
| 2015/0316515 A1 | 11/2015 | Lauber et al. |
| 2017/0315132 A1 | 11/2017 | Kaur et al. |
| 2017/0370906 A1 | 12/2017 | Darwish et al. |
| 2021/0123928 A1* | 4/2021 | Kaur .................. G01N 33/6848 |

FOREIGN PATENT DOCUMENTS

| | | |
|---|---|---|
| EP | 1740954 B1 | 8/2015 |
| WO | 2005101017 A1 | 10/2005 |
| WO | 2009080278 A1 | 7/2009 |
| WO | 2010002911 A2 | 1/2010 |
| WO | 2011042027 A2 | 4/2011 |
| WO | 2012155019 A1 | 11/2012 |
| WO | 2015040125 A1 | 3/2015 |

OTHER PUBLICATIONS

Johansson et al., "IdeS: a bacterial proteolytic enzyme with therapeutic potential," PLOS One, 2008, vol. 3, issue 2, e1692, pp. 1-6.*
Anderson, L, et al., "Quantitative mass spectrometric multiple reaction monitoring assays for major plasma proteins", Molecular & Cellular Proteomics 5, 573-588 (2006).
Boushaba, R, et al., "Kinetics of whole serum and prepurified IgG digestion by pepsin for F(ab')2 manufacture", Biotechnol Prog 19, 1176-1182 (2003).
Carr, S, et al., "Protein quantitation through targeted mass spectrometry: the way out of biomarker purgatory?", Clinical Chemistry 54(11), 1749-1752 (2008).
Chen, T, et al., "Chemical de-conjugation for investigating the stability of small molecule drugs in antibody-drug conjugates", Journal of Pharmaceutical and Biomedical Analysis 117, 304-310 (2016).
Chen, J, et al., "Development of a Native Nanoelectrospray Mass Spectrometry Method for Determination of the Drug-to-Antibody Ratio of Antibody-Drug Conjugates", Anal Chem 85(3), 1699-1704 (2013).
Dere, R, et al., "PK assays for antibody-drug conjugates: case study with ado-trastuzumab emtansine", Bioanalysis 5 (9), 1025-1040 (2013).
Farias, S, et al., "Mass Spectrometric Characterization of Transglutaminase Based Site-Specific Antibody-Drug Conjugates", Bioconjugate Chem 25(2), 240-250 (2014).
Gong, C, et al., "Post-pellet-digestion precipitation and solid phase extraction: A practical and efficient workflow to extract surrogate peptides for ultra-high performance liquid chromatography—tandem mass spectrometry bioanalysis of a therapeutic antibody in the low n", Journal of Chromatography 1424, 27-36 (2015).
Hagman, C, et al., "Absolute quantification of monoclonal antibodies in biofluids by liquid chromatography-tandem mass spectrometry", Anal Chem 80, 1290-1296 (2008).
He, J, et al., "High-Resolution Accurate-Mass Mass Spectrometry Enabling In-Depth Characterization of in Vivo Biotransformations for Intact Antibody-Drug Conjugates", Anal Chem 89, 5476-5483 (2017).

(Continued)

*Primary Examiner* — Galina M. Yakovleva
(74) *Attorney, Agent, or Firm* — Viksnins Harris Padys Malen LLP

(57) ABSTRACT

Methods to rapidly and accurately detect, characterize, measure, and quantify site-specific antibody drug conjugates, that may be present in pre-clinical animal biological samples, or human biological samples, including plasma/serum and tissue samples.

7 Claims, 18 Drawing Sheets

Specification includes a Sequence Listing.

(56) References Cited

OTHER PUBLICATIONS

Heudi, O, et al., "Towards absolute quantification of therapeutic monoclonal antibody in serum by LC-MS/MS using sotope-labeled antibody standard and protein cleavage isotope dilution mass spectrometry", Anal Chem 80, 4200-4207 (2008).

Janin-Bussat, M, et al., "Characterization of antibody drug conjugate positional isomers at cysteine residues by peptide mapping LC-MS analysis", Journal of Chromatography B 981-982, 9-13 (2015).

Ji, C, et al., "A universal strategy for development of a method for absolute quantification of therapeutic monoclonal antibodies in biological matrices using differential dimethyl labeling coupled with ultra performance liquid chromatography—tandem mass spectrometry", Anal Chem 81, 9321-9328 (2009).

Jones, R, et al., "A protocol for 'enhanced pepsin digestion': a step by step method for obtaining pure antibody fragments in high yield from serum", Journal of Immunological Methods 275, 239-250 (2003).

Junutula, J, et al., "Rapid identification of reactive cysteine residues for site-specific labeling of antibody-Fabs", Journal of Immunological Methods 332, 41-52 (2008).

Junutula, J, et al., "Site-specific conjugation of a cytotoxic drug to an antibody improves the therapeutic index", Nature Biotechnology 26(8), 925-932 (2008).

Kaur, S, "ADC Analyte Diversity and Appropriate PK Assays Part 1: Background & Bioanalytical Strategy", European Bioanalysis Forum—ADC Training Day, 35 pages, Jun. 20, 2017.

Kaur, S, et al., "Bioanalytical assay strategies for the development of antibody-drug conjugate biotherapeutics", Bioanalysis 5(2), 201-226 (2013).

Kleemann, G, et al., "Characterization of IgG1 Immunoglobulins and Peptide-Fc Fusion Proteins by Limited Proteolysis in Conjunction with LC-MS", Anal Chem 80, 2001-2009 (2008).

Kuhn, "Developing multiplexed assays for troponin I and interleukin-33 in plasma by peptide immunoaffinity enrichment and targeted mass spectrometry", Clinical Chemistry 55(6), 1108-1117 (2009).

Li, Y, et al., "An enzymatic deconjugation method for the analysis of small molecule active drugs on antibody-drug conjugates", MAbs 8(4), 698-705 (2016).

Liu, H, et al., "Quantitation of a recombinant monoclonal antibody in monkey serum by liquid chromatography-mass spectrometry", Analytical Biochemistry 414, 147-153 (2011).

Nassur, S, et al., "Structural characterization of antibody drug conjugate by a combination of intact, middle-up and bottom-up techniques using sheathless capillary electrophoresis—Tandem mass spectrometry as nanoESI infusion platform and separation method", Analytica Chimica Acta 918, 50-59 (2016).

Pace, C, et al., "How to measure and predict the molar absorption coefficient of a protein", Protein Sci 4, 2411-2423 (1995).

Patent Cooperation Treaty, International Searching Authority, Search Report and Written Opinion for PCT/US2017/034680, 16 pages, dated Aug. 17, 2017.

Redman, E, et al., "Characterization of Intact Antibody Drug Conjugate Variants Using Microfluidic Capillary Electrophoresis—Mass Spectrometry", Anal Chem 88(4), 2220-2226 (2016).

Su, D, et al., "Custom-Designed Affinity Capture LC-MS F(ab')2 Assay for Biotransformation Assessment of Site-Specific Antibody Drug Conjugates", Anal Chem 88(23), 11340-11346 (2016).

Thermofisher, http://assets.thermofisher.com/TFS-Assets/LSG/manuals/MAN0011972_Dephosphorylation_Proteins_UG.pdf, 1 page, on Mar. 11, 2019, created/modified on Internet May 2, 2013.

Wagner-Rousset, E, et al., "Antibody-drug conjugate model fast characterization by LC-MS following IdeS proteolytic digestion", mAbs 6(1), 173-184 (2014).

Xu, K, et al., "Characterization of intact antibody-drug conjugates from plasma/serum in vivo by affinity capture capillary liquid chromatography-mass spectrometry", Analytical Biochemistry 412, 56-66 (2011).

Xu, K, et al., "Characterization of the drug-to-antibody ratio distribution for antibody-drug conjugates in plasma/ serum", Bioanalysis 5(9), 1057-1071 (2013).

\* cited by examiner

BIOANALYTICAL ANALYSIS OF SITE-SPECIFIC ANTIBODY DRUG CONJUGATES

CROSS REFERENCE TO RELATED APPLICATIONS

This continuation application claims priority to non-provisional U.S. application Ser. No. 15/606,304, filed 26 May 2017, which claims priority to U.S. Provisional Application No. 62/342,825, filed on 27 May 2016, each of which are incorporated by reference in entirety.

SEQUENCE LISTING

The instant application contains a Sequence Listing which has been submitted in ASCII format via EFS-Web and is hereby incorporated by reference in its entirety. Said ASCII copy, created on May 12, 2017, is named P33200-US_Sequence_Listing.txt and is 817 bytes in size.

TECHNICAL FIELD

This disclosure relates to methods of capturing, detecting, analyzing, characterizing, and quantifying antibody-drug conjugates, and their fragments and metabolites, in non-biological or biological matrices by chromatography and/or mass spectrometry.

BACKGROUND

With the approval of brentuximab vedotin (ADCETRIS®, Seattle Genetics) and ado-trastuzumab emtansine (KADCYLA®, Genentech), the therapeutic potential of antibody drug conjugates (ADCs) providing targeted delivery of pharmaceutically active drug or toxin molecules to specific sites of action has been confirmed, and further research and development has resulted. ADCs are generally composed of an antibody, a pharmaceutically active small molecule drug or toxin (often referred to as the "drug moiety" or "payload"), and an optional linker to connect the two. This protein construct thus joins the small-molecule, highly potent drug to the large-molecule antibody, which is selected or engineered to target antigens on a specific cell type, typically a cancer cell. ADCs thus employ the powerful targeting ability of monoclonal antibodies to specifically deliver highly potent, conjugated small molecule therapeutics to a cancer cell. The small molecule therapeutic payload is often a highly-potent, cytotoxic molecule that would be too toxic for use in conventional chemotherapy.

As successful ADC candidates emerge from ongoing research and development programs and proceed to clinical evaluation and market approval, safety and efficacy assays that can effectively assess the complex chemical composition created by combination of a large protein complex (the antibody or antibody fragments) and a typically much smaller, but highly potent, drug molecule, are needed. The characterization of the drug-antibody linkage, antibody and drug concentrations, as well as the drug-to-antibody ratio, and stability of these ADC compositions must be initially established, and then monitored for consistency, as these properties of the ADC can affect the bioactivity, pharmacokinetics, distribution, immunogenicity, safety, and stability profiles of these therapeutic entities. These challenges in ADC characterization are even more difficult when applied to heterogeneous compositions of ADC molecules, which typify many currently available ADCs that may have zero to eight drug molecules per antibody. This heterogeneity is one factor leading to inconsistent measurement of pharmacokinetic parameters and in vivo performance of these therapeutic constructs.

Liquid chromatography-tandem mass spectrometry (LC-MS/MS) is a powerful tool for protein analysis and quantitation in very complex matrices like plasma/serum/tissue samples. Since peptides resulting from the digestion of the protein of interest and other endogenous proteins may have the same or similar nominal mass, the second dimension of MS fragmentation often provides a unique fragment of a peptide of interest. The combination of the specific parent peptide and the unique fragment ion may be used to selectively monitor for the molecule to be quantified. Such approach is termed "Multiple reaction monitoring" (MRM), also referred to as Selected Reaction Monitoring (SRM), which is a commonly used mode for protein quantification. But this powerful tool may be compromised by the analysis of a complex mixture of intact ADCs, antibody fragments, and peptide-linked drug(s) as well as free drug molecules.

Recent development of next generation ADCs has been focused on exploring technologies to produce homogenous ADCs with improved stability, pharmacokinetics (PK) and therapeutic index. New types of linkers and toxins with a variety of cytotoxic mechanisms are also being explored. These next generation ADCs may pose additional bioanalytical challenges due to the structural complexity of new payloads and associated complex biotransformations in vivo. For instance, affinity capture LC-MS, has been used for drug-to-antibody ratio (DAR) and catabolite characterization of intact ADCs. The intact ADC affinity capture LC-MS assay employs PNGase F to remove N-glycans in the Fc region and thus reduce the complexity and heterogeneity of ADC mass spectra. However, the intact mass spectra of new ADCs are more complex and the sensitivity and resolution of the method may not be sufficient to elucidate some structural modifications and accurately characterize DAR distribution.

Affinity capture liquid chromatography-mass spectrometry (LC-MS) has been widely used for direct drug-to-antibody ratio (DAR) and catabolite characterization of antibody-drug conjugates (ADCs). However, the intact mass spectra of new ADCs, which incorporate new types of linkers and payloads other than maytansines and auristatins, are more complex than those examined previously. The current method has showed some limitations in elucidating certain structural modifications.

SUMMARY

An aspect of the invention is an analytical approach for antibody drug conjugates (ADCs), such as THIOMAB™ (Genetech, Inc.) antibody-drug conjugates (TDCs), where the linker drugs are site-specifically conjugated in the Fab region. The affinity capture LC-MS F(ab')2 assay incorporates affinity capture of ADCs via binding to the Fab region, followed by on-bead IdeS digestion to remove the Fc domain specifically and uniformly. The resulting F(ab')2 (~100 kDa) fragments contain the key ADC structural information, such as drug-to-antibody ratio and drug metabolism and are more readily analyzed by electrospray ionization LCMS than the intact ADC (~150 kDa). The reduced size of analytes results in improved mass spectral sensitivity and resolution. In addition, the reduced and optimized sample preparation time, for example, rapid removal of the Fc fragment by IdeS digestion, minimizes possible assay artifacts of drug metabolism and skewed DAR profiles that may result from the prolonged incubation times (e.g., overnight enzymatic treatment for Fc deglycosylation). The affinity capture LC-MS F(ab')2 assay provides more detailed and accurate information on ADC biotransformations in vivo, enabling analysis of low-dose, labile, and complex site-specific ADCs with linker-drug conjugated in the Fab region.

An embodiment of the invention is a method employing anti-Fc capture and IgdE protease digestion of ADCs with site-specific conjugated drug moieties in the Fc region.

Robust methods are provided to detect and quantify antibody protein concentration and antibody-conjugated drug quantity and structure characterization by digestion of the antibody and separation of the drug component of an ADC, followed by chromatographic and/or mass spectrophotometric analysis of the resulting composition of the combined released drug and peptides from the digested antibody. The methods of the invention utilize ADC fragments containing the drug moiety as surrogates for intact ADCs and therefore provide increased assay sensitivity and resolution. The new methods also minimize artifacts of drug metabolism and reduce potential biased response to certain drug-to-antibody ratio (DAR) species. Antibody and ADC analysis was previously conducted using limited proteolytic digestion by attempting to control the activity of endoproteinase Lys-C, or proteinase PNGase, followed by reverse-phase HPLC and mass spectrometry. These methods were found to be insufficient in the analysis of some next generation ADCs containing recombinantly-engineered, specific drug conjugation sites, due to limitations in sensitivity, resolution, and biased response to certain DAR species. This is particularly true of ADCs that are labile, demanding much higher MS resolution and that have site specific conjugations to highly potent DNA damaging agents, which are typically administered in low doses, and are therefore in samples at low concentrations, demanding much higher sensitivity in the analytical techniques used to characterize the ADC composition and characterize the structure of metabolites that may be present in biological samples collected after administration of the ADC to a human or other test subject.

Thus, the invention provides consistent, reliable, efficient, high-resolution and highly sensitive methods of assessing stability, post-translational and chemical modifications during production, formulation, storage, and administration during the development of site-specific ADCs by combining site specific and controlled proteolytic digestion matched with the analysis of homogenous and site specific ADC to reduce the size of the ADC analytes.

The reduced size of analytes results in improved mass spectral sensitivity, and resolution, and the response difference observed with some intact DARs are reduced. In addition, the specific proteolytic digestion eliminates the need for overnight deglycosylation of the Fc carbohydrates. Additionally, rapid proteolytic digestion minimizes assay artifacts that may result from overnight enzymatic treatments. The affinity capture LC-MS F(ab')2 assays of this disclosure provide more detailed and accurate information on ADC biotransformations in vivo, for the analysis of low-dose, labile, and complex site-specific ADCs with linker-drug conjugated in the Fab region, which may not be feasible using previous methods The invention provides methods of evaluating an ADC by digesting an ADC containing at least one drug moiety linked to an antibody at a recombinantly-engineered site with a protease that cleaves the ADC to form a digested ADC composition that includes at least one peptide fragment that is not linked to the drug moiety, and at least one peptide fragment that is linked to the drug moiety. The digested ADC composition is then analyzed by high performance liquid chromatography (HPLC) and/or mass spectrometry (MS) to detect at least one peptide fragment that is linked to the at least one drug moiety. The recombinantly-engineered specific site of attachment of the drug moiety to the ADC may be a site selected from a cysteine amino acid residue, a selenocysteine amino acid residue, a glutamine amino acid residue, a non-naturally occurring amino acid residue, and a sugar-modified glycan residue. The ADC may be an IgG antibody. The antibody portion of the ADC may be an antibody fragment. The antibody portion of the ADC may be a human or humanized antibody. The ADC may be glycosylated or phosphorylated. The antibody portion of the ADC may specifically bind to one or more tumor-associated antigens or cell-surface receptors.

The drug moiety may comprise at least one aromatic ring. Exemplary drug moieties include peptides, polyamides, maytansinoids, dolastatins, auristatins, calicheamicins, pyrrolobenzodiazepine (PBD), PNU-159682, anthracyclines, duocarmycins, vinca alkaloids, taxanes, trichothecene, CC1065, duocarmycin, camptothecin, elinafide, antibiotics, fluorophores, radioisotopes, as well as stereoisomers, isosteres, metabolites, analogs or derivatives of these compounds. The drug moiety may also be linked to the antibody portion of the ADC through a linker.

The protease utilized in these methods may be selected from an IdeS protease, an IdeZ protease, an IgdE protease, a SpeB protease, a gingipain protease, an endoglycosidase, and combinations thereof. The digestion procedure may comprise incubating the ADC with the protease at a temperature between about 20° C. and about 45° C., and typically includes incubating the ADC with the protease at a temperature of about 37° C. The digestion may also comprise incubating the ADC with the protease at a pH between about pH 5 and about pH 9, and typically includes incubating the ADC with the protease at a pH of about pH 7. The digestion may also comprise incubating the ADC with the protease for a time period between about 0.1 hour and about 48 hours, and typically includes incubating the ADC with the protease for a time period of about 1 hour.

The analyzing may include at least one of RP-LC, RP-LC/MS, and LC-MS/MS analyses.

In these methods, prior to the digesting step, the ADC may be suspended in a matrix selected from a buffer, whole blood, serum, plasma, cerebrospinal fluid, saliva, urine, lymph, bile, feces, sweat, vitreous, tears, and tissue. In example embodiments, the ADC is suspended in whole blood, serum, plasma, or tissue of a mammal selected from a human, a cynomolgus monkey, a rat, and a mouse. The ADC may therefore be enriched prior to the digesting step, by a technique selected from size exclusion chromatography, dialysis, selective precipitation, differential centrifugation, filtration, gel electrophoresis, liquid chromatography, reversed-phase phase chromatography, immunoprecipitation, SPINTRAP™ (Cytiva, Inc.) spin columns including protein A and protein G, NHS and streptavidin iron or phosphorus or immobilized antibodies or lectin, paramagnetic beads, immuno-depletion, fractionation, solid phase extraction, phosphopeptide enrichment, polyacrylamide gel electrophoresis, and desalting. Thus, in these methods, the ADC may be bound to an affinity capture media. The affinity capture media may include at least one of bead- or resin-supported Protein A/G, target antigen-paramagnetic bead capture media, anti-idiotypic antibodies, anti-Hu antibodies, and anti-drug antibodies. These analytical methods may include washing the ADC bound to the affinity capture media to reduce non-antibody proteins in contact with the ADC. These methods may also include dephosphorylating or deglycosylating the ADC bound to the affinity capture media. The step of digesting may also be carried out while ADC is bound to the affinity capture media. Alternatively, or additionally, the ADC may be eluted from the affinity capture media prior to the step of digesting the ADC.

These methods are particularly useful in calculating the total antibody concentration of the ADC from the analysis of the digested ADC composition. Alternatively, or additionally, an antibody-conjugated drug concentration of the ADC is calculated from the analysis of the digested ADC composition. Alternatively, or additionally, the average DAR of the ADC is calculated from the analysis of the digested ADC composition. Alternatively, or additionally, a metabolite or catabolite structure may be determined from the analysis of the digested ADC composition. Alternatively, or additionally, the protein concentration of the ADC may be calculated from the analysis of the digested ADC composition. Alternatively, or additionally, the protein concentration is correlated with a peak area from an RP-LC and/or MS analysis of at least one Fc fragment from the digested ADC. Alternatively, or additionally, the extinction coefficient of the ADC is calculated from the analysis of the digested ADC composition. Alternatively, or additionally, the average DAR of the ADC, metabolite or catabolite structure(s), and the protein concentration of the ADC, are obtained from an RP-LC and/or MS analysis of at least one Fc fragment from the digested ADC.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

DESCRIPTION OF EMBODIMENTS

Figure 1:
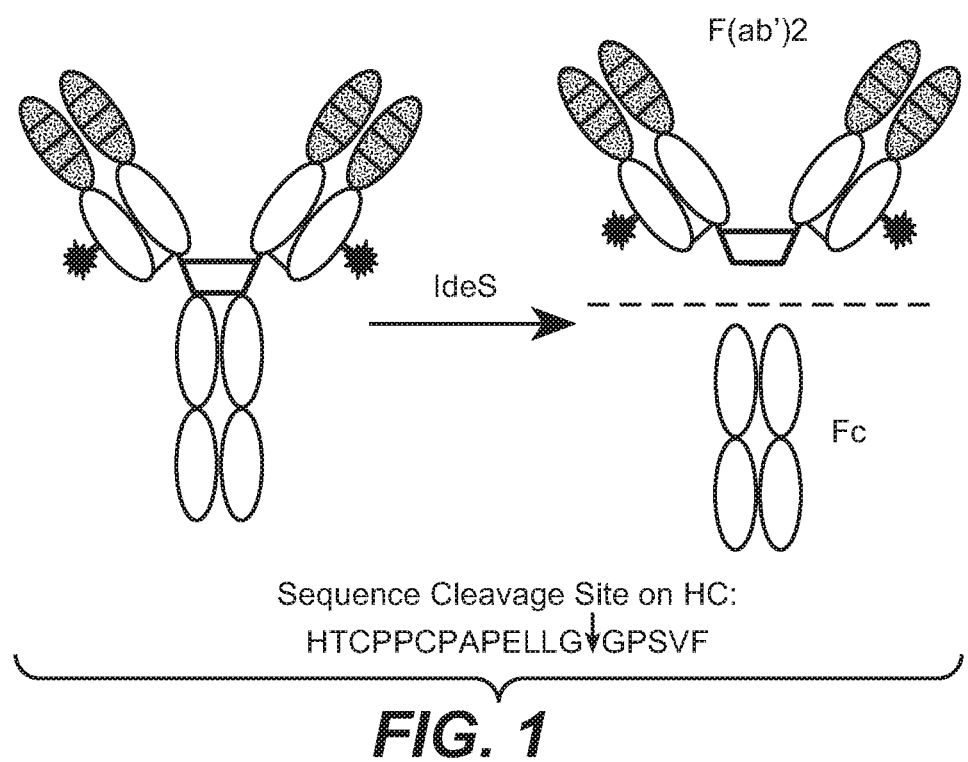
FIG. 1 depicts antibody fragments generated with IdeS protease cleavage of a THIOMAB™ (Genetech, Inc.) drug conjugate (TDC) in which linker-drug is conjugated site-specifically to the F(ab). The digestion produces an F(ab')2 fragment and an Fc fragment. Linker-drug may be conjugated site-specifically to either the F(ab) or Fc.

This disclosure is drawn to single measurement methods to detect and quantify antibody and drug components of antibody drug conjugates (ADCs) that robustly measure total antibody and antibody-conjugated drug quantity from a single sample preparation thereby providing drug to antibody ratio (DAR) calculation and significant time and resource savings.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, the trade name product formulation, the generic drug, and the active pharmaceutical ingredient(s) of the trade name product are also included.

Definitions

The term "biological sample" is any component derived or separated from an animal and includes blood, plasma, serum, cells, urine, cerebrospinal fluid (CSF), milk, bronchial lavage, bone marrow, amniotic fluid, saliva, bile, vitreous, tears, or tissue.

The term "digestive enzyme" is an enzyme capable of cleaving or hydrolyzing peptides or proteins into fragments in either a specific or generic, random manner. A digestive enzyme can form a digested antibody sample from an antibody where the antibody is a component of a biological sample. Digestive enzymes include proteases such as trypsin, papain, pepsin, endoproteinase LysC, endoproteinase ArgC, *Staph aureus* V8, chymotrypsin, Asp-N, Asn-C, PNGaseF, endoproteinase GluC, and LysN.

The term "antibody" is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fc, Fab, Fab', Fab'-SH, F(ab')2; diabodies; linear antibodies; single-chain antibody molecules (e.g. scFv); and multispecific antibodies formed from antibody fragments.

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); WO 93/16185; U.S. Pat. Nos. 5,571,894; 5,587,458. For discussion of Fab and F(ab')2 fragments comprising salvage receptor binding epitope residues and having increased in vivo half-life (U.S. Pat. No. 5,869,046).

Diabodies are antibody fragments with two antigen-binding sites that may be bivalent or bispecific (EP 404097; WO 1993/01161; Hudson et al. (2003) Nat. Med. 9:129-134; Hollinger et al. (1993) Proc. Natl. Acad. Sci. USA 90: 6444-6448). Triabodies and tetrabodies are also described in Hudson et al. (2003) Nat. Med. 9:129-134.

Single-domain antibodies are antibody fragments comprising all or a portion of the heavy chain variable domain or all or a portion of the light chain variable domain of an antibody. In certain embodiments, a single-domain antibody is a human single-domain antibody (U.S. Pat. No. 6,248,516).

Antibody fragments can be made by various techniques, including but not limited to proteolytic digestion of an intact antibody as well as production by recombinant host cells (e.g. *E. coli* or phage), as described herein.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. Sequences of Proteins of Immunological Interest, Fifth Edition, NIH Publication 91-3242, Bethesda Md. (1991), vols. 1-3.

"Framework" or "FR" refers to constant domain residues other than hypervariable region (HVR) residues. The FR of a constant domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

Humanized antibodies and methods of making them have been extensively reviewed, e.g., in Almagro and Fransson, Front. Biosci. 13:1619-1633 (2008), and described, e.g., in Riechmann et al., Nature 332:323-329 (1988); Queen et al., Proc. Nat'l Acad. Sci. USA 86:10029-10033 (1989); U.S. Pat. Nos. 5,821,337; 7,527,791; 6,982,321; 7,087,409;

Kashmiri et al. (2005) Methods 36:25-34 (describing SDR (a-CDR) grafting); Padlan, (1991) Mol. Immunol. 28:489-498 (describing "resurfacing"); Dall'Acqua et al. (2005) Methods 36:43-60 (describing "FR shuffling"); and Osbourn et al, (2005) Methods 36:61-68; Klimka et al. (2000) Br. J. Cancer 83:252-260 (describing the "guided selection" approach to FR shuffling).

Human framework regions that may be used for humanization include but, are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (Carter et al. (1992) Proc. Natl. Acad. Sci. USA, 89:4285; Presta et al. (1993) J. Immunol., 151:2623); human mature (somatically mutated) framework regions or human germline framework regions (Almagro and Fransson, (2008) Front. Biosci. 13:1619-1633); and framework regions derived from screening FR libraries (see, e.g., Baca et al. (1997) J. Biol. Chem. 272:10678-10684; and Rosok et al. (1996) J. Biol. Chem. 271:22611-22618).

Human antibodies are described generally in van Dijk and van de Winkel, (2001) Curr. Opin. Pharmacol. 5: 368-74; Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., (1991) J. Immunol., 147: 86). Human antibodies generated via human B-cell hybridoma technology are also described in Li et al. (2006) Proc. Natl. Acad. Sci. USA, 103:3557-3502. Additional methods include those described in: U.S. Pat. No. 7,189,826 (describing production of monoclonal human IgM antibodies from hybridoma cell lines); Ni, (2006) Xiandai Mianyixue, 26(4):265-268 (describing human-human hybridomas). Human hybridoma technology (Trioma technology) is also described in Vollmers and Brandlein, (2005) Histology and Histopathology, 20(3):927-937 and Vollmers and Brandlein (2005) Methods and Findings in Experimental and Clinical Pharmacology, 27(3):185-91.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

A "human consensus framework" is a framework region of an antibody which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup, as in Kabat et al. supra. In an exemplary embodiment, for the VL, the subgroup is subgroup kappa I. In another exemplary embodiment, for the VH, the subgroup is subgroup III.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "chimeric" antibody refers to an antibody in which a portion of the heavy and/or light chain is derived from a particular source or species, while the remainder of the heavy and/or light chain is derived from a different source or species. An exemplary "chimeric" antibody comprises a non-human variable region (e.g., a variable region derived from a mouse, rat, hamster, rabbit, or non-human primate, such as a monkey) and a human constant region (U.S. Pat. No. 4,816,567; Morrison et al. (1984) Proc. Natl. Acad. Sci. USA, 81:6851-6855). Another exemplary chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Antibodies of this disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in McCafferty et al. (1990) Nature 348:552-554; Clackson et al., Nature 352: 624-628 (1991); Marks et al. (1992) J. Mol. Biol. 222: 581-597; Marks and Bradbury, Methods in Molecular Biology 248: 161-175 (Lo, ed., Human Press, Totowa, N.J., 2003); Sidhu et al. (2004) J. Mol. Biol. 338(2): 299-310; Lee et al. (2004) J. Mol. Biol. 340(5): 1073-1093; Fellouse, (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-55. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., (1993) EMBO J, 12: 725-734. Finally, naive libraries can also be made synthetically by cloning un-rearranged V-gene segments from stem cells, and using PCR primers containing random sequence to encode the highly variable CDR3 regions and to accomplish rearrangement in vitro, as described by Hoogenboom and Winter (1992) J. Mol. Biol., 227: 381-388. Human antibody phage libraries are described in U.S. Pat. Nos. 5,750,373; 7,985,840; 7,785,903; 8,679, 490; 8,054,268; and US 2005/0079574; US 2007/0117126; US 2007/0237764; US 2007/0292936. Antibodies or antibody fragments isolated from human antibody libraries are considered human antibodies or human antibody fragments for the purposes of this disclosure.

An antibody may be a multispecific antibody, e.g. a bispecific antibody. Multispecific antibodies are monoclonal antibodies that have binding specificities for at least two different sites. One of the binding specificities may be for one antigen while the other is for a second antigen. Alternatively, bispecific antibodies may bind to two different epitopes of the same antigen. Bispecific antibodies may also be used to localize cytotoxic agents to cells which express an antigen. Bispecific antibodies can be prepared as full length antibodies or antibody fragments (see, e.g., Ortiz-Sanchez et al., Expert Opin. Biol. Ther. (2008) 8(5):609-32).

Techniques for making multispecific antibodies include, but are not limited to, recombinant co-expression of two immunoglobulin heavy chain-light chain pairs having different specificities (see Milstein and Cuello, Nature 305: 537 (1983)), WO 1993/08829, and Traunecker et al., EMBO J. 10: 3655 (1991)), and "knob-in-hole" engineering (U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (e.g., Kostelny et al. (1992) J. Immunol. 148(5):1547-1553); using "diabody" technology for making bispecific antibody fragments (e.g., Hollinger et al., (1993) Proc. Natl. Acad. Sci. USA, 90:6444-448); and using single-chain Fv (sFv) dimers (Gruber et al. (1994) J. Immunol., 152:5368); and preparing trispecific antibodies (Tutt et al. (1991) J. Immunol. 147: 60).

Engineered antibodies with three or more functional antigen binding sites, including "Octopus antibodies," are also included herein (e.g. US 2006/0025576).

The antibody or fragment herein also includes a "Dual Acting FAb" or "DAF" comprising an antigen binding site that binds to an antigen as well as another, different antigen (e.g., US 2008/0069820).

Antibody Variants

Amino acid sequence variants of the antibodies provided herein are also contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Antibodies include fusion proteins comprising an antibody and a protein, drug moiety, label, or some other group. Fusion proteins may be made by recombinant techniques, conjugation, or peptide synthesis, to optimize properties such as pharmacokinetics. The human or humanized antibodies may also be a fusion protein comprising an albumin-binding peptide (ABP) sequence (see, Dennis et al (2002) J Biol. Chem. 277:35035-35043 at Tables III and IV, page 35038; US Pat. Pub. No. 2004/0001827 at [0076]; and WO 01/45746 at pages 12-13, all of which are incorporated herein by reference).

Substitution, Insertion, and Deletion Variants

Antibody variants having one or more amino acid substitutions are provided for use and analysis in the methods of this disclosure. Sites of interest for substitutional mutagenesis include the HVRs and FRs. Substantial changes are provided in the following table under the heading of "exemplary substitutions," and are further described below in reference to amino acid side chain classes. Amino acid substitutions may be introduced into an antibody of interest and the products screened for a desired activity, e.g., retained/improved antigen binding, decreased immunogenicity, or improved antibody-dependent cell-mediated cytotoxicity (ADCC) or CDC.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, (2008) Methods Mol. Biol. 207:179-196), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-85. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (Wright et al. (1997) TIBTECH 15:26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry (see, e.g., WO 2008/077546). Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function (U.S. Pat. Pub. Nos. 2003/0157108; US 2004/0093621). Patent publications describing "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. (2004) Biotech. Bioeng. 87:614. Cell lines capable of producing defucosylated antibodies include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (Yamane-Ohnuki, et al. (2004) Biotech. Bioeng. 87:614; Kanda, et al. (2006) Biotechnol. Bioeng., 94(4):680-688; WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Publications describing such antibody variants having bisected oligosaccharides include WO 2003/011878; U.S. Pat. No. 6,602,684; and US Pat. Pub. 2005/0123546. Antibody variants with at least one galactose residue in the oligosaccharide attached to the Fc region are also provided and may have improved CDC function. Publications describing such galactose residue antibody variants include WO 1997/30087; WO 1998/58964; WO 1999/22764.

Site-Specific Antibody Drug Conjugates

As noted above, one of the main challenges in ADC design is the homogeneity of currently available ADCs that may have zero to eight drug molecules linked to each antibody or antibody fragment. This heterogeneity in ADC species adversely influences analytical methods of evaluating and monitoring stability, consistency, pharmacokinetics, and in vivo performance of ADC compositions. For this reason, conjugation strategies have been identified that permit chemical installation of the drug onto an antibody at pre-determined site(s), to ensure stability of the conjugate following production and, while in circulation, in vivo. These site-specific ADCs, also referred to as immunoconjugates, rely on emerging site-specific conjugation strategies that includes the use of engineered cysteines (e.g., THIO-MAB™, Genetech Inc.), unnatural amino acids, selenocysteine residues, enzymatic conjugation through glucotransferase and transglutaminasesl, and other techniques. In particular, THIOMAB™-drug conjugates (TDCs) can be controlled to produce a homogeneous DAR2.

1) Cysteine Engineered Antibody Drug Conjugates

Cysteine-engineered antibodies (e.g., a THIOMAB™, Genentech, Inc.), comprise one or more residues of an antibody substituted with cysteine residue(s). The substituted residues may occur at accessible sites of the antibody, such that reactive thiol groups are positioned at accessible sites of the antibody and may be used to conjugate the antibody to other moieties, such as drug moieties or linker-drug moieties, to create a site-specific ADC. Examples of such THIOMAB™ (Genentech, Inc.) antibodies include cysteine engineered antibodies in which any one or more of the following residues may be substituted with cysteine: V205 (Kabat numbering) of the light chain; A118 (EU numbering) of the heavy chain; and S400 (EU numbering) of the heavy chain Fc region, and S121, and K149 of the light chain. Methods of making cysteine engineered antibodies include, but are not limited to, the methods described in U.S. Pat. Nos. 7,521,541; 9,000,130.

Thus, the methods of this disclosure may be applied to antibody-drug conjugates comprising cysteine engineered antibodies wherein one or more amino acids of a wild-type or parent antibody are replaced with a cysteine amino acid (THIOMAB™, Genentech, Inc.) antibody. Any form of antibody may be so engineered. For example, a parent Fab antibody fragment may be engineered to form a cysteine engineered Fab, and a parent monoclonal antibody may be engineered to form a cysteine engineered monoclonal antibody. It should be noted that a single site mutation yields a single engineered cysteine residue in a Fab antibody fragment, while a single site mutation yields two engineered cysteine residues in a full length antibody, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

Cysteine amino acids may be engineered at reactive sites in the heavy chain (HC) or light chain (LC) of an antibody and which do not form intrachain or intermolecular disulfide linkages (Junutula, et al. (2008) Nature Biotech., 26(8):925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) J. Immuno. Methods 332:41-52). The engineered cysteine thiols may react with linker reagents or the linker-drug intermediates of the present invention which have thiol-reactive, electrophilic pyridyl disulfide groups to form ADC with cysteine engineered antibodies and the drug moiety. The specific location (i.e., site) of the drug moiety in these engineered ADCs can thus be designed, controlled, and known. The drug loading can therefore be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading (DAR) near 2 can be achieved, with nearly complete homogeneity in these site specific conjugated ADCs.

2) Unnatural Amino Acid Engineered Antibody Drug Conjugates

Similar to cysteine-engineered antibodies, the incorporation of unnatural amino acids (UAAs) into proteins provides a flexible method of site-specifically engineering a bioorthogonal functionality (see, e.g., Agarwal and Bertozzi, Bioconjugate Chem. 2015, 26:176-92; Sochaj, et al., Biotech. Advances (2015) 33:775-84). To design and specifically introduce a non-natural amino acid into a protein such as an antibody or antibody fragment, a mutant protein encoded by a gene with the amber stop codon (TAG) at the site of the desired UAA may be expressed in cells, along with a corresponding orthogonal tRNA/aminoacyl-tRNA synthetase (aaRS) pair capable of installing the UAA at the amber stop codon site (see, e.g., Liu and Schultz (2010) Annu. Rev. Biochem. 79:413-44). One unnatural amino acid incorporated in *E. coli* UAA expression systems was p-acetylphenylalanine, chosen for the bioorthogonal reactivity of its ketone (Wang, et al., (2003) Proc. Natl. Acad. Sci. U.S.A. 100:56-61.). This unnatural amino acid was conjugated to an aminooxy-auristatin F, and the resulting trastuzumab antibody displayed superior pharmacokinetic properties in mice (Tian, et al., (2014) Proc. Natl. Acad. Sci. U.S.A. 111: 1766-1771). This site-specific engineering methodology can be expanded to include more than one biorthogonal functional group into the protein. This approach, based on the incorporation of one or more unnatural amino acids into the protein, may provide antibody-drug conjugates with a specific number of known unnatural amino acid substitutions that are easily and consistently conjugated to a therapeutic moiety, such as an anti-cancer drug, producing a very homogenous ADC composition with drug conjugation(s) limited to precisely designed and identified sites in the protein.

3) Selenocysteine Engineered Antibody Drug Conjugates

Selenocysteine is a natural, but rare, amino acid that exists in all kingdoms of life as a component of selenoproteins, of which only 25 are currently known in mammals. Selenocysteine contains selenium in the place of sulfur, which makes it more reactive towards electrophiles in acidic conditions than cysteine. This chemical property was used to selectively couple maleimide- and iodoacetamide-containing agents to antibodies containing genetically engineered selenocysteine residues (Hofer, et al. (2009) Biochemistry 48:12047-57; Li, et al., (2014) Methods 65:133-38). Selenocysteine was used to conjugate fluorescent probes, biotin and biotin polyethylene glycol (biotin-PEG) to antibodies, resulting in the fully functional conjugates having specifically defined sites and stoichiometries of agent attachment, demonstrating the production of homogenous ADCs based on selenocysteine residue engineering. (see, e.g., Agarwal and Bertozzi, (2015) Bioconjugate Chem. 26:176-92; Sochaj, et al. (2015) Biotech. Advances 33:775-84).

4) Glycan Modified Antibody Drug Conjugates

Human IgG molecules have a conserved glycosylation site at each N297 residue in the CH2 domain, making these pendant N-glycans a convenient target for site-specific conjugation. This glycosylation site is sufficiently far from the variable region that conjugation of drug moieties to attached glycans should not impact antigen binding. One method of linking therapeutic moieties to these glycans includes oxidative cleavage of the vicinal diol moieties contained in these glycans with periodate to generate aldehydes that can be reductively aminated and conjugated to hydrazide and aminooxy compounds (O'Shannessy, et al. (1984) Immunol. Lett. 8:273-77). Another method includes increasing the fucosylation of the N-acetylglucosamine residues in these glycans. Oxidation of these fucose residues produces carboxylic acid and aldehyde moieties that can be used to link drugs and fluorophores to these specific sites on the antibody (Zuberbuhler, et al. (2012) Chem. Commun. 48:7100-02). Another method includes modifying sialic acid in these glycans (as well as increasing the sialic acid content in these glycans) followed by oxidation of the sialic acid and conjugation with aminooxy-drugs to form oxime-linked conjugates (Zhou, et al. (2014) Bioconjugate Chem. 25:510-20). Alternatively, a sialyltransferase may be used to incorporate a modified sialic acid residue containing a bioorthogonal functional group into these glycans. The bioorthogonal functional group may then be modified to attach therapeutic moieties to the site of the glycan (Li, et al. (2014) Angew. Chem. Int. 53:7179-82). Another approach to modifying these glycan sites is the use of glycosyltransferases to link galactose, or galactose analogues containing ketones or azides, to the N-acetylglucosamine in these glycans, and linking drugs or radionucleotides to the galactose molecules (Khidekel, et al., (2003) J. Am. Chem. Soc. 125:16162-63; Clark, et al., (2008) J. Am. Chem. Soc. 130:11576-77; Boeggeman, et al. (2007) Bioconjugate Chem. 18:806-14). Another approach relies on the introduction of modified sugars into these glycans at the time of expression of the antibody by metabolic oligosaccharide engineering (Campbell, et al. (2007) Mol. BioSyst. 3:187-94; Agard, et al., (2009) Acc. Chem. Res. 42:788-97). This approach has been utilized with the introduction of fucose analogues followed by drug linking/modification at the fucosylation site (Okeley, et al. (2013) Bioconjugate Chem. 24:1650-1655; Okeley, et al., (2013) Proc. Natl. Acad. Sci. U.S.A. 110:5404-09.).

5) Probody Drug Conjugates

Probodies (PROBODY™, Cytomx Therapeutics LLC, South San Francisco, Calif.) are recombinant, proteolytically-activated antibody prodrugs, comprised of a monoclonal antibody in which the amino terminus of the antibody light chain is extended with a protease-cleavable linker and a masking peptide designed to block antibody binding to an antigen (U.S. Pat. No. 8,563,269; Desnoyers, et al., Sci Transl Med. 2013 16; 5(207):207ra144; Polu and Lowman, Expert Opin Biol Ther. 2014, 14(8):1049-53; Wong, et al., Biochimie. 2016 122:62-7). Cleavage of the linker by specific tumor-associated proteases leads to dissociation of the mask and release of an antibody competent to bind to antigen in the tumor. Probodies are designed to exploit the fundamental dysregulation of extracellular protease activity that exists within the tumor microenvironment, relative to healthy tissue, thereby binding only minimally to antigen in healthy tissue where there are insufficient active proteases present to remove the mask. Within a tumor, in the presence of sufficient dysregulated protease activity, the mask is removed by cleavage of the linker, and antigen binding proceeds. Probody Drug Conjugates (PDCs) have been engineered to bind a probody to the microtubule inhibitor MMAE (Weidle, et al., Can Gen & Proteom 2014, 11:67-80; Sagert, et al., Abstract 2665, AACR Annual Meeting 2014).

6) Polymer or Peptide Conjugates

Antibody drug conjugates are also formed using antibodies, or antibody fragments, linked to hydrophilic polymers or peptides that are comprised of natural amino acids, which can themselves be attached to therapeutic peptides, proteins or small therapeutic molecules. Thus, the polymer or peptide essentially serves as a linker between the antibody and the therapeutic moiety (drug), but this linker provides a means to attach multiple therapeutic moieties, thereby significantly increasing DAR for each ADC molecule. Using these constructs, DAR of 14-18, or even higher, are possible while maintaining the site-specific conjugation attributes of a site-specific ADC. Exemplary ADCs that include such peptide/polymer conjugates include ADCs linked to the XTEN™ peptides conjugate (Amunix, Mountain View, Calif.) at specific, engineered amino acid residues in the light chain of the antibody, such as the cysteine-engineered antibodies described above. These peptides are substantially homogeneous polypeptides that are useful as conjugation partners to link to one or more payloads via a cross-linker reactant resulting in an XTEN-payload ADC conjugate. These peptide linkers are polypeptides composed of non-naturally occurring, substantially non-repetitive sequences having a low degree, or no secondary or tertiary structure under physiologic conditions, and typically have from about 36 to about 3000 amino acids, of which the majority or the entirety are small hydrophilic amino acids with defined numbers of orthogonal pendant reactive groups conjugated to one or more molecules of a targeting moiety that serves as a ligand to a cell-surface receptor and one or more molecules of an effector drug (U.S. Pat. Pub. 2015/0037359).

7) Fc Fusion Proteins

There are a broad variety of antibody-cytokine fusion proteins that have been developed as biopharmaceutical products and approved by the FDA for use as drugs in the United States. Most of these fusion proteins target tumor antigens with a protein construct in which different cytokines have been fused to full-length antibodies or their derivatives (see, e.g., Ortiz-Sanchez et al. (2008) Expert Opin. Biol. Ther. 8(5):609-32; Sochaj, et al. (2015) Biotechnology Advances 33:775-84). Each cytokine can be fused at the amino- or carboxy-terminus of the antibody depending on the structure of the cytokine and antibody, in order to conserve the biological activity of both components. Between the growing number of antibody derivatives, and the different cytokines that can be combined with them, the quantity of different antibody-cytokine fusion proteins is very large. Additionally, Fc-fusion constructs are being developed for non-cancer clinical indications such as autoimmune conditions. These proteins may directly compete with antibodies that target self proteins. Generally, these Fc-fusion protein constructs have been categorized into four groups based on ligand specificity (binding to one or multiple epitopes on a ligand molecule) and valency (stoichiometry of binding to ligand molecules): bivalent with single-ligand specificity; monovalent with multi-ligand specificity; multivalent with single-ligand specificity; and monovalent with single-ligand specificity.

Other than the Fc-fusion protein constructs, these site-specific, engineered immunoconjugates may retain the antigen binding capability of their wild type, parent antibody counterparts. Thus, the site-specific antibody conjugates are capable of binding, preferably specifically, to antigens. Such antigens include, for example, tumor-associated antigens (TAA), cell surface receptor proteins, and other cell surface molecules, transmembrane proteins, signaling proteins, cell survival regulatory factors, cell proliferation regulatory factors, molecules known or suspected to contribute functionally to tissue development or differentiation, lymphokines, cytokines, molecules involved in cell cycle regulation, molecules involved in vasculogenesis, and molecules known or suspected to contribute functionally to angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The site specific antibody conjugates used in the methods of this disclosure include immunoconjugates useful in the treatment of cancer including, but not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal, non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed below. Information relating to these antigens, which are known in the art, is listed below and includes names, alternative names, Genbank accession numbers, and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 2:
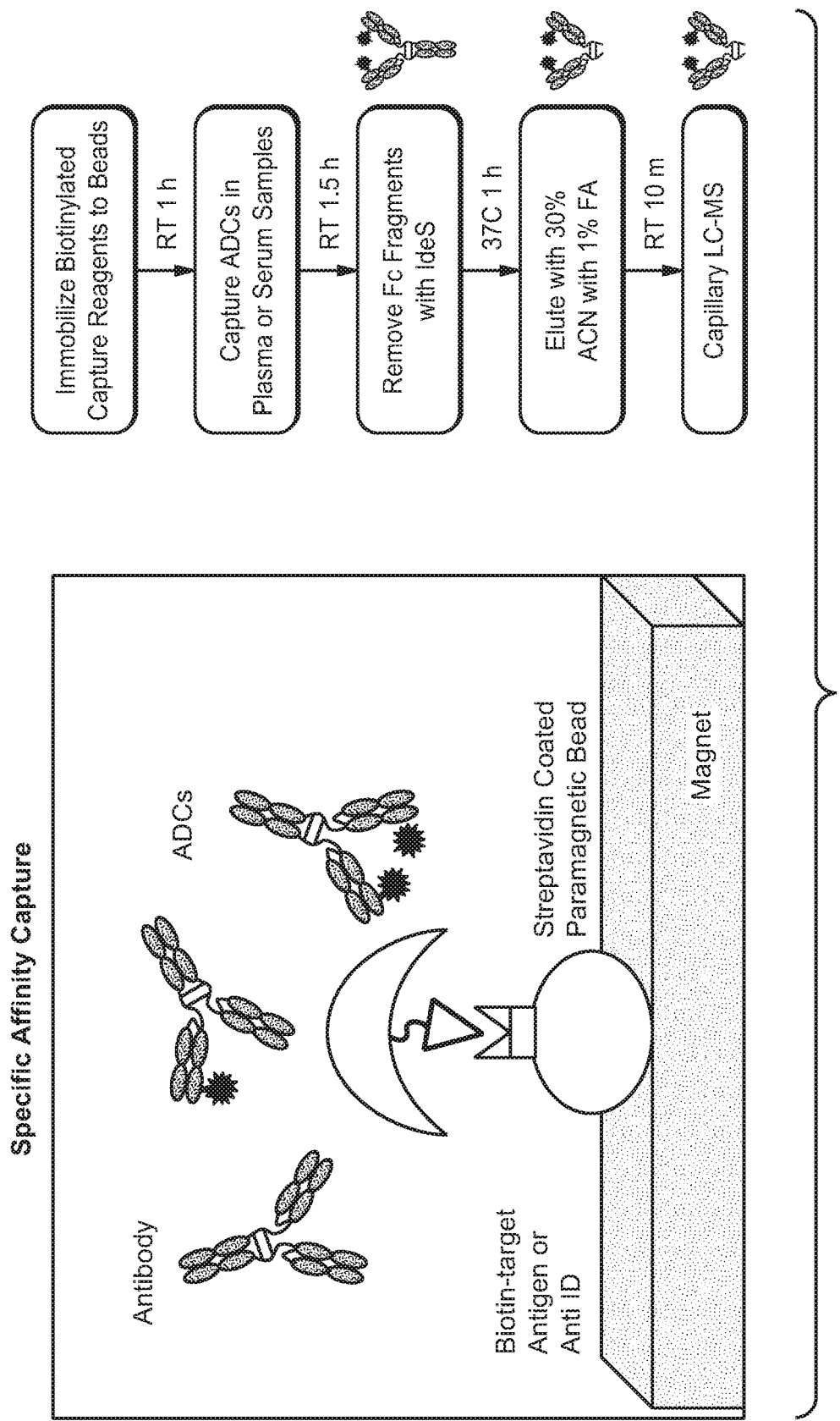
FIG. 2 provides a schematic illustration of the IdeS digestion, 2nd-generation affinity capture LC-MS.
Figure 3:
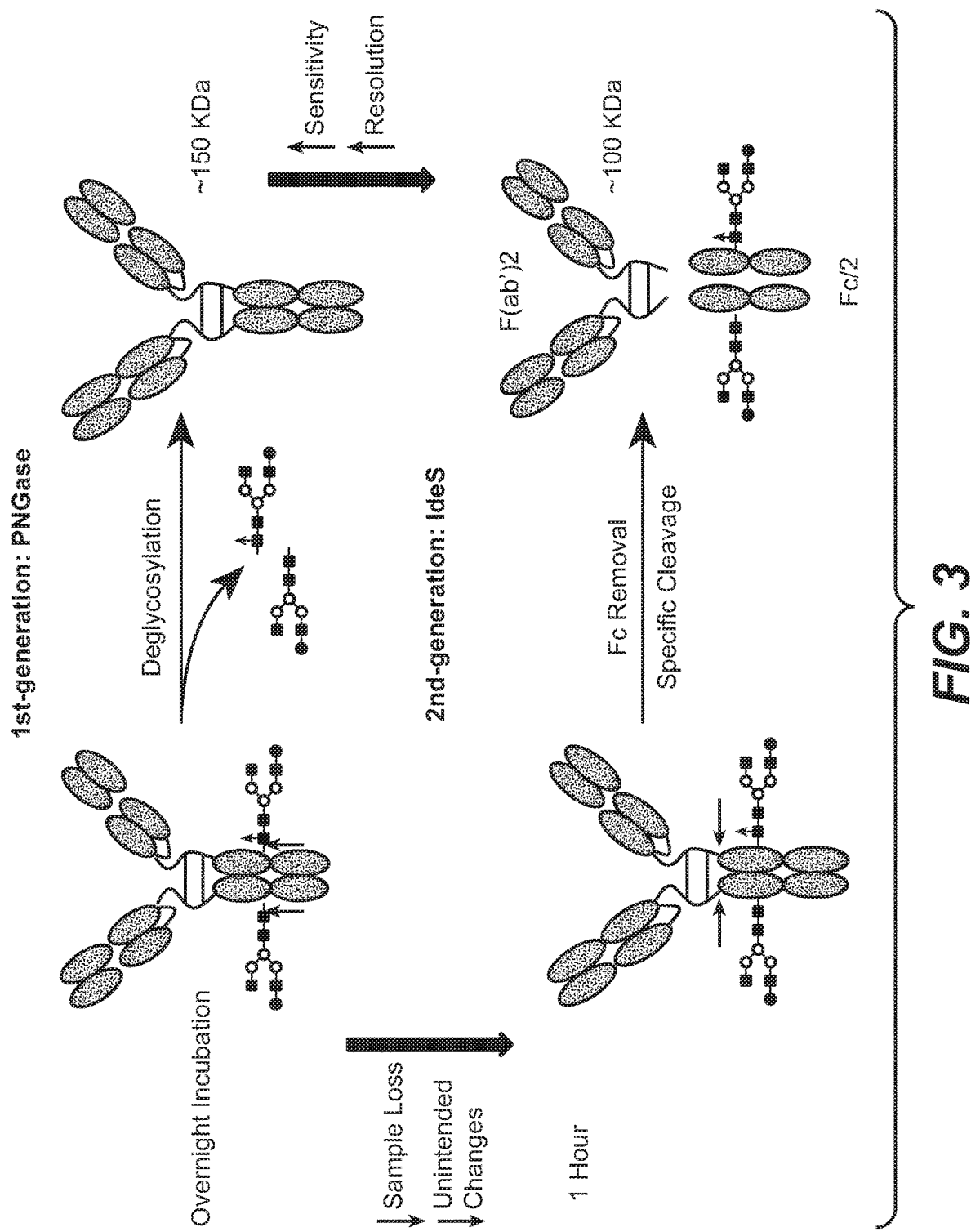
FIG. 3 shows a schematic illustration of PNGase F ($1^{st}$-generation) and IdeS ($2^{nd}$-generation) digestion and the advantages of the 2nd-generation affinity capture LC-MS assay of this disclosure.
Figure 4:
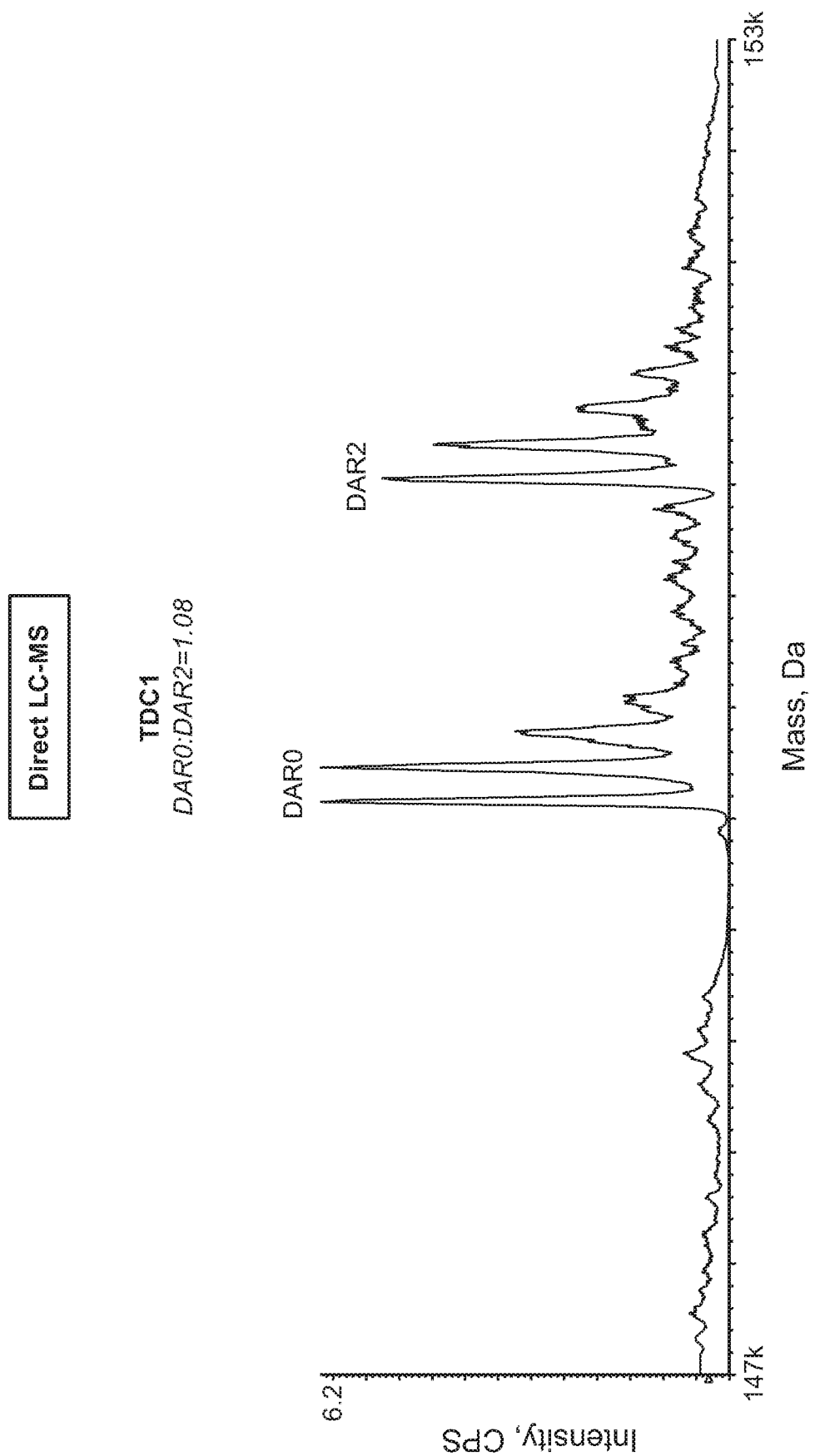
FIG. 4 shows direct LC-MS affinity capture LC-MS analysis of a TDC standard mixture (DAR0:DAR2=1:1).
Figure 6:
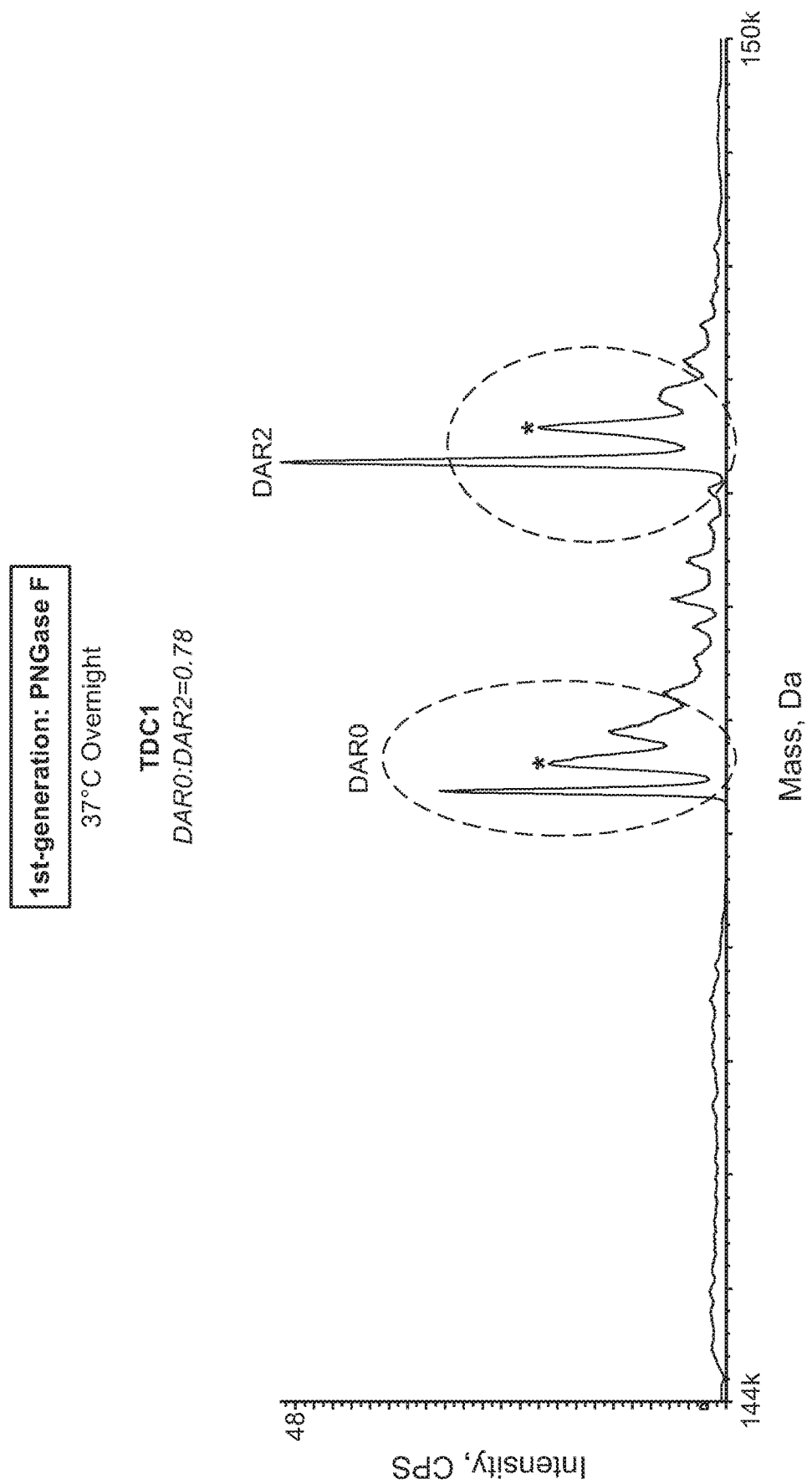
FIG. 6 shows 1st-generation affinity capture LC-MS analysis of a TDC standard mixture (DAR0:DAR2=1:1). MS peaks labeled with * represent DARs with glycans.
Figure 7:
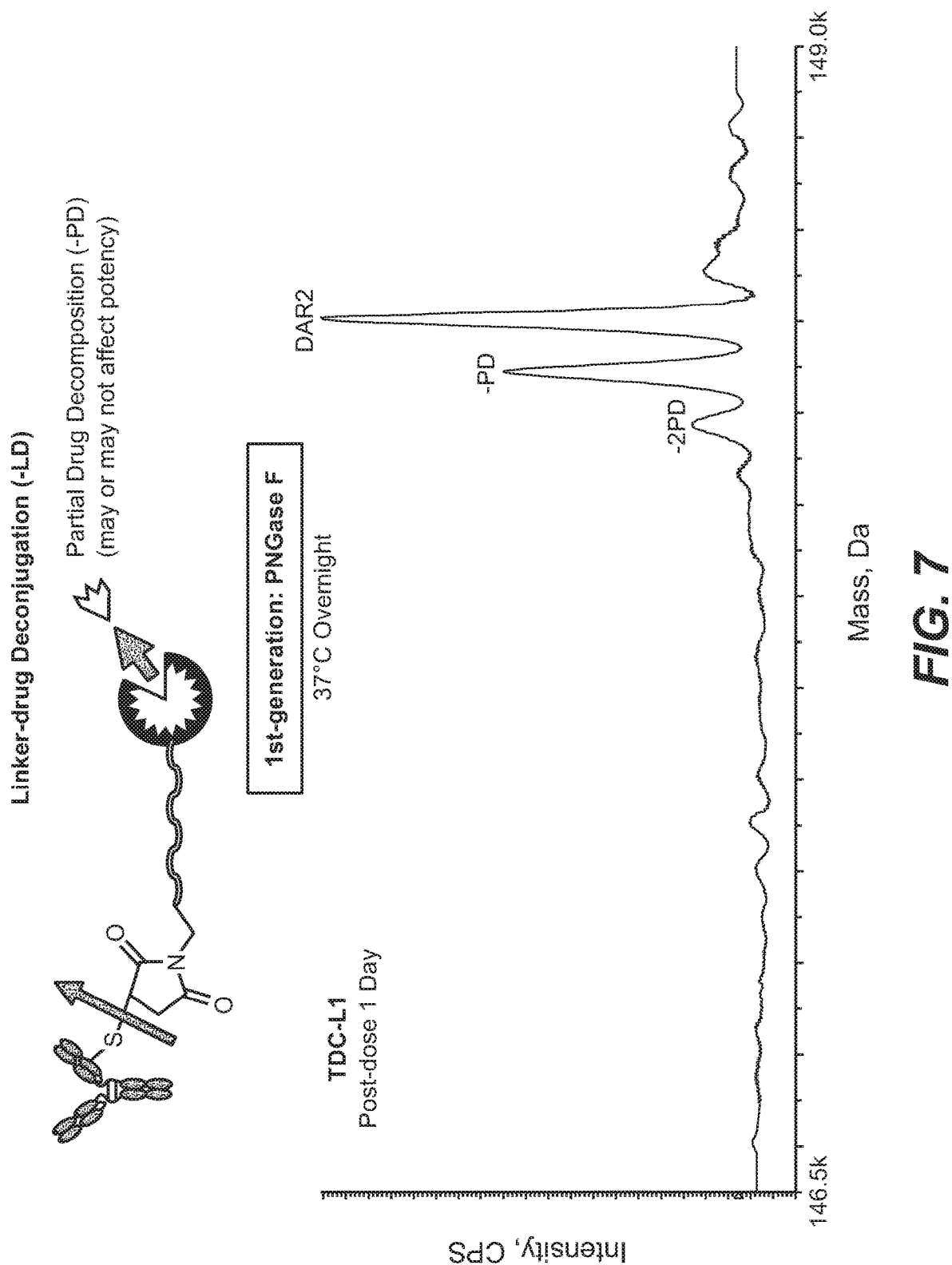
FIG. 7 shows linker-drug deconjugation (−LD) and PNGaseF digestion, 1st-generation analysis of a labile TDC, TDC-L1, from rat plasma.
Figure 8:
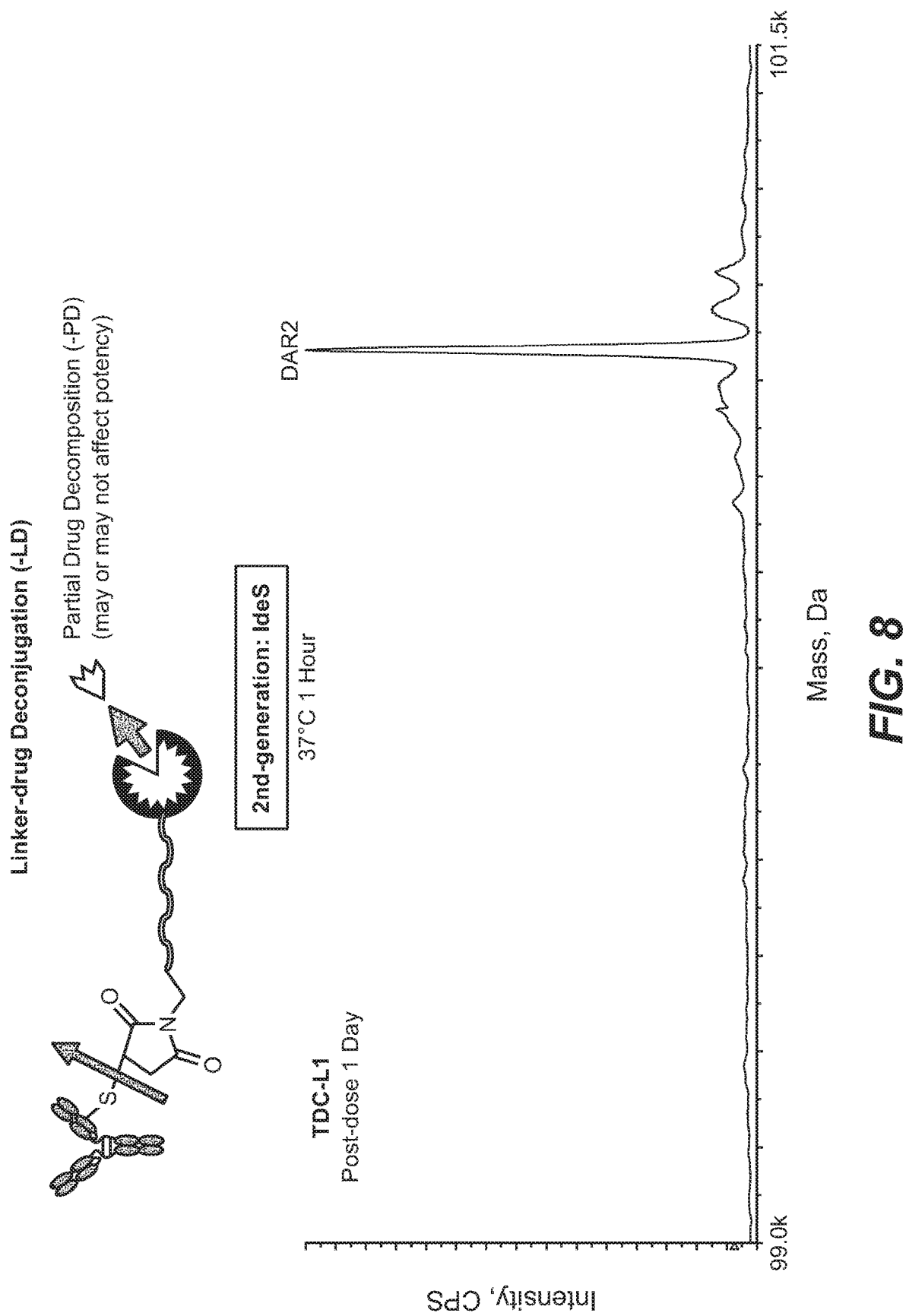
FIG. 8 shows linker-drug deconjugation (−LD) and IdeS digestion, 2nd-generation (1E-2) analysis of a labile TDC, TDC-L1, from rat plasma. Artificial partial drug decomposition (−PD) was minimized by the 2nd-generation affinity capture LC-MS assay (B). Partial drug decomposition didn't impact the potency of TDC-L1, leading to no change in DAR.
Figure 9:
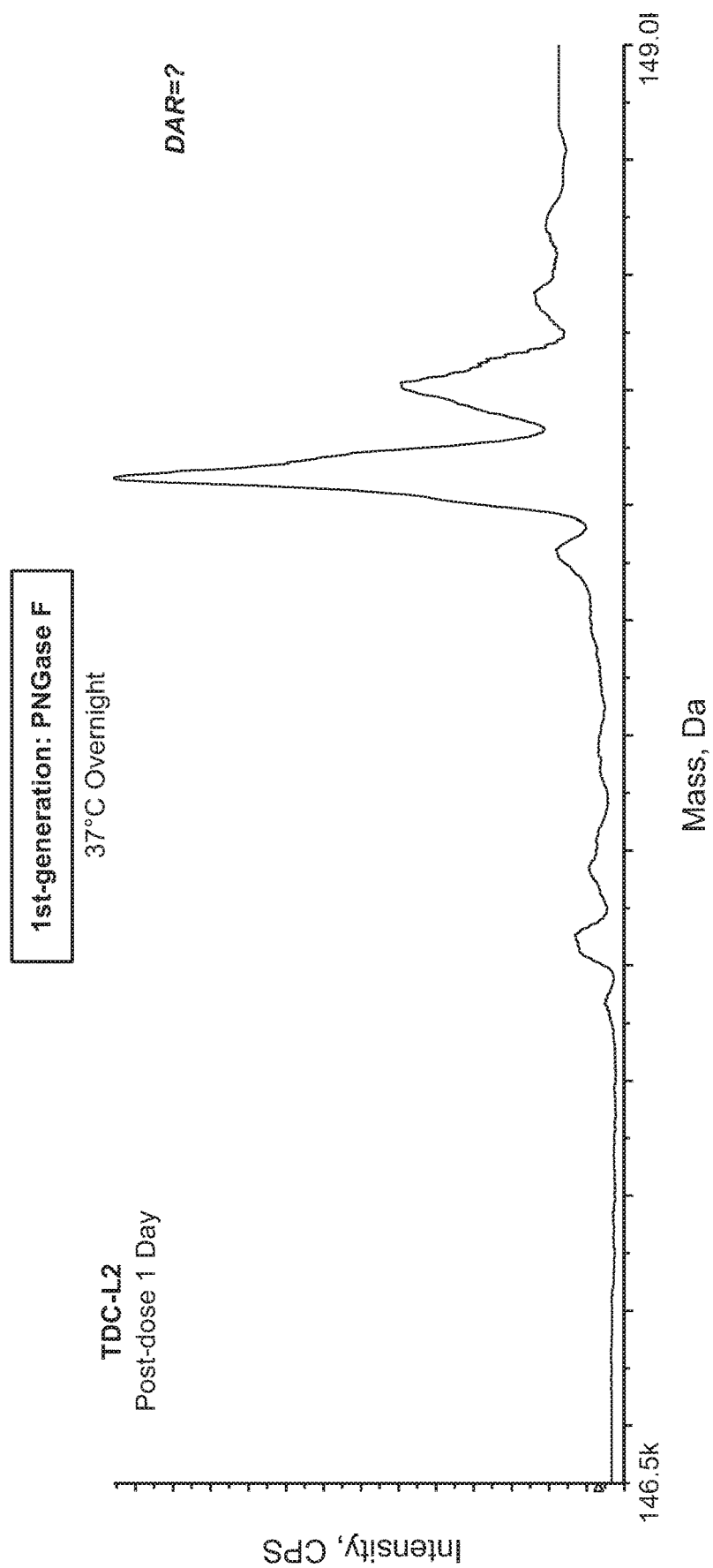
FIG. 9 shows MS peaks obtained during characterization of complicated TDC catabolites in mouse plasma in vivo. Due to loss of 42 Da from the drug molecule, MS peaks of TDC-L2 catabolites were not resolved in PNGaseF digestion (1st-generation) affinity capture LC-MS assay. Partial drug decomposition (−PD, 43 Da) significantly impacted the potency of the example TDC-L2, leading to the reduction of DAR accordingly.
Figure 10:
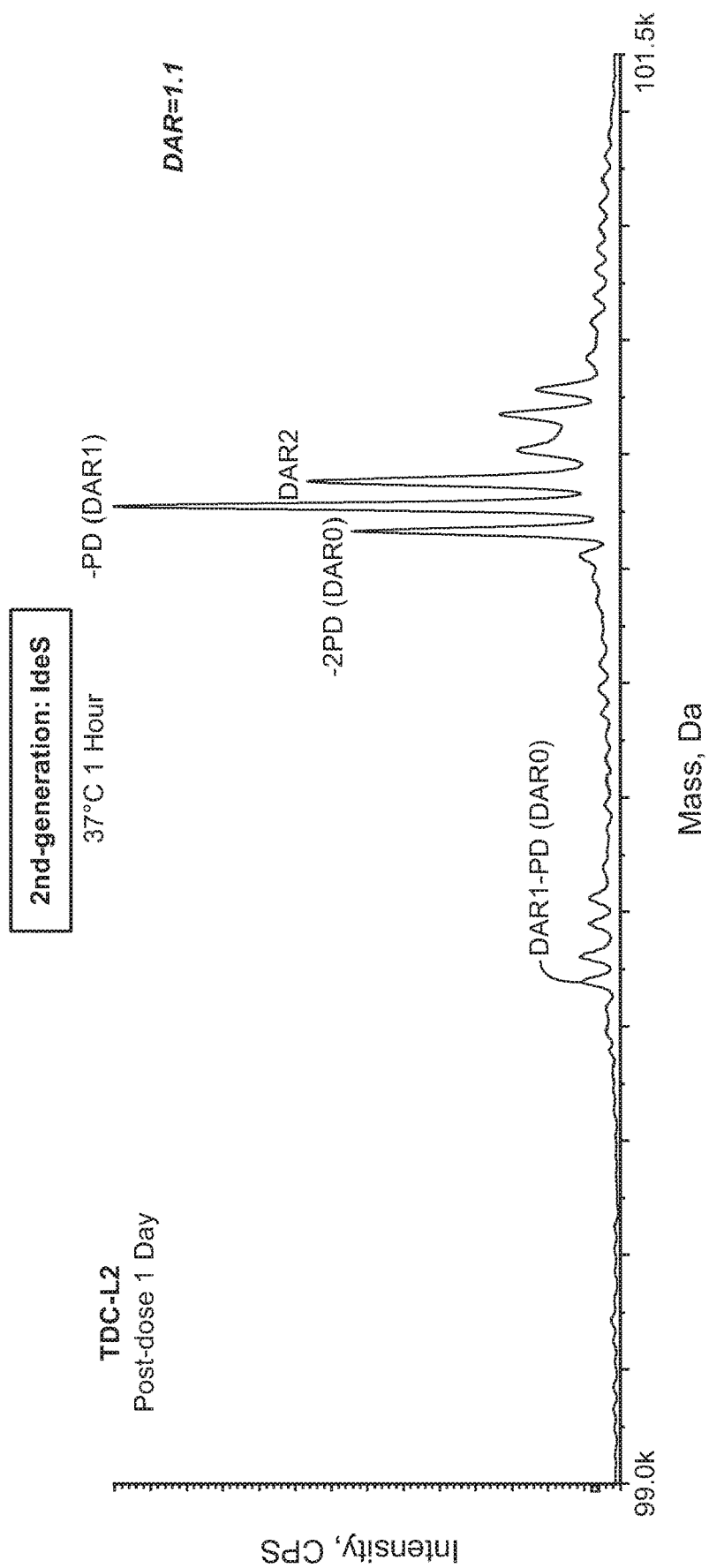
FIG. 10 shows MS peaks obtained during characterization of complicated TDC catabolites in mouse plasma in vivo. Due to loss of 42 Da from the drug molecule, MS peaks of TDC-L2 catabolites were near baseline-resolved using the IdeS digestion (2nd-generation assay). Partial drug decomposition (−PD, 43 Da) significantly impacted the potency of the example TDC-L2, leading to the reduction of DAR accordingly.
Figure 12:
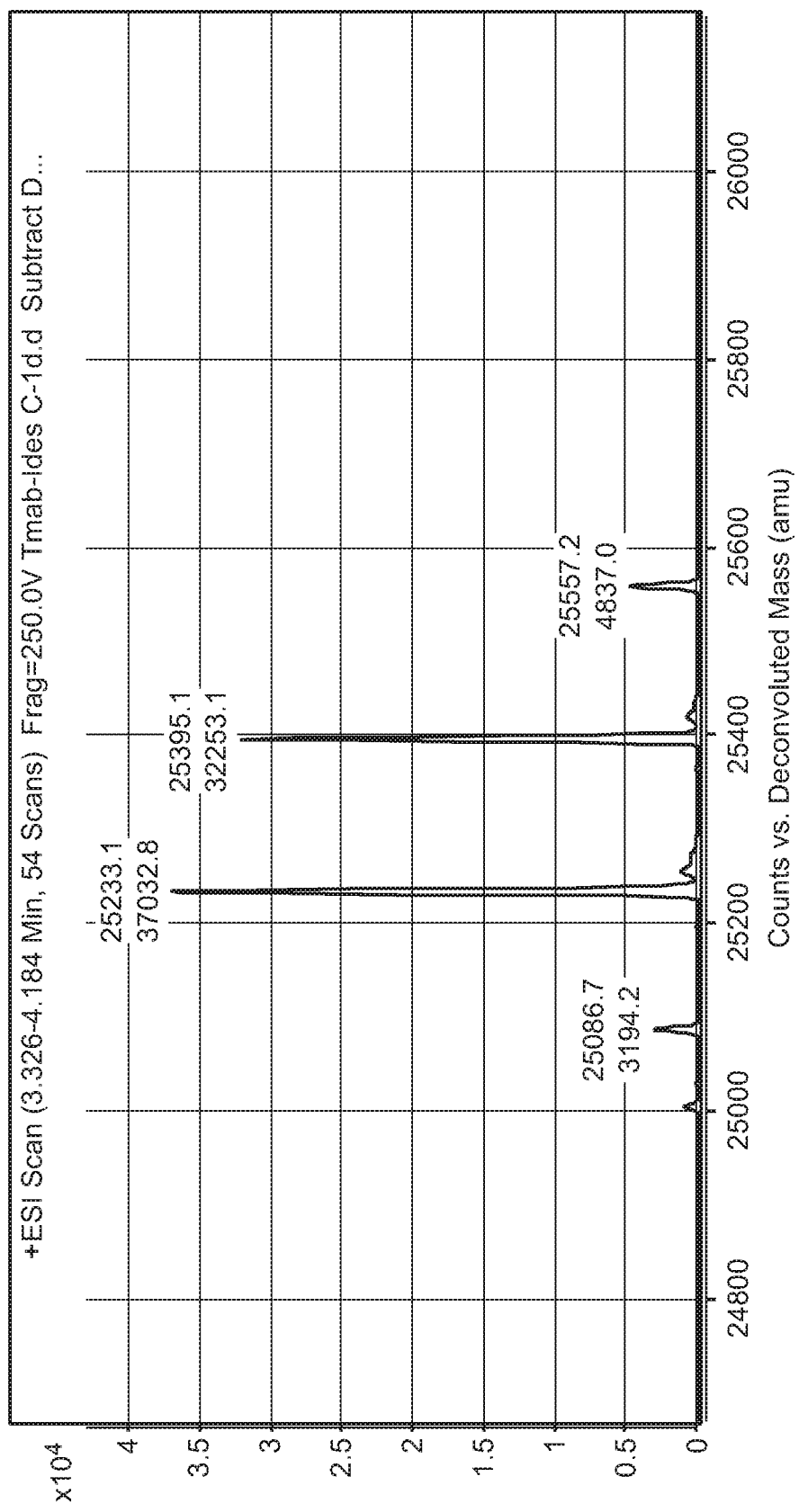
FIG. 12 shows the deconvoluted mass spectrum of Fc/2 from the analysis of FIG. 11.
Figure 13A:
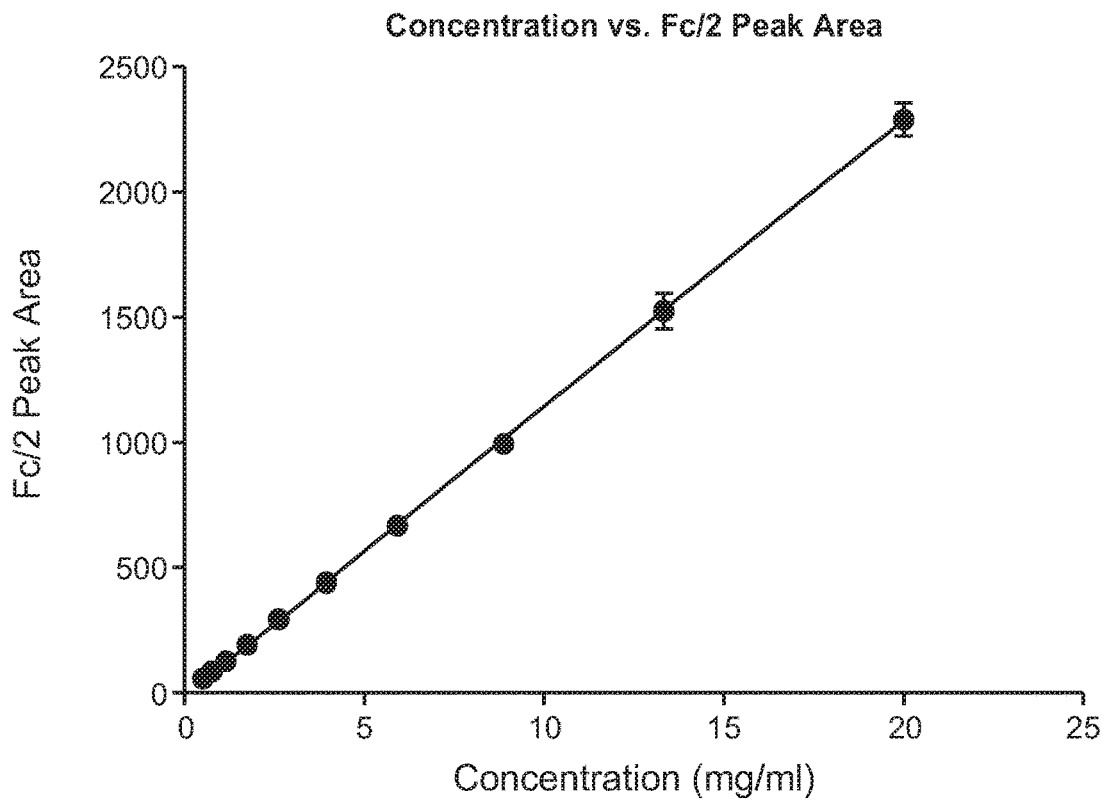
FIG. 13A shows a standard curve of Fc/2 peak area vs. concentration over a range of 0.5-20 mg/ml generated using Trastuzumab digested with IdeS protease. Protein concentration of TDCs site-specifically conjugated on the F(ab) can be determined using peak area of the Fc/2 of the TDC and the linear regression. Traditional ADCs conjugated on inter-chain disulfides can also be characterized using this method as the Fc/2 fragment is also without drug in these conjugates.
Figure 17:
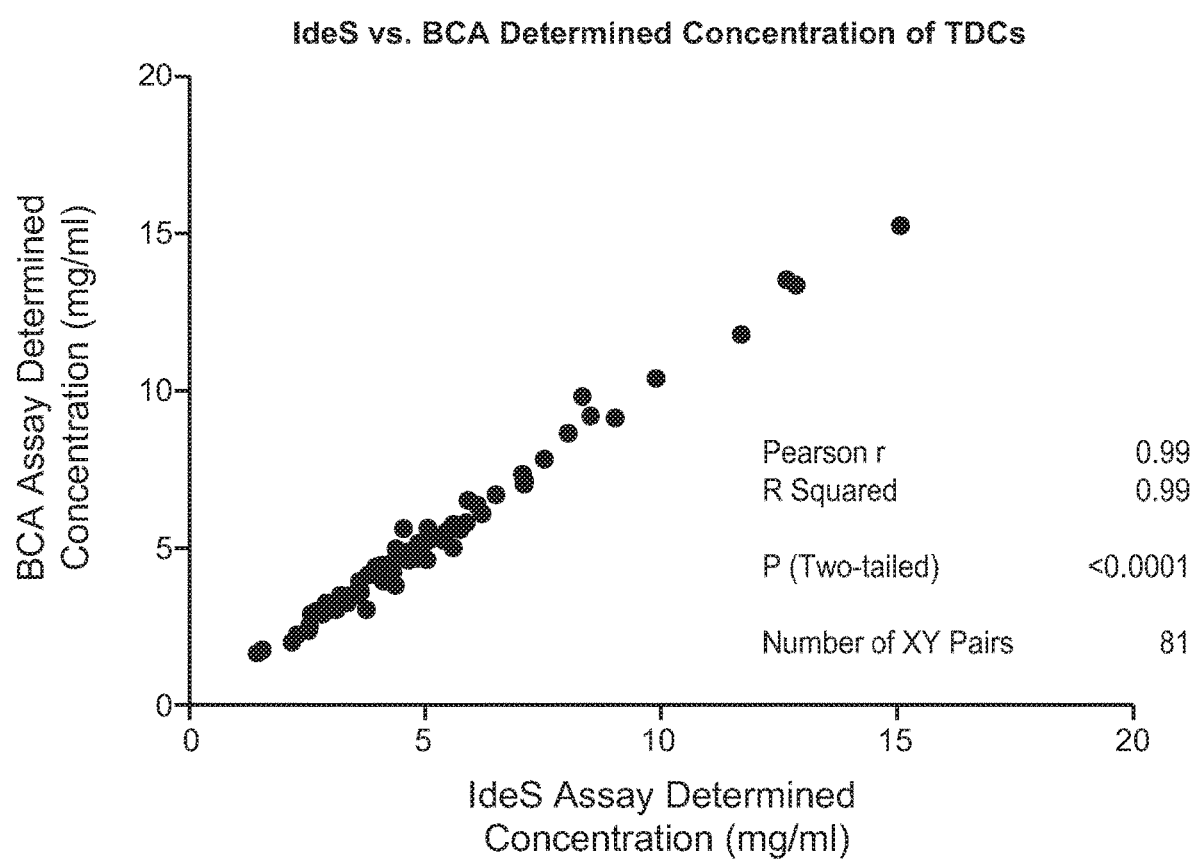
FIG. 17 shows a correlation of 81 THIOMAB™ drug conjugate concentration values obtained by the IdeS protease digest method of this disclosure or a bicinchoninic acid assay (BCA) protein assay.

Tumor-Associated Antigens (1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4) NP_001194 bone morphogenetic protein receptor, type D3/pid=NP_001194.1—Cross-references: MIM:603248; NP_001194.1; AY065994;

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+system), member 5/pid=NP_003477.3—*Homo sapiens* Cross-references: MIM:600182; NP_003477.3; NM_015923; NM_003486_1;

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate. Cross-references: MIM: 604415; NP_036581.1; NM_012449_1;

(4) 0772P (CA125, MUC16, Genbank accession no. AF361486) J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); U.S. Pat. No. 798,959. Cross-references: GI:34501467; AAK74120.3; AF361486_1;

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MIM:601051; NP_005814.2; NM_005823_1;

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140);
Cross-references: MIM:604217; NP_006415.1; NM_006424_1;
(7) Sema 5b (F1110372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)
Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: Q9P283; EMBL; AB040878; BAA95969.1. Genew; HGNC:10737;
(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1;
(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, sl-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206); WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;
(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1;
(11) STEAP2 (HGNC 8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)
Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1;
(12) TrpM4 (BR22450, FLJ20041, TRPM4, TRPM4B, transient receptor potential cation channel, subfamily M, member 4, Genbank accession no. NM_017636). Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D);
Cross-references: MIM:606936; NP_060106.2; NM_017636_1;
(13) CRIPTO (CR, CR1, CRGF, CRIPTO, TDGF1, teratocarcinoma-derived growth factor, Genbank accession no. NP_003203 or NM_003212). Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2);
Cross-references: MIM:187395; NP_003203.1; NM_003212_1;
(14) CD21 (CR2 (Complement receptor 2) or C3DR (C3d/Epstein Barr virus receptor) or Hs.73792 Genbank accession no. M26004). Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIGS. 9.1-9.9); WO2004020595 (claim 1); Accession: P20023; Q13866; Q14212; EMBL; M26004; AAA35786.1;
(15) CD79b (CD79B, CD7913, IGb (immunoglobulin-associated beta), B29, Genbank accession no. NM_000626 or 11038674). Proc. Natl. Acad. Sci. U.S.A. (2003) 100 (7): 4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1;

(16) FcRH2 (IFGP4, IRTA4, SPAP1A (SH2 domain containing phosphatase anchor protein 1a), SPAP1B, SPAP1C, Genbank accession no. NM_030764, AY358130). Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25); Cross-references: MIM:606509; NP_110391.2; NM_030764_1;

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4);

Accession: P04626; EMBL; M11767; AAA35808.1. EMBL; M11761; AAA35808.1;

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2);

Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1;

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1;

(21) Brevican (BCAN, BEHAB, Genbank accession no. AF229053). Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1;

(23) ASLG659 (B7h, Genbank accession no. AX092328). US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: O43653; EMBL; AF043498; AAC39607.1;

(25) GEDA (Genbank accession No. AY260763); AAP14954 lipoma HMGIC fusion-partner-like protein/pid=AAP14954.1—Homo sapien Species: *Homo sapiens* (human) WO2003054152 (claim 20); WO2003000842 (claim 1); WO2003023013 (Example 3, claim 20); US2003194704 (claim 45); Cross-references: GI:30102449; AAP14954.1; AY260763_1;

(26) BAFF-R (B cell-activating factor receptor, BLyS receptor 3, BR3, Genbank accession No. AF116456); BAFF receptor/pid=NP_443177.1—*Homo sapiens*. Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP_443177.1; NM_052945_1; AF132600;

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173:137-146;

WO2003072036 (claim 1; FIG. 1); Cross-references: MIM: 107266; NP_001762.1; NM_001771_1;

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11): 3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1) Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2); Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2), pI: 8.66, MW: 40225 TM: 1 [P] Gene Chromosome: 9p13.3, Genbank accession No. NP_001773.1); WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571; WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962;

NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E,SCA-2,TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (*Xenopus laevis*); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351;

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101;

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors;

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, and a transmembrane domain and a short cytoplasmic tail containing an ITIM motif.

Antibody Derivatives

An antibody provided herein may be further modified to contain additional nonproteinaceous moieties that are known in the art and readily available. The moieties suitable for derivatization of the antibody include but are not limited to water soluble polymers. Non-limiting examples of water soluble polymers include polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Conjugates of an antibody and a non-proteinaceous moiety may be formed by selectively heating by exposure to radiation. The non-proteinaceous moiety of such conjugate may be a carbon nanotube (Kam et al. (2005) Proc. Natl. Acad. Sci. USA 102:11600-605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, (1987) J. Mol. Biol. 196:901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat numbering). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro and Fransson, (2008) Front. Biosci. 13:1619-1633). Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al. (2007) J. Chromatogr. B 848:79-87.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody within a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci.

A "naked antibody" refers to an antibody that is not conjugated to a heterologous moiety (e.g., a cytotoxic moiety) or radiolabel or fluorophore. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

Multispecific Antibodies

An antibody provided herein may be a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In example embodiments, multispecific antibodies are monoclonal antibodies that have binding specificities for at least two different antigen binding sites (such as a bispecific antibody). The first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same molecule. In certain embodiments, the two different epitopes that a multispecific antibody binds are epitopes that are not normally bound at the same time by one monospecific antibody, such as e.g. a conventional antibody or one immunoglobulin single variable domain. The first antigen-binding domain and the second antigen-binding domain of the multispecific antibody may bind epitopes located within two distinct molecules (intermolecular binding). For example, the first antigen-binding domain of the multispecific antibody may bind to one epitope on one molecule, whereas the second antigen-binding domain of the multispecific antibody may bind to another epitope on a different molecule, thereby cross-linking the two molecules.

The antigen-binding domain of a multispecific antibody (such as a bispecific antibody) may comprise two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." A hemimer may comprise a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed below.

A multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both and any other antigen. One of the binding specificities may be for HER2 and the other is for CD3. See, e.g., U.S. Pat. No. 5,821,337. Bispecific antibodies may bind to two different epitopes of the same molecule. Bispecific antibodies may bind to two different epitopes on two different molecules. Bispecific antibodies may also be used to localize cytotoxic agents to cells which express cancer-associated antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation. The term "hole mutation" as used herein refers to a mutation that introduces a cavity (hole) into a polypeptide at an interface in which the polypeptide interacts with another polypeptide. In some embodiments, the other polypeptide has a knob mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, a nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. There can be more than one original and corresponding import residue. The side chain volumes of the various amino residues are shown, for example, in Table 1 of US2011/0287009. A mutation to introduce a "protuberance" may be referred to as a "knob mutation."

Import residues for the formation of a protuberance may be naturally occurring amino acid residues selected from arginine (R), phenylalanine (F), tyrosine (Y) and tryptophan (W). Exemplary import residues are tryptophan or tyrosine. The original residue for the formation of the protuberance may have a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. Import residues for the formation of a cavity may be naturally occurring amino acid residues selected from alanine (A), serine (S), threonine (T) and valine (V). An import residue may be serine, alanine or threonine. The original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

An exemplary knob mutation in an IgG1 constant region is T366W (EU numbering). Exemplary hole mutations in an IgG1 constant region may comprise one or more mutations selected from T366S, L368A and Y407V (EU numbering). An exemplary hole mutation in an IgG1 constant region may comprise T366S, L368A and Y407V (EU numbering).

An exemplary knob mutation in an IgG4 constant region is T366W (EU numbering). An exemplary hole mutation in an IgG4 constant region may comprise one or more mutations selected from T366S, L368A, and Y407V (EU numbering). An exemplary hole mutation in an IgG4 constant region comprises T366S, L368A, and Y407V (EU numbering).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes this disclosure, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See for example, Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (Portolano et al. (1993) J. Immunol. 150:880-887; Clarkson et al. (1991) Nature 352:624-628).

"Tumor-associated antigens" (TAA) are known in the art as provided in the list of exemplary TAAs provided above, and can prepared for use in generating human or humanized antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. Examples of TAA include, but are not limited to, those described in U.S. Pat. Nos. 8,679,767 and 8,541,178, which are expressly incorporated herein.

The antibody components of the ADCs useful in the methods of this disclosure may be produced using recombinant methods and compositions, e.g., as described in U.S. Pat. No. 4,816,567. Isolated nucleic acids encoding such antibodies described herein are provided. Such nucleic acids may encode an amino acid sequence comprising the VL and/or an amino acid sequence comprising the VH of the antibody (e.g., the light and/or heavy chains of the antibody). One or more vectors (e.g., expression vectors) comprising such nucleic acid are also provided. A host cell comprising such nucleic acid is also provided. A host cell may comprise (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. The host cell may be eukaryotic, e.g. a Chinese Hamster Ovary (CHO) cell or lymphoid cell (e.g., Y0, NS0, Sp20 cell). Thus, methods of making an antibody are provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, may be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells. For example, antibodies may be produced in bacteria, in particular when glycosylation and Fc effector function are not needed. For expression of antibody fragments and polypeptides in bacteria, see, e.g., U.S. Pat. Nos. 5,648,237; 5,789,199; 5,840,523; Charlton, Methods in Molecular Biology, Vol. 248 (B. K. C. Lo, ed., Humana Press, Totowa, N.J., (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (Gerngross, (2004) Nat. Biotech. 22:1409-1414; Li et al. (2006) Nat. Biotech. 24:210-215).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (U.S. Pat. Nos. 5,959,177; 6,040,498; 6,420,548; 7,125,978; 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. (1977, J. Gen Virol. 36:59); baby hamster kidney cells (BHK); mouse sertoli cells (TM4 cells as described, e.g., in Mather, (1980) Biol. Reprod. 23:243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al. (1982) Annals N.Y. Acad. Sci. 383:44-68; MRC 5 cells; and FS4 cells. Other useful mammalian host cell lines include Chinese hamster ovary (CHO) cells, including DHFR-CHO cells (Urlaub et al. (1980) Proc. Natl. Acad. Sci. USA 77:4216); and myeloma cell lines such as Y0, NS0 and Sp2/0. A review of certain mammalian host cell lines suitable for antibody production is provided in, e.g., Yazaki and Wu, Methods in Molecular Biology, Vol. 248 (B. K. C. Lo, ed., Humana Press, Totowa, N.J.), pp. 255-268 (2003).

The antibody components of an ADC may be identified, screened for, or characterized for their physical/chemical properties and/or biological activities by various assays known in the art. An antibody may be tested for its antigen binding activity, e.g., by known methods such as ELISA, Western blot, etc. Competition assays may also be used to identify an antibody that competes with another known antibody for binding to antigen. A competing antibody may bind to the same epitope (e.g., a linear or a conformational epitope) that is bound by the known antibody. Detailed exemplary methods for mapping an epitope to which an antibody binds are provided in Morris (1996) "Epitope Mapping Protocols," in Methods in Molecular Biology, Vol. 66 (Humana Press, Totowa, N.J.).

Exemplary antibodies forming the site-specific ADC may include, but are not limited to, trastuzumab, ocrelizumab, pertuzumab, anti-PD1, anti-PD-L1, anti-neuropilin-1, anti-MUC16, rituximab, anti-mesothelin, anti-LY6E, anti-STEAP1, anti-FcRH5, anti-CD22, anti-B7H4, anti-LGR5, anti-CD79b, and anti-Napi2b.

Drug moieties which form the drug component of the ADC may be covalently attached to antibodies through a linker unit to form antibody-drug conjugates for targeted therapeutic effects. An exemplary embodiment of an ADC compound comprises an antibody (Ab) which targets, e.g., a tumor cell, cytotoxic or cytostatic drug moiety (D), and a linker moiety (L) that attaches Ab to D. The antibody is attached through the one or more amino acid residues, such as lysine and cysteine, by the linker moiety (L) to D; the composition having the Formula: Ab-(L-D)$_p$, where p is 1 to about 20, or from about 2 to about 5. The number of drug moieties which may be conjugated via a reactive linker moiety to an antibody molecule may be limited by the number of cysteine residues, including free cysteine residues present in the antibody or which may be introduced by methods described herein, or native cysteines that form the interchain disulfide bonds of the antibody.

The drug moiety (D) of an ADC may include any therapeutic compound, moiety or group, especially a group that has a cytotoxic or cytostatic effect. Exemplary drug moieties may impart such cytotoxic and cytostatic effects by mechanisms including, but not limited to, tubulin binding, DNA binding or intercalation, and inhibition of RNA polymerase, protein synthesis, and topoisomerase. Some cytotoxic drugs tend to be inactive or less active when conjugated to large antibodies or protein receptor ligands. Exemplary drug moieties include, but are not limited to, a peptide (including therapeutic peptides comprising one or more non-natural amino acids, such as cyclic peptides, beta peptides, stables peptides, and cysteine knot peptides), a polyamide, a maytansinoid, dolastatin, auristatin, calicheamicin, pyrrolobenzodiazepine (PBD), PNU-159682, anthracycline, duocarmycin, vinca alkaloid, taxane, trichothecene, CC1065, duocarmycin, camptothecin, elinafide, an antibiotic including a rifamycin or rifamycin-analog, a fluorophore, a radioisotope, and stereoisomers, isosteres, analogs or derivatives thereof, including derivatives of these drugs that have cytotoxic activity.

Fc Region Variants

One or more amino acid modifications may be introduced into the Fc region of an antibody forming a site specific ADC provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat? Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc.

Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

One or more amino acid modifications may be introduced into the Fc portion of the antibody in order to increase IgG binding to the neonatal Fc receptor. The antibody may comprise the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). The YTE mutation does not affect the ability of the antibody to bind to its cognate antigen. The YTE mutation may increase the antibody's serum half-life compared to the native (i.e., non-YTE mutant) antibody. The YTE mutation may increase the serum half-life of the antibody by 2- to 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

The YTE mutant may provide a means to modulate ADCC activity of the antibody. The YTEO mutant may provide a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

The YTE mutant may allow the simultaneous modulation of serum half-life, tissue distribution, and antibody activity (e.g., ADCC of an IgG antibody). See, e.g., U.S. Pat. No. 8,697,650; see also Dall'Acqua et al., Journal of Biological Chemistry (2006) 281(33):23514-24.

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

The proline at position329 (EU numbering) (P329) of a wild-type human Fc region may be substituted with glycine or arginine or an amino acid residue large enough to destroy the proline sandwich within the Fc/Fcγ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

A polypeptide may include the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference). The polypeptide comprising the P329G, L234A and L235A (EU numbering) substitutions may exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference).

The polypeptide comprising an Fc variant of a wildtype human Fc polypeptide may include a triple mutation: an amino acid substitution at position Pro329, a L234A and a L235A mutation according to EU numbering (P329/LALA) (U.S. Pat. No. 8,969,526 which is incorporated by reference). In example embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

An antibody variant may include an Fc region with one or more amino acid substitutions which improve ADCC, e.g., substitutions at positions 298, 333, and/or 334 of the Fc region (EU numbering).

Alterations may be made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (2000) *J. Immunol.* 164: 4178-4184.

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, *Nature* 322:738-40 (1988); U.S. Pat. Nos. 5,648,260; 5,624,821; and WO 94/29351 concerning other examples of Fc region variants.

Cysteine Engineered Antibody Variants

It may be desirable to create cysteine engineered antibodies, e.g., "THIOMAB™ (Genentech, Inc.) antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug intermediates, to create an immunoconjugate, as described further herein. In certain embodiments, any one or more of the following residues may be substituted with cysteine: V205 (Kabat numbering) of the light chain; A140 (EU numbering) of the heavy chain; L174 (EU numbering) of the heavy chain; Y373 (EU numbering) of the heavy chain; K149 (Kabat numbering) of the light chain; A118 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. Nos. 7,521,541; 9,000,130.

The antibody may comprise one of the following heavy chain cysteine substitutions:

| Chain (HC/LC) | Residue | EU Mutation Site # | Kabat Mutation Site # |
|---|---|---|---|
| HC | A | 118 | 114 |
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

The antibody may comprise one of the following light chain cysteine substitutions:

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | C | 205 | 205 |

Linkers

A "Linker" (L) is a bifunctional or multifunctional moiety that can be used to link one or more drug moieties (D) to an antibody (Ab) to form an ADC of Formula I. In some embodiments, ADC can be prepared using a Linker having reactive functionalities for covalently attaching to the drug and to the antibody. For example, in some embodiments, the cysteine thiol of a cysteine-engineered antibody (Ab) can form a bond with a reactive functional group of a linker or a drug-linker intermediate to make an ADC.

A linker may have functionality that is capable of reacting with a free cysteine present on an antibody to form a covalent disulfide bond (See, e.g., the conjugation method at page 766 of Klussman, et al (2004), *Bioconjugate Chemistry* 15(4):765-773, and the Examples herein).

Exemplary spacer components include valine-citrulline ("val-cit" or "vc"), alanine-phenylalanine ("ala-phe"), and p-aminobenzyloxycarbonyl (a "PAB"). Various linker components are known in the art.

A linker may have a functionality that is capable of reacting with a free cysteine present on an antibody to form a covalent bond. Nonlimiting exemplary such reactive functionalities include maleimide, haloacetamides, a-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

A linker may have a functionality that is capable of reacting with an electrophilic group present on an antibody. Exemplary such electrophilic groups include, but are not limited to, aldehyde and ketone carbonyl groups. A heteroatom of the reactive functionality of the linker can react with an electrophilic group on an antibody and form a covalent bond to an antibody unit. Nonlimiting examples of such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

A linker may comprise one or more spacer units between the disulfide group and the drug moiety. An example includes a linker having the following formula -A$_a$-W$_w$-Y$_y$- wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

A linker component may include a "stretcher unit" that links an antibody to another linker component or to a drug moiety. Exemplary stretcher units are shown below (wherein the wavy line indicates sites of covalent attachment to an antibody, drug, or additional linker components):

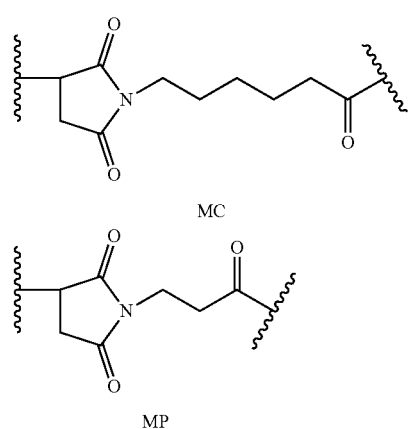

MC

MP

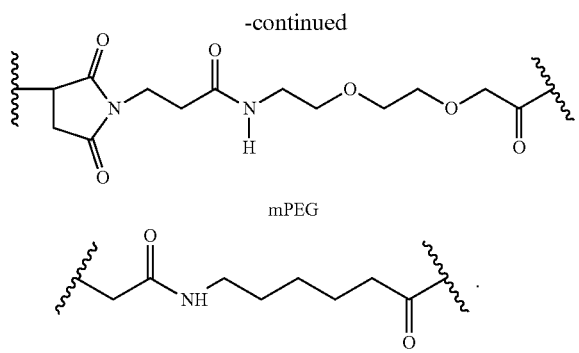

mPEG

The linker may be a peptidomimetic linker such as those described in WO2015/095227, WO2015/095124 or WO2015/095223, which documents are hereby incorporated by reference.

Drug Moieties

The site specific ADC compounds of the invention comprise an antibody conjugated to one or more drug moieties, including the following:

Maytansine and Maytansinoids

In some embodiments, an ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256, 746; 4,260,608; 4,265,814; 4,294,757; 4,307,016; 4,308, 268; 4,308,269; 4,309,428; 4,313,946; 4,315,929; 4,317, 821; 4,322,348; 4,331,598; 4,361,650; 4,364,866; 4,424, 219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) Proc. Natl. Acad. Sci. U.S.A. 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424, 219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.

Maytansinoid drug moieties include those having the structure:

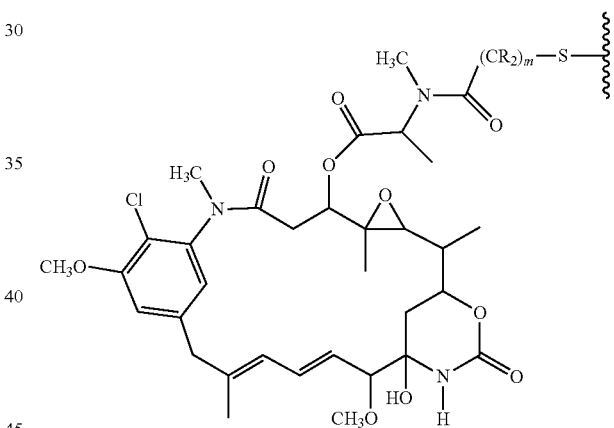

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) *J. Med. Chem.* 49:4392-4408, which are incorporated by reference in their entirety).

In some embodiments, the maytansinoid drug moiety has the following stereochemistry:

Exemplary embodiments of maytansinoid drug moieties include, but are not limited to, DM1; DM3; and DM4, having the structures:

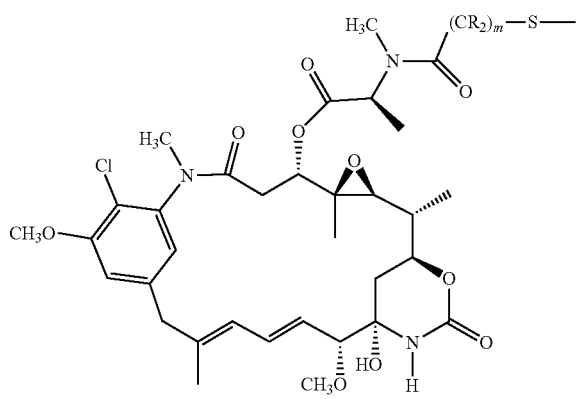

DM1

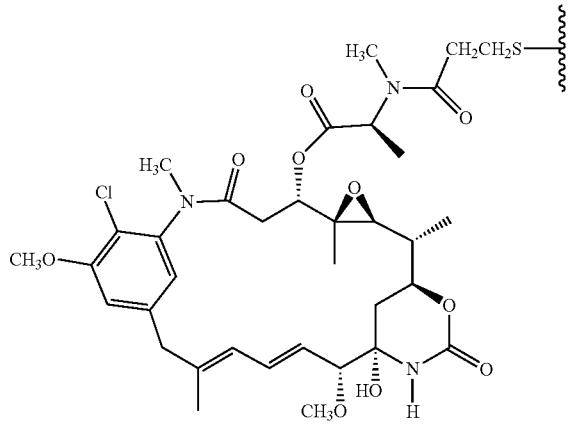

DM3

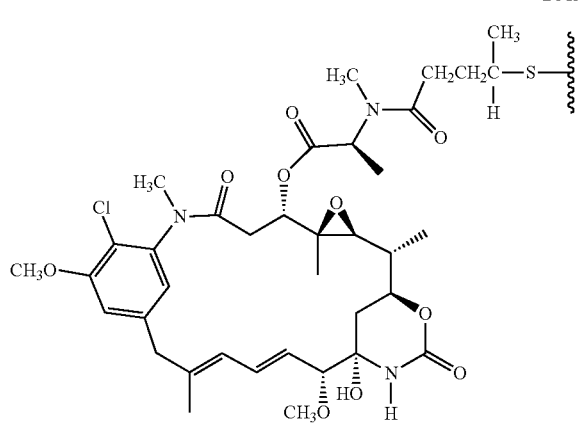

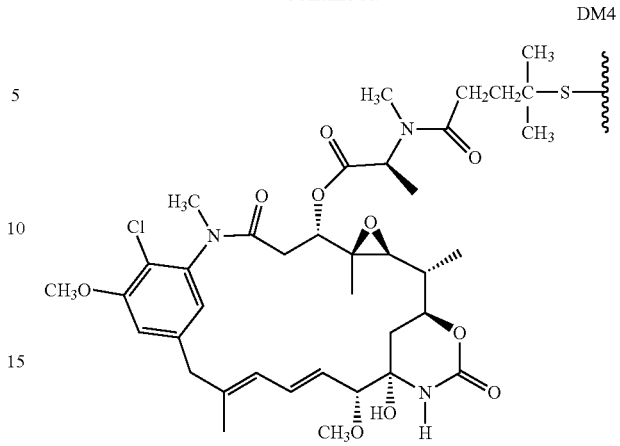

DM4 wherein the wavy line indicates the covalent attachment of the sulfur atom of the drug to a linker (L) of an antibody-drug conjugate.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

Antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). ADCs with an average of 3-4 maytansinoid molecules conjugated per antibody molecule have shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0425235; Chari et al. *Cancer Research* 52:127-131 (1992); US 2005/0276812; and US 2005/016993, the disclosures of which are hereby expressly incorporated by reference.

Auristatins and Dolastatins

Drug moieties may include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties disclosed in U.S. Pat. Nos. 7,498,298 and 7,659,241, the disclosures of which are expressly incorporated by reference in their entirety:

An exemplary auristatin embodiment of formula $D_E$ is MMAE, wherein the wavy line indicates the covalent attachment to a linker (L) of an antibody-drug conjugate:

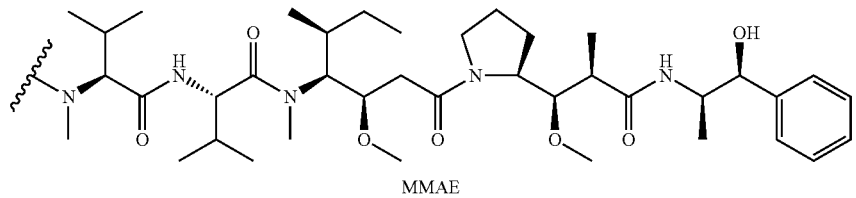 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate:

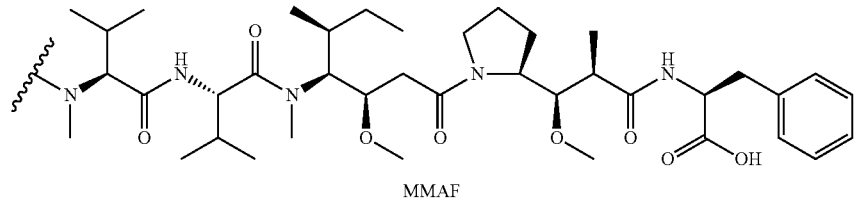

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 1 5:859-863; and Doronina (2003) *Nat. Biotechnol.* 21(7):778-784.

Auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

Calicheamicin

The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; 5,767,285; and WO 2017/068511.

The drug moiety conjugated to the antibody is a calicheamicin compound having the formula:

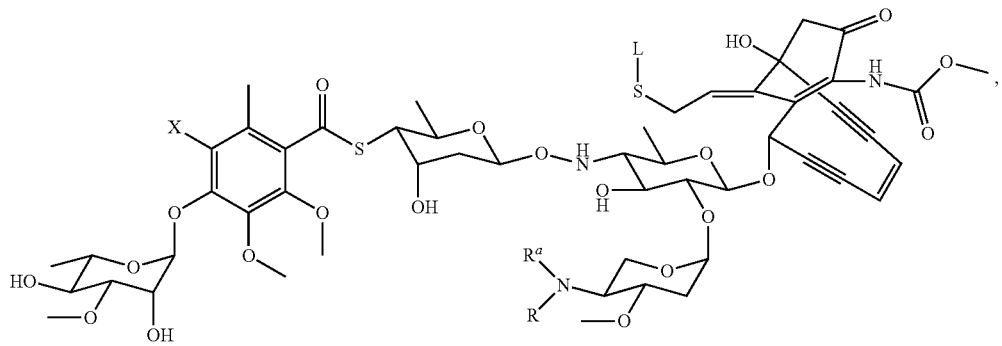

wherein X is Br or I; L is a linker; R is hydrogen, $C_{1-6}$ alkyl, or —C(=O)$C_{1-6}$ alkyl; and $R^a$ is hydrogen or C1-6 alkyl.

Pyrrolobenzodiazepine

An ADC may comprise a pyrrolobenzodiazepine (PBD) drug moiety. PDB dimers may recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7): 2927-2941; Howard et al (2009) *Bioorganic and Med. Chem. Letters* 19(22):6463-6466).

PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

A linker may be attached at one of various sites of the PBD dimer drug moiety, including the N10 imine of the B ring, the C-2 endo/exo position of the C ring, or the tether unit linking the A rings (see structures C(I) and C(II) below).

In some embodiments, an exemplary PBD dimer component of an ADC has the structure of Formula A-1:

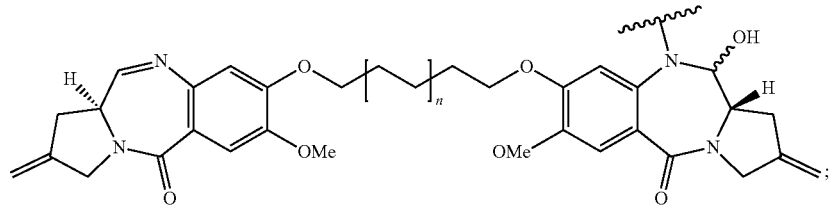

A-1 wherein n is 0 or 1.

In some embodiments, an exemplary PBD dimer component of an ADC has the structure of Formula A-2:

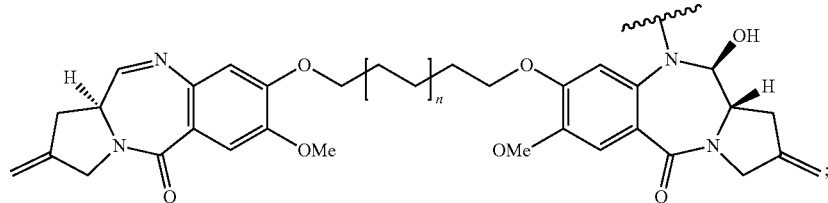

A-2 wherein n is 0 or 1.

In some embodiments, an exemplary PBD dimer component of an ADC has the structure of Formula A-3:

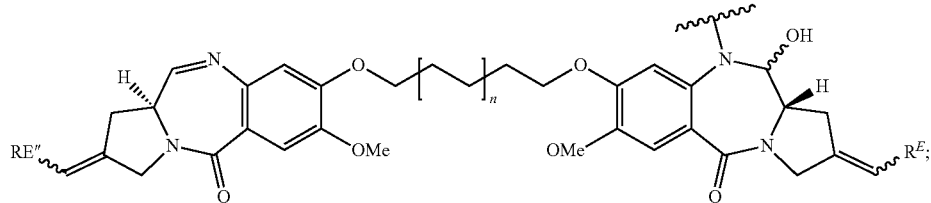

A-3 wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A-4:

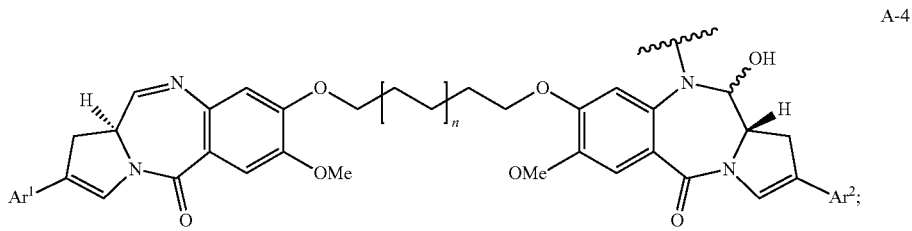

A-4 wherein $Ar^1$ and $Ar^2$ are each independently optionally substituted $C_{5-20}$ aryl; wherein $Ar^1$ and $Ar^2$ may be the same or different; and wherein n is 0 or 1.

An exemplary PBD dimer component of an ADC has the structure of Formula A-5:

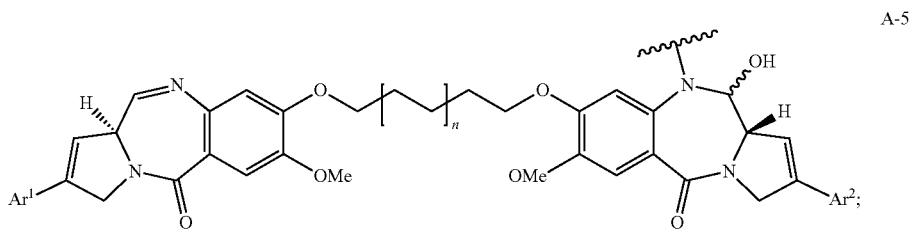

A-5 wherein $Ar^1$ and $Ar^2$ are each independently optionally substituted $C_{5-20}$ aryl; wherein $Ar^1$ and $Ar^2$ may be the same or different; and wherein n is 0 or 1.

$Ar^1$ and $Ar^2$ may each, independently, be selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

An exemplary PBD dimer component of an ADC has the structure of Formula A-6:

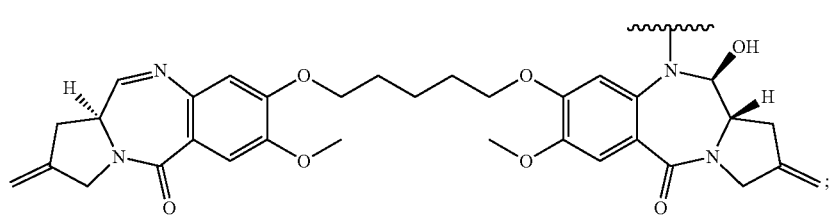

A-6

Further nonlimiting exemplary PBD dimer components of ADC have Formula B:

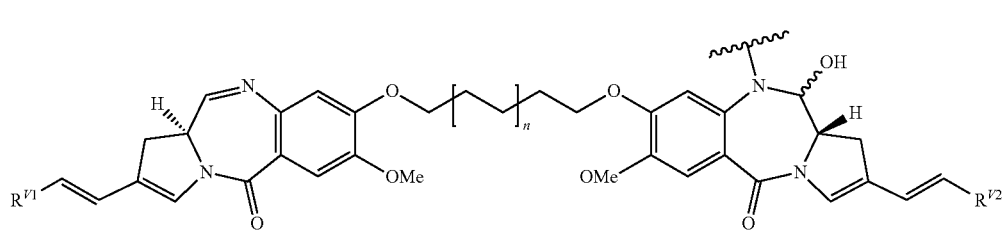

B and salts and solvates thereof, wherein:
the wavy line indicates the covalent attachment site to the linker;
the wavy line connected to the OH indicates the S or R configuration;
$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and
n is 0 or 1.
$R^{V1}$ and $R^{V2}$ may, independently, be selected from H, phenyl, and 4-fluorophenyl.

Nonlimiting exemplary PBD dimer components of ADC include tether-linked Formulas C(I) and C(II):

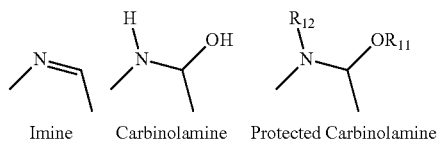

Imine   Carbinolamine   Protected Carbinolamine wherein:
X is $CH_2$ (n=1 to 5), N, or O;
Z and Z' are independently selected from OR and $NR_2$, where R is a primary, secondary or tertiary alkyl chain containing 1 to 5 carbon atoms;
$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$

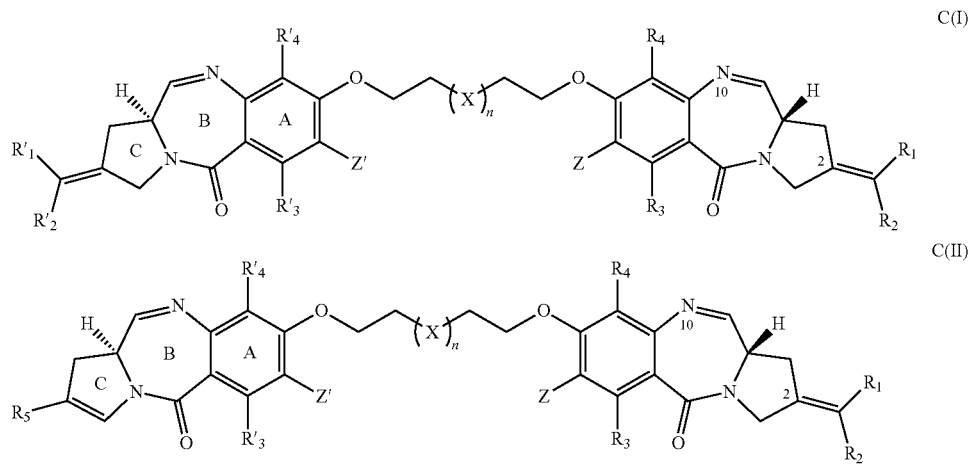

Formulas C(I) and C(II) are shown in their N10-C11 imine form. Exemplary PBD drug moieties also include the carbinolamine and protected carbinolamine forms as well, as shown in the table below:

aryl (including substituted aryls), $C_{5-20}$ heteroaryl groups, $-NH_2$, $-NHMe$, $-OH$, and $-SH$, where, in some embodiments, alkyl, alkenyl and alkynyl chains comprise up to 5 carbon atoms;

R$_3$ and R'$_3$ are independently selected from H, OR, NHR, and NR$_2$, where R is a primary, secondary or tertiary alkyl chain containing 1 to 5 carbon atoms;

R$_4$ and R'$_4$ are independently selected from H, Me, and OMe;

R$_5$ is selected from C$_1$-C$_8$ alkyl, C$_2$-C$_8$ alkenyl, C$_2$-C$_8$ alkynyl, C$_{5-20}$ aryl (including aryls substituted by halo, nitro, cyano, alkoxy, alkyl, heterocyclyl) and C$_{5-20}$ heteroaryl groups, where, in some embodiments, alkyl, alkenyl and alkynyl chains comprise up to 5 carbon atoms;

R$_{11}$ is H, C$_1$-C$_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

R$_{12}$ is H, C$_1$-C8 alkyl, or a protecting group;

wherein a hydrogen of one of R$_1$, R'$_1$, R$_2$, R'$_2$, R$_5$, or R$_{12}$ or a hydrogen of the —OCH$_2$CH$_2$(X)$_n$CH$_2$CH$_2$O— spacer between the A rings is replaced with a bond connected to the linker of the ADC.

An ADC comprising a PBD dimer described herein may be made by conjugating a linker-drug intermediate including a pyridine leaving group via a sulfur atom with a cysteine thiol of an antibody to form a disulfide linkage. Further, in some embodiments, an ADC comprising a PBD dimer described herein may be made by conjugating a linker-drug intermediate including a thiopyridyl leaving group, wherein the pyridine ring is substituted with one or more nitro groups. In some embodiments, the pyridyl ring is monosubstituted with —NO$_2$. In some embodiments, the —NO$_2$ monosubstitution is para relative to the disulfide. In some embodiments, the PBD dimer is connected through the N10 position. For example, non-limiting exemplary ADC comprising a PBD dimer may be made by conjugating a monomethylethyl pyridyl disulfide, N10-linked PBD linker intermediate (shown below) to an antibody:

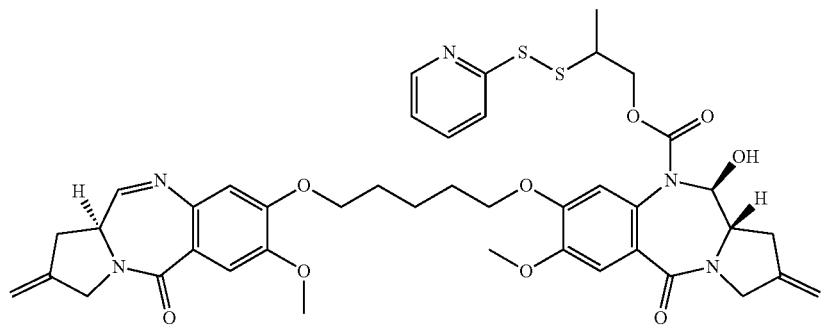

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598; WO 2013/055987.

Anthracyclines

A site specific ADC of this disclosure may comprise an anthracycline. Anthracyclines are antibiotic compounds that exhibit cytotoxic activity. While not intending to be bound by theory, anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status and New Developments* p 11).

Exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) Clinical Cancer Research 11(4):1608-1617). Nemorubicin is a semi synthetic analog of doxorubicin with a 2-methoxymorpholino group on the glycoside amino of doxorubicin and has been under clinical evaluation (Grandi et al (1990) Cancer Treat. Rev. 17:133; Ripamonti et al (1992) Brit. J. Cancer 65:703;), including phase II/III trials for hepatocellular carcinoma (Sun et al (2003) Proceedings of the American Society for Clinical Oncology 22, Abs1448; Quintieri (2003) *Proceedings of the American Association of Cancer Research*, 44:1st Ed, Abs 4649; Pacciarini et al (2006) Jour. Clin. Oncology 24:14116).

In some embodiments, the nemorubicin component of a nemorubicin-containing ADC is PNU-159682.

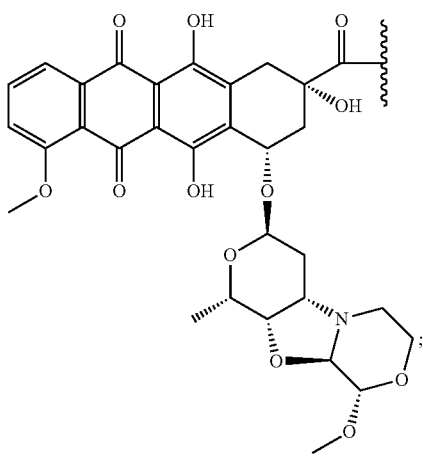 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs may be made by conjugating a pyridyl disulfide PNU amide (shown below) to an antibody:

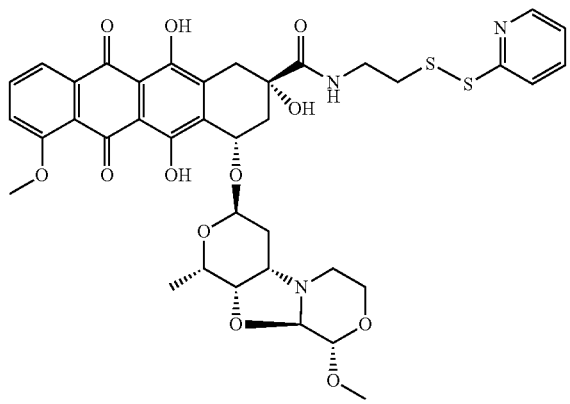 [SMILES: COc1cccc2c1C(=O)c1c(O)c3c(c(O)c1C2=O)C[C@@](O)(C(=O)NCCSSc1ccccn1)C[C@@H]3O[C@H]1C[C@H]2[C@H](O[C@@H]3[C@@H](OC)OCCN32)[C@H](C)O1]

to produce a disulfide-linked PNU-159682 antibody-drug conjugate:

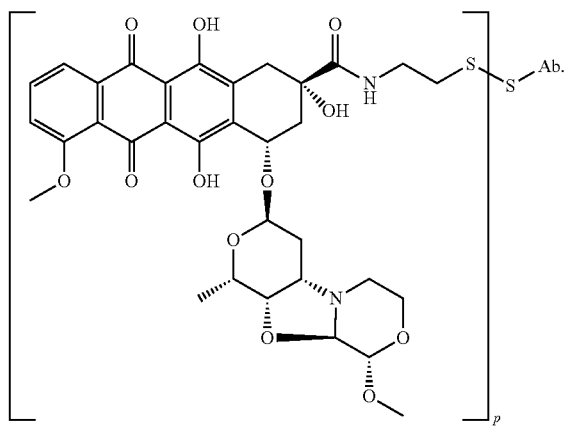

The linker of PNU-159682, maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease-cleavable.

1-(chloromethyl)-2,3-dihydro-1H-benzo[e]indole (CBI) Dimer Drug Moieties

In some embodiments, an ADC comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) *J Med Chem* 46:2132-2151).

A site-specific ADC may comprise a 1-(chloromethyl)-2,3-dihydro-1H-benzo[e]indole (CBI) dimer (WO 2015/023355). The dimer may be a heterodimer wherein one half of the dimer is a CBI moiety and the other half of the dimer is a PBD moiety.

An exemplary CBI dimer comprises the formula:

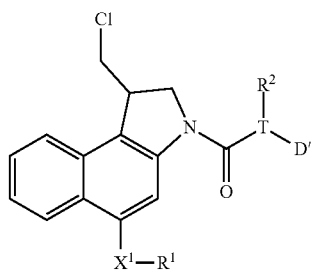

where
$R^1$ is selected from H, $P(O)_3H_2$, $C(O)NR^aR^b$, or a bond to a linker (L);
$R^2$ is selected from H, $P(O)_3H_2$, $C(O)NR^aR^b$, or a bond to a linker (L);
$R^a$ and $R^b$ are independently selected from H and $C_1$-$C_6$ alkyl optionally substituted with one or more F, or $R^a$ and $R^b$ form a five or six membered heterocyclyl group;
T is a tether group selected from $C_3$-$C_{12}$ alkylene, Y, ($C_1$-$C_6$ alkylene)-Y-($C_1$-$C_6$ alkylene), ($C_1$-$C_6$ alkylene)-Y-($C_1$-$C_6$ alkylene)-Y-($C_1$-$C_6$ alkylene), ($C_2$-$C_6$ alkenylene)-Y-($C_2$-$C_6$ alkenylene), and ($C_2$-$C_6$ alkynylene)-Y-($C_2$-$C_6$ alkynylene);
where Y is independently selected from O, S, NR', aryl, and heteroaryl;
where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;
or alkylene, alkenylene, aryl, and heteroaryl are independently and optionally substituted with a bond to L;

D' is a drug moiety selected from:

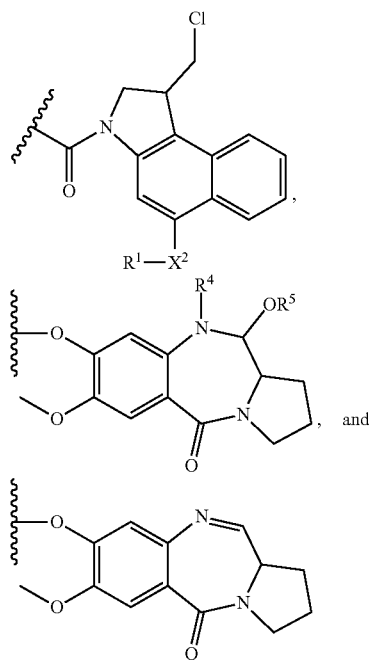

where the wavy line indicates the site of attachment to T; $X^1$ and $X^2$ are independently selected from O and $NR^3$, where $R^3$ is selected from H and $C_1$-$C_6$ alkyl optionally substituted with one or more F;
$R^4$ is H, $CO_2R$, or a bond to a linker (L), where R is $C_1$-$C_6$ alkyl or benzyl; and
$R^5$ is H or $C_1$-$C_6$ alkyl.

Amatoxin and Amanitin

The site specific ADCs may comprise one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. The one or more amatoxin molecules may be a-amanitin molecules.

Other Drug Moieties

Drug moieties may also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232. Drug moieties may also include compounds with nucleolytic activity (e.g., a ribonuclease or a DNA endonuclease).

It is to be understood that where more than one nucleophilic group reacts with a drug-linker intermediate or linker reagent, the resulting product is a mixture of ADC compounds with a distribution of one or more drug moieties attached to an antibody.

Linker-drug intermediates may be prepared by coupling a drug moiety with a linker reagent, and according to the procedures of WO 2013/055987; WO 2015/023355; WO 2010/009124; WO 2015/095227, and conjugated with a protein, including cysteine engineered antibodies, described herein.

Methods of Analyzing and Quantifying Antibody and Drug Moieties in Site Specific ADCs ADCs are targeted anti-cancer therapeutics designed to reduce nonspecific toxicities and increase efficacy relative to conventional small molecule and antibody cancer chemotherapy. They employ the powerful targeting ability of monoclonal antibodies to specifically deliver highly potent, conjugated small molecule therapeutics to a cancer cell. To evaluate properties such as efficacy, stability, homology, pharmacokinetics and toxicity of these ADCs, it is useful to accurately characterize and quantify the antibody component and drug moiety from solution, plasma, urine, and other biological samples, via sample analytical analyses.

This disclosure provides reproducible, accurate, and efficient analytical methods for quantification and analysis of characteristics of antibody and drug components of site specific ADC therapeutic constructs. FIG. 2 shows a cartoon of the work flow in an ADC sample assay of this disclosure, including the optional affinity capture of an ADC from a sample, site specific enzymatic digestion, which may include drug cleavage and release from the ADC, and subsequent analysis of the drug and peptide fragments by chromatography and/or spectrometry methods.

In these methods, the site specific ADC construct is digested with one or more specific enzymes to form a digested ADC composition containing at least one peptide fragment that is not linked to the drug moiety, and at least one peptide fragment that is linked to the drug moiety. Either one or both of the drug and digested antibody component(s)/fragment are then analyzed by chromatography/spectrometry to determine characteristics of the ADC, which may include, but are not limited to, the protein concentration of the ADC composition, the total antibody concentration of the ADC, the drug concentration and/or the average DAR of the ADC, ADC metabolite or catabolite structures, and the extinction coefficient of the ADC.

The protein component of the ADC sample may be digested with a proteolytic enzyme such as an IdeS protease, an IdeZ protease, an IgdE protease, a SpeB protease, a gingipain protease, an endoglycosidase, and combinations of these enzymes.

IdeS is an extracellular cysteine proteinase produced by *S. pyogenes* and available commercially from Promega (Madison, Wis.) and Genovis AB (Cambridge, Mass.). This enzyme, designated IdeS for Immunoglobulin G-degrading enzyme of *S. pyogenes*, cleaves human IgG below the hinge region with a high degree of specificity yielding a homogenous pool of F(ab')2 and Fc fragments. Thus, other human proteins, including immunoglobulins M, A, D and E, are not digested by IdeS. The enzyme efficiently cleaves IgG antibodies bound to streptococcal surface structures, thereby inhibiting the killing of *S. pyogenes* by phagocytic cells, leading to identification of this enzyme as a determinant of bacterial virulence, and a potential therapeutic target (von Pawel-Rammingen, et al. EMBO J. (2002) 21(7):1607-15). The proteolytic cleavage site of the IdeS enzyme is shown in the following table:

| IgG Species and Subclasses | IdeS cleavage site | SEQ ID No. |
|---|---|---|
| Human IgG1 | ... CPAPELLG/GPSVF ... | 1 |
| Human IgG2 | ... CPAPPVA/GPSVF ... | 2 |
| Human IgG3 | ... CPAPPVA/GPSVF ... | 2 |
| Human IgG4 | ... CPAPPVA/GPSVF ... | 2 |
| Mouse IgG1 | Does not cut | |
| Mouse IgG2a | ... CPAPPVA/GPSVF ... | 2 |
| Mouse IgG2b | Does not cut | |
| Mouse IgG3 | ... CPAPPVA/GPSVF ... | 2 |
| Rat IgG2b | ... CPAPPVA/GPSVF ... | 2 |
| Rhesus Monkey | ... CPAPPVA/GPSVF ... | 2 |
| Rabbit | ... CPAPPVA/GPSVF ... | 2 |

HTCPPCPAPELLGGPSVF    SEQ ID NO.: 1

HTCPPCPAPPVAGPSVF    SEQ ID NO.: 2

IdeZ Protease (IgG-specific) is an antibody-specific protease cloned from *Streptococcus equi* subspecies *zooepidemicus* that recognizes all human, sheep, monkey, and rabbit IgG subclasses, specifically cleaving at a single recognition site below the hinge region, yielding a homogenous pool of F(ab')2 and Fc fragments, and is commercially available from New England Biolabs (Ipswich, Mass.), Promega (Madison, Wis.), and Genovis AB (Cambridge, Mass.). IdeZ Protease has significantly improved activity against mouse IgG2a and IgG3 subclasses compared to the IdeS Protease.

IgdE is a protease of *Streptococcus suis* that exclusively targets porcine IgG. This enzyme, designated IgdE for immunoglobulin G-degrading enzyme of *S. suis*, is a cysteine protease distinct from streptococcal immunoglobulin degrading proteases of the IdeS family and cleaves the hinge region of porcine IgG with a high degree of specificity (Spoerry, et al., J Biol Chem. (2016) 291(15):7915-25).

SpeB is a cysteine protease isolated from *Streptococcus pyogenes*, which degrades IgA, IgM, IgE, and IgD, and cleaves IgG antibodies in the hinge region after reduction, i.e., cleaves IgG molecules in a reduced state, e.g., in the presence of dithiothreitol (DTT), (3-mercaptoethanol, or L-cysteine (Persson, et al., Infect. Immun. (2013) 81(6): 2236-41).

Gingipain Kgp (also referred to as Lys-gingipain) is a cysteine protease secreted by *Porphyromonas gingivalis*, which cleaves human IgG1 in the upper hinge region (between K223 and T224) fragments under mild reducing conditions, producing a homogenous pool of Fab and Fc. A recombinant form of Gingipain Kgp is commercially available from Genovis AB (Cambridge, Mass.).

Endoglycosidases represent a family of enzymes expressed by *Streptococcus pyogenes* capable of releasing the terminal sialic acid residues from glycoproteins such as immunoglobulins, and Asp279 of IgG in particular. EndoS is a specific endoglycosidase used to deglycosylate antibodies. Additional endoglycosidases that may be useful in the methods of this disclosure include one or more of Endo S2, EndoH, EndoA, EndoM, EndoF, EndoF1, EndoF2, and EndoF3. Endoglycosidases may be used in the assays of this disclosure in combination with one or more of the proteases described above in preparation of the digested site specific ADC for chromatographic/spectrometric analysis.

The proteolytic enzyme(s) used to digest the site specific ADC construct may be chosen to produce a unique peptide fragment for detection and quantitation. One or more of the peptide fragments unique to the antibody of the ADC is detected and quantified, thereby eliminating background or non-specific proteins or other contaminants that may be present in the analysis sample applied to the chromatography or spectrometry, that do not form part of the ADC.

In example embodiments, the ADC sample is not digested with trypsin, papain, pepsin, endoproteinase LysC, endoproteinase ArgC, *Staph aureus* V8, chymotrypsin, Asp-N, Asn-C, PNGaseF, endoproteinase GluC, LysN, or any combinations of these enzymes. Thus, in example embodiments, the ADC sample, in the digestion or analysis procedures, contains no detectable amounts of trypsin, papain, pepsin, endoproteinase LysC, endoproteinase ArgC, *Staph aureus* V8, chymotrypsin, Asp-N, Asn-C, PNGaseF, endoproteinase GluC, or LysN.

Depending upon the identity of the linker component of the ADC and the chemical treatment applied to reduce, denature, and/or digest the protein component of the sample, the drug moiety of the ADC may be cleaved from the antibody/peptide component of the ADC and may therefore be detected and quantified as an unconjugated drug component in the LC-MS/MS analysis.

Alternatively, or additionally, the drug moiety component of the ADC may remain linked to the antibody/peptide component of the ADC following reduction and denaturation of the ADC, and may therefore be detected and quantified as a peptide-bound drug moiety in the analysis.

The sample containing the ADC for analysis/quantification may be subjected to digestion (and optionally reduction and/or denaturation) without any preliminary sample clean up or enrichment (i.e., "direct digestion" of the sample). Alternatively, or additionally, the sample containing the ADC may be enriched or concentrated for further analysis, prior to digestion. Such concentration of low-abundance peptides or drugs may include enrichment techniques such as size exclusion chromatography, dialysis, selective precipitation, differential centrifugation, filtration, gel electrophoresis, liquid chromatography, reversed-phase phase chromatography, immunoprecipitation, SPINTRAP™ (Cytiva, Inc.) spin columns including protein A and protein G, NHS and streptavidin iron or phosphorus or immobilized antibodies or lectin, paramagnetic beads, immuno-depletion, fractionation, solid phase extraction, phosphopeptide enrichment, polyacrylamide gel electrophoresis, desalting, and the like.

The ADC may be reduced by contact with a composition that includes at least one reductant, for example dithiothreitol (DTT), 2-mercaptoethanol, or tris(2-carboxyethyl)phosphine (TCEP). The ADC may also be denatured by contact with a composition that includes at least one denaturant, for example formamide, dimethylformamide, acetonitrile, SDS, urea, guanidine, sodium 3-((1-(furan-2-yl)undecyloxy)carbonylamino)propane-1-sulfonate (ProteaseMax™), and/or an acid labile surfactant(s) such as those containing a dioxolane or dioxane functional group, such as RapiGest™-SF-surfactant (as described in U.S. Pat. Nos. 7,229,539 and 8,580,533; which are incorporated herein by reference). The ADC may be simultaneously reduced and denatured by contact with a composition that includes at least one reductant and at least one denaturant. Such compositions may include additional solvents, buffers and/or pH modifying agents, such as acetonitrile, methanol, ethanol, HCl, ammonium bicarbonate, ammonium acetate, and/or formic acid, dephosphorylating agents including phosphatases such as calf intestinal alkaline phosphatase, bovine intestinal alkaline phosphatase, or lambda protein phosphatase.

The ADC presented for analysis may also be present in a solution or suspension, such as a pharmaceutical composition formulated for administration to an animal or human, or in cell culture or supernatant that may be present in a production step of the ADC, or in a biological sample obtained from an animal or a human. Thus, the ADC may be present in a matrix selected from a buffer, whole blood, serum, plasma, cerebrospinal fluid, saliva, urine, lymph, bile, feces, sweat, vitreous, tears, and tissue. Biological samples that are frequently presented for analysis of various safety, efficacy and pharmacokinetic/biodistribution parameters of ADCs include human, cynomolgus monkey, rat, and mouse plasma and tissue samples, as well as biological samples from other non-human species.

When presented as part of such biological samples, the ADC may be contacted with an affinity capture media. Affinity capture is a widely used method to enrich/isolate intact proteins, to identify binding partners and protein complexes, or to investigate post-translational modifications. The protein or protein complexes may be separated by non-specific means (e.g., gel electrophoresis, Protein A or G media, type 1 antineuronal nuclear autoantibody (ANNA-1, also known as "anti-Hu"), or specific means (e.g., extracellular domain (ECD) antibodies, or anti-idiotypic antibodies). The ADC may then be eluted from the affinity capture media as a means of sample cleanup prior to digestion (optionally including reduction and/or denaturation), and subsequent chromatography/spectrometry analysis of the digest.

Alternatively, or additionally, the ADC sample is analyzed with an affinity capture by bead- or resin-supported Protein A/G, followed by on-bead digestion (which may include proteolysis, deglycosylation, dephosphorylation, reduction, and/or denaturation) prior to elution of an enriched, digested antibody sample from the affinity capture media, and subsequent chromatography/spectrometry analysis. Methods to detect and screen antibody-drug conjugates by Immunoaffinity membrane (IAM) capture and mass spectrometry have been disclosed (U.S. Pat. No. 7,662,936), including bead-based affinity capture methods (U.S. Pat. No. 8,541,178).

The analysis sample(s) (or at least a portion thereof) comprising one or both of the drug (or peptide-linker-drug) and the digested antibody components of the site specific ADC is then applied to a detection methodology that may include high performance liquid chromatography (HPLC), reverse-phase liquid chromatography (RP-LC), mass spectrometry (MS) or tandem mass spectrometry (MS/MS), RP-LC/MS and LC-MS/MS, to detect and quantify both the drug and antibody component of the ADC.

Mass spectrometry may be used to establish the mass to charge ratio of at least one peptide fragment of the digested antibody, and/or the mass to charge ratio of the drug (or peptide-linker-drug) moiety of the ADC.

The molar extinction coefficient (or mass attenuation coefficient) is equal to the molar attenuation coefficient times the molar mass. The molar extinction coefficient of a protein at 280 nm depends almost exclusively on the number of aromatic residues, particularly tryptophan, and can be predicted from the sequence of amino acids. Thus, if the molar extinction coefficient is known, it can be used to determine the concentration of the protein in solution.

Each publication or patent cited herein is incorporated herein by reference in its entirety.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Materials. Human lithium heparin plasma was purchased from BioreclamationIVT (New York, U.S.A.). Streptavidin-coated Dynabeads M-280 were purchased from Invitrogen (CA, U.S.A.). IdeS, i.e. FabRICATOR, was purchased from Genovis, Inc. (Cambridge, Mass.). Other reagents included HBS-EP buffer containing 0.01 M HEPES, pH 7.4, 0.15 M NaCl, 3 mM EDTA, 0.005% Polysorbate 20 (GE Healthcare; Little Chalfont, U.K.) and the peptide N-glycosidase F (PNGase F; ProZyme; CA, U.S.A.). All TDCs and specific ADC capture reagents, for example, ECD, were produced at Genentech (South San Francisco, Calif., U.S.A.). ECD was biotinylated with a 10 mol equiv of Sulfo-NHS-LC-biotin (Pierce/Thermo Fisher Scientific, Rockford, Ill., U.S.A.) to ECD for 60 min at room temperature in 10 mM sodium phosphate/150 mM NaCl, pH 7.8. Excess unbound biotin was removed using Zeba spin desalting column (Pierce/Thermo Fisher Scientific), as per the manufacturer's protocol. Biotinylated ECD concentration was determined spectrophotometrically by measuring the absorbance at 280 nm using GeneQuant 1300 (GE Healthcare).

Animal Plasma Samples. All animal studies were carried out in compliance with National Institutes of Health guidelines for the care and use of laboratory animals and were approved by the Institutional Animal Care and Use Committee at Genentech, Inc. For PK studies, female C.B-17 SCID mice (Charles River Laboratories) were administered a single dose of ADC intravenous bolus injection, and whole blood was drawn from animals via terminal cardiac puncture. Blood samples were collected into tubes containing lithium heparin and were allowed to sit on wet ice until centrifugation (within 15 min of collection). The collected plasma samples were stored at −70° C. until analysis. Plasma samples from Sprague-Dawley rats were obtained in a similar way.

Instrumentation. Affinity capture was carried out on a KingFisher 96 magnetic particle processor (Thermo Electron) using 2 mL square-top 96-deep well plates (Analytical Sales and Service, Pompton Plains, N.J., U.S.A.). The eluate was transferred to a VWR Dynablock 96-well 0.5 mL plate (VWR Scientific Products). Capillary RPLC-MS was carried out on a Waters nanoACQUITY UPLC system (Cambridge, Mass., U.S.A.) coupled to a Sciex TripleTOF® 5600 mass spectrometer (Redwood City, Calif., USA).

Example 1: IdeS (2nd-Generation) Affinity Capture LC-MS Assay Design and Validation The affinity capture LC-MS assay was conducted for site-specific ADCs, including TDCs with conjugation sites in the Fab region (Su' D. et al (2016) Anal. Chem., 88(23): 11340-11346; Xu, K.; et al. (2013) Bioanalysis, 5, 1057-1071; U.S. Pat. No. 8,541,178; Xu, K.; et al Anal. Biochem. (2011) 412:56-66). In order to test and validate the multiplexing assays of this disclosure, IdeS protease (FIG. 1)

removed the glycan-containing Fc region at specific sites, thereby reducing the size of analytes and heterogeneity of ADC catabolites. On-bead digestion using IdeS was expected to quickly generate F(ab')2 (about 100 kDa) for the final LC-MS analysis, instead of the intact ADC (about 150 kDa). The reduced size of analytes and quick digestion offered by IdeS resulted in improved sensitivity and resolution, and minimal artificial drug modification or decomposition and equal recovery of individual DAR species during the enrichment process, compared with a 1st-generation affinity capture LC-MS used to test in vivo stability and PK assessment of TDCs. This 2nd-generation affinity capture LC-MS showed surprising improvements for analyzing DAR and catabolite characterization of site-specific ADCs when tested on a variety of TDCs with different antibodies, linker-drugs, and conjugation sites.

FIG. 2 provides a cartoon illustration of the 2nd-generation LC-MS assay tested in this Example, and FIG. 3 shows a cartoon illustration comparing embodiments of the $1^{st}$ generation and $2^{nd}$ generation assays that were tested and compared in this Example.

In vivo plasma samples were collected from mouse, rat and cynomolgus monkey models that had been administered TDCs intravenously. All animal studies were performed in compliance with NIH guidelines for the care and use of laboratory animals. Plasma was purchased from BioreclamationIVT (New York, USA). All TDCs and specific ADC capture reagents, e.g., extracellular domain (ECD) and anti-human (Fab region) antibody, were produced at Genentech (South San Francisco, Calif., USA). ECD and anti-human (Fab region) antibody were biotinylated with 10 molar equivalent of Sulfo-NHS-LC-biotin (Pierce/Thermo Fisher Scientific, Rockford, Ill., USA) to ECD or anti-human (Fab region) antibody for 60 min at room temperature in 10 mM sodium phosphate/150 mM NaCl, pH 7.8. Excess unbound biotin was removed using ZEBA™ spin desalting column (Pierce/Thermo Fisher Scientific), per manufacturer's protocol. Biotinylated ECD or anti-human (Fab region) antibody concentration was determined spectrophotometrically by measuring absorbance at 280 nm using GENEQUANT™ 1300 (GE Healthcare).

The assay experimental details of the 1st-generation affinity capture LC-MS have been described previously (U.S. Pat. No. 8,541,178 to Kaur et al; Xu, et al., Anal. Biochem. 2011, 412(1):56-66). For comparison testing of the 2nd-generation assay, 100 µL of streptavidin paramagnetic beads (Streptavidin-coated Dynabeads M-280; Invitrogen (CA, USA) were added to a 96-deep-well plate containing an excess amount of biotinylated specific capture reagents, e.g., ECD, in HBS-EP buffer (300 µL; 0.01 M HEPES, pH 7.4, 0.15 M NaCl, 3 mM EDTA, 0.005% P20 (GE Healthcare; Little Chalfont, UK)) and incubated with agitation at room temperature (RT) for 1 h. TDC-containing plasma samples were then added (a maximum amount of 2 µg or 250 µL, whichever is less) to the ECD-immobilized beads to a total volume of 300-500 µL, and incubated with agitation at RT for 1.5 h.

Affinity capture with a generic capture reagent, biotinylated anti-human IgG F(ab')2 antibody is useful for capture for all different humanized therapeutic antibody ADC and is appropriate in a study with different therapeutic arms, or where no specific ECD is available. Results from the 2nd-generation LC-MS assay show that generic anti-human IgG F(ab')2 is similar to specific ECD capture of ADC analytes.

Affinity capture was carried out on a KingFisher 96 magnetic particle processor (Thermo Electron) using 2-mL square-top 96-deep-well plates (Analytical Sales and Service, Pompton Plains, N.J., USA). Elute was transferred to a VWR Dynablock 96 well 0.5 ml plate (VWR Scientific Products). Capillary RPLC-MS was carried out on a Waters nanoACQUITY UPLC (Cambridge, Mass., USA) coupled with AB Sciex 5600 triple time-of-flight (TOF) mass spectrometer (Redwood City, USA).

Affinity captured TDCs were digested with IdeS protease (FABRICATOR™, Genovis AB) (40 units) in HBS-EP buffer (300 µL) at 37° C. for 1 h, in contrast to PNGase F (PROZYME™; CA) digestion for overnight as described in the 1st-generation method. All agitation was carried out carefully, ensuring that beads were well suspended in solution throughout the digestion procedure. Newly-generated F(ab')2 fragments were washed sequentially with HBS-EP buffer, water and 10% ACN on beads, and then eluted by incubation in 50 µL of 30% acetonitrile with 1% formic acid at RT for 10 min. The subsequent F(ab')2 elution was spun in a Bruker centrifuge at 4000 rpm for 10 min at RT and then transferred to a 96-well plate to remove residual beads with a magnet. Final elution was spun at 4000 rpm for 10 min at RT prior to LC-MS to avoid injection of any residual beads. An aliquot of 5 µL of F(ab')2 elution was submitted for LC-MS analysis.

Capillary LC-MS was performed on a TripleTOF 5600 mass spectrometer coupled with a Waters NanoAcquity. On-line desalting and pre-concentration were conducted on a PS-DVB monolithic column (500-µm i.d.×5 cm, Thermo Fisher Scientific, Waltham, Mass.) at 65° C. using a gradient condition at a flow rate of 15 µL/min with mobile phases A, 0.1% formic acid (FA) and B, acetonitrile (ACN) with 0.1% FA. The LC gradient was 0% B (0-4 min), 0-40% B (4-8 min), 40% B (8-11 min), 40-100% B (11-12.5 min), 100% B (12.5-13.5 min), 100-0% B (13.5-14.2 min), 0% B (14.2-15 min). LC flow was diverted to waste for the first 6 min. TripleTOF 5600 was operated with a DuoSpray Ion Source with the following key settings: ion source temperature, 425.0° C.; Ion source gas (GS)1, 40; GS2, 35; Curtain gas, 30; IonSpray Voltage Floating, 5000V; declustering potential, 250; collision energy, 20. Mass spectra were acquired in the intact protein mode, using ANALYST™ TF 1.6. Deconvolution was Performed with BIOANALYST™ 1.5.1. Relative ratios of individual TDC DAR species were obtained based on peak areas in the deconvoluted mass spectra. Calculated results within ±15% were considered not significantly different: Average DAR=Σ (% peak area×number of conjugated drugs)/100.

For method development, direct LC-MS was tested and compared with both 1st-generation, and 2nd-generation, affinity capture LC-MS. Naked antibody (DAR0) and TDC standard (DAR2) were mixed as DAR0:DAR2≈1:1 at a total concentration of 100 µg/mL. An aliquot of 20 µL TDC mixture was spiked into 100 µL of human plasma to a final concentration of 20 µg/mL for the 1st-generation and 2nd-generation affinity capture LC-MS, respectively. Another aliquot of 10 µL TDC mixture was spiked into 50 µL of 30% ACN with 1% FA and directly submitted for LC-MS analysis. DAR profiling by direct LC-MS of TDC mixtures at known ratios allowed determination of whether all individual DARs have similar LC-MS response. For example, if the relative DAR ratios by direct LC-MS are consistent with the theoretical values, there is no significant bias against any individual DAR species in LC recovery and ionization efficiency. Consistency in DAR profiling by affinity capture LC-MS and direct LC-MS would suggest unbiased recovery of individual DAR species during the affinity enrichment process.

Figure 5:
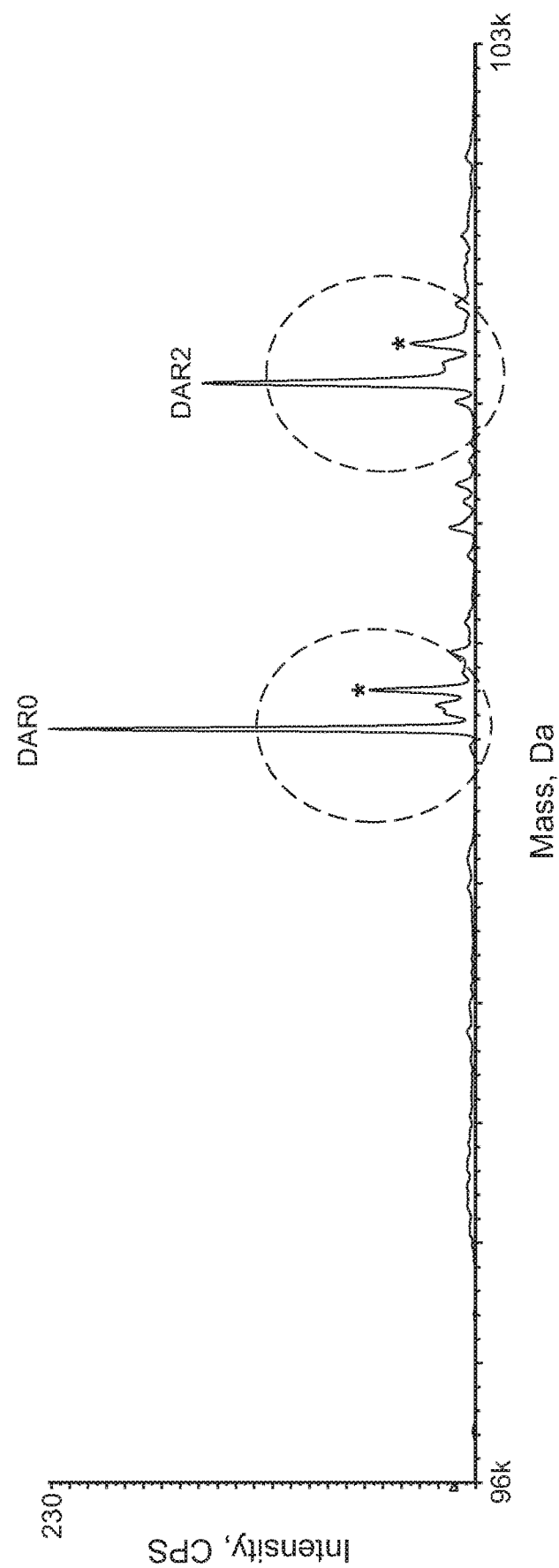
FIG. 5 shows 2nd-generation affinity capture LC-MS analysis of a TDC standard mixture (DAR0:DAR2=1:1). MS peaks labeled with * represent DARs with glycans.

FIGS. 4-6 shows a comparison among direct LC-MS (FIG. 4), 1st-generation (FIG. 5) and 2nd-generation (FIG. 6) affinity capture LC-MS by injecting the same amount of starting TDC standard mixture. The example TDC contains a pyrrolobenzodiazepine dimer (PBD) as the cytotoxic drug payload. Similar retention time and charge envelopes suggested no significant differences in ionization efficiency of different TDC DAR species allowing for semi-quantification using relative ratios of individual DAR species based on their peak areas in the deconvoluted mass spectra. ADC catabolites contained glycations and/or other modifications. There was no significant difference in the relative ratio of DAR0 and DAR2 between direct LC-MS and the 2nd-generation affinity capture LC-MS, indicating unbiased capture of individual DAR species (DAR 0 and DAR2). The 2nd-generation affinity capture method was further tested with a large variety of TDC standards (DAR0 and DAR2) with different antibodies, conjugation sites in the Fab region, linkers (maleimide and disulfide), and toxins (DNA damaging agents including anthracyclines, CBI dimers and PBD dimers, and tubulin binders). Similar ionization efficiency and relative ratios of DAR0 and DAR2 were observed by the direct LC-MS approach, confirming that the 2nd-generation affinity capture LC-MS is applicable to a large variety of Fab site-specific antibody-drug conjugates.

The PNGaseF digestion, 1st-generation, affinity capture LC-MS assay method uses a TDC (THIOMAB™, Genentech, Inc.) antibody drug conjugate) standard mixture that included a cysteine-engineered, anti-MUC16 antibody conjugated to the cytotoxic drug monomethyl auristatin E (MMAE) via a maleimido-caproyl-valine-citrulline-para-amino-benzyloxycarbonyl (MC-vc-PAB) linker. This method was later found to show different response to individual DARs depending on the linker-drugs and antibodies. Measured DAR0:DAR2 was compared with the theoretical value of 1 and was not significantly different with the calculated result within ±15%. The difference of measured DAR0:DAR2 from the theoretical value was pronounced by the 1st-generation and/or IdeS protease-overnight digestion affinity capture LC-MS, indicating that on-bead digestion for long hours (e.g., overnight) caused potential biased recovery of individual DARs during the affinity enrichment step. Reduced and optimized incubation time for ECD immobilization, ADC and ECD binding, and on-bead digestion steps in the 2nd-generation affinity capture LC-MS minimized potential biased capture of different DARs and therefore provided more accurate information on DAR profiling. Thus, the advantages of the 2nd-generation affinity capture LC-MS include:

MS intensity by the 2nd-generation LC-MS (230 cps at maximum) was higher than by theist-generation analysis (48 cps at maximum).

The 2nd-generation affinity capture LC-MS allows detection of TDCs as low as approximately 20 ng (0.2 μg/mL×100 μL).

Adjacent MS peaks are better resolved by the 2nd-generation assay.

More complete removal of glycans is observed with 2nd-generation capture LC-MS.

Compared to deglycosylation by the PNGase F overnight digestion, Fc removal by the IdeS protease is completed within about 1 h, greatly improving the assay efficiency (1 day for the 2nd-generation LC-MS vs. 2 days for theist-generation LC-MS).

Affinity capture LC-MS was specifically designed to identify ADC catabolites, characterize DAR profiles, and thereby understand the fate and PK behaviors of circulating ADCs. It is therefore important to retain ADC integrity throughout the sample preparation process, in order to accurately reflect in vivo biotransformations. However, using the PNGaseF digestion, 1st-generation affinity capture LC-MS assay, ADCs containing labile cytoxic drugs were observed to undergo unintended changes, such as ex vivo payload metabolism after incubation for long hours (FIG. 9). Analysis of a labile TDC, TDC-L2 in rat plasma in vivo by affinity capture LC-MS intact antibody assay (left) and F(ab')2 assay (FIG. 10). Artificial partial drug loss (−PD) resulting from ex vivo payload metabolism was minimized by IdeS digestion at 37° C. for one hour and affinity capture LC-MS F(ab')2 assay. TDC-L2 has a CBI dimer drug moiety and maleimide linker. The production of such artificial ADC catabolites was minimized in the 2nd-generation affinity capture LC-MS (FIG. 10), in which IdeS digestion was complete within 1 h. The reduced digestion time enables minimal unintended changes in ADC integrity, and thus provides more accurate information on ADC biotransformation and PK behaviors in vivo.

Figure 18A:
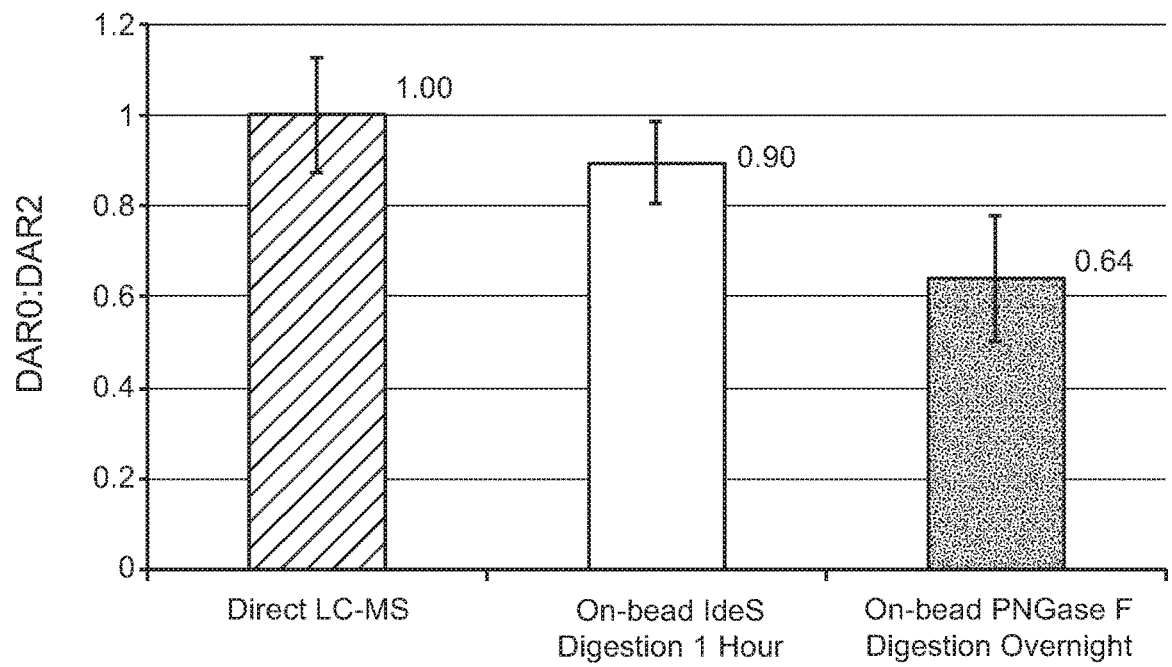
FIG. 18A shows DAR (drug-antibody ratio) profiling a TDC (PBD dimer drug, disulfide linker) standard mixture (DAR0:DAR2=1:1) by direct LC-MS assay, IdeS digestion, affinity capture LC-MS F(ab')2 assay, and PNGaseF affinity capture LC-MS intact antibody assay with a standard deviation of 0.13, 0.09, and 0.14 for 3 replicates, respectively.
Figure 18B:
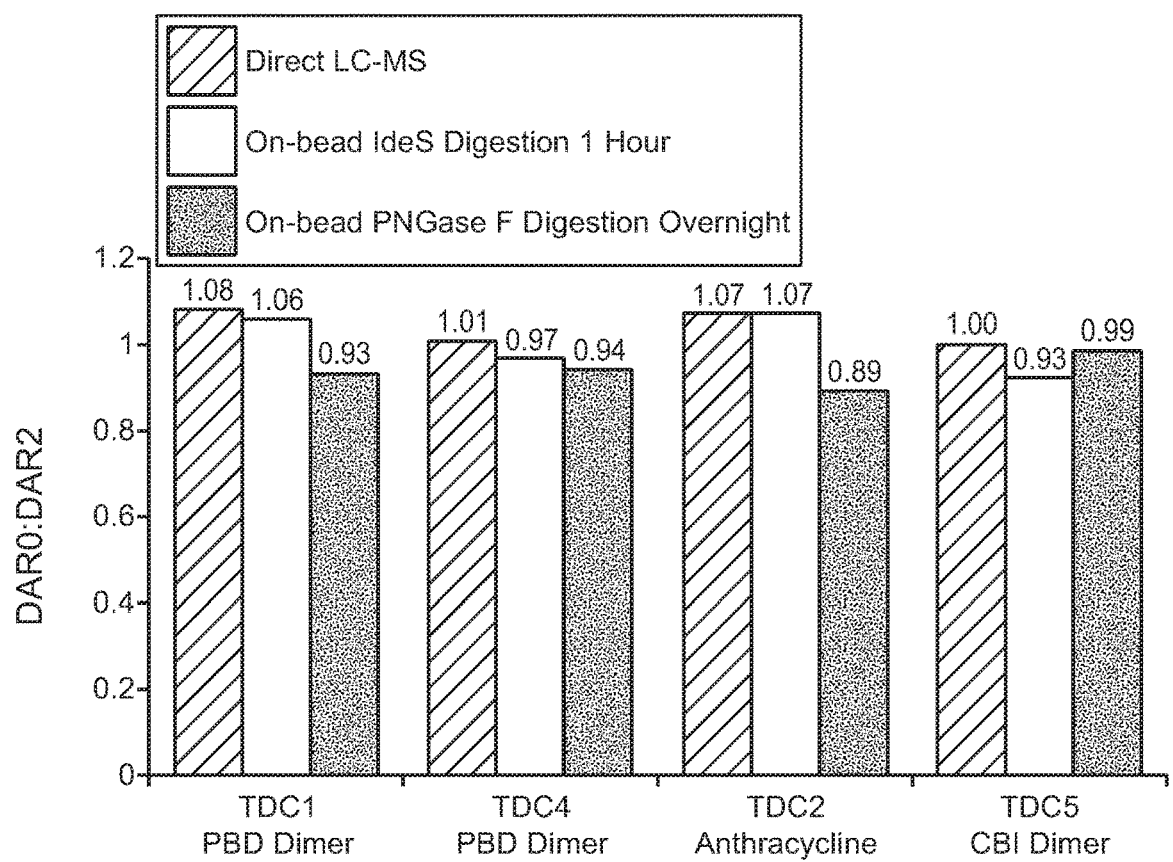
FIG. 18B shows DAR profiling of TDC standard mixtures (DAR0:DAR2=1:1) by direct LC-MS, affinity capture LC-MS F(ab')2 assay with IdeS digestion 1 hour, and affinity capture LC-MS F(ab')2 assay with PNGaseF digestion overnight.

FIG. 18A shows DAR profiling a TDC (PBD dimer drug, disulfide linker) standard mixture (DAR0:DAR2=1:1) by direct LC-MS assay, affinity capture LC-MS F(ab')2 assay, and affinity capture LC-MS intact antibody assay with a standard deviation of 0.13, 0.09, and 0.14 for 3 replicates, respectively. Human plasma (100 μL) containing spiked TDC standard mixture was used for the affinity capture and 5 μL eluent was injected for LC-MS analysis. FIG. 18B shows DAR (drug-antibody ratio) profiling of TDC standard mixtures (DAR0:DAR2=1:1) of TDC with PBD dimer (TDC1 and TDC4), anthracycline (TDC2) and CBI dimer (TDC5) drug moieties covalently attached to cysteine-engineered antibody with a disulfide linker by direct LC-MS, affinity capture LC-MS F(ab')2 assay with IdeS digestion 1 hour, and affinity capture LC-MS F(ab')2 assay with IdeS digestion overnight. Human plasma (100 μL) containing spiked TDC standard mixture was used for the affinity capture and 5 μL elute was injected for LC-MS analysis. The error of measured DAR0:DAR2 for TDC2 was pronounced by the IdeS overnight digestion affinity capture LC-MS, indicating that prolonged on-bead incubation (e.g., overnight digestion) led to potential biased recoveries of different drug-loaded TDC2 species during sample preparation. For instance, in the affinity capture LC-MS F(ab')2 assay, the significantly reduced on-bead digestion time minimized potential biased recoveries of different ADC species and thereby provided more accurate information regarding DAR estimation.

In the analysis of complex ADC catabolites, the adjacent deconvoluted MS peaks need near baseline separation to allow accurate assignment of ADC catabolite structures. FIGS. 7 and 8 show linker-drug deconjugation (−LD) by cleavage of the thiol-maleimide bond. Multiple TDC catabolites were generated in mouse plasma in vivo, due to loss of 42 Da from the drug molecule. Their MS peaks were not resolved by PNGaseF digestion, 1st-generation affinity capture LC-MS (FIG. 7), but were near baseline-resolved by the IdeS digestion, 2nd-generation affinity capture LC-MS (FIG. 8), which enabled confident catabolite identification and more accurate DAR calculation. This accurate information is helpful for understanding the ADC efficacy and toxicity profiles as well as the ADC drug metabolism, which in turn helps to optimize new cytotoxic ADC design, which is focused on new types of antibody platforms, conjugation chemistry, linkers, and drugs. The multiple drug and metabolism parameters that must be verified during the drug development of ADCs and complex catabolites in vivo poses challenges on bioanalytical analysis. For instance, the 1st-generation affinity capture LC-MS, a useful exploratory assay for DAR and catabolite characterization, was found not generally applicable to the next-generation ADCs due to its limited sensitivity, resolution, efficiency and potential biased response to certain DAR species. This PNGaseF digestion, 2nd-generation assay accommodates the low-dose and labile site-specific ADCs becoming predominant in drug development. FIGS. 7 and 8 show characterization of complicated TDC catabolites in mouse plasma in vivo by affinity capture LC-MS intact antibody assay (FIG. 7) vs. affinity capture LC-MS F(ab')2 assay (FIG. 8). Partial drug loss by linker-drug deconjugation (−PD) significantly affected the potency of TDC-L1, leading to the reduction of DAR accordingly The 2nd-generation affinity capture method employed in this comparative example utilized the IdeS protease for deglycosylation by removing the Fc fragments where the majority of glycans are located. The resulting F(ab')2 fragments (about 100 kDa) which retain the linker-drugs, are analyzed by LC-MS, instead of the traditional intact ADCs (about 150 kDa). Compared to deglycosylation by overnight digestion with PNGase F, rapid removal of Fc by on-bead IdeS digestion and the reduced size of the F(ab')2 analytes results in an improved assay with higher sensitivity, resolution, and efficiency, as well as minimal unintended changes to ADC profiles and integrity during sample processing as summarized in the following table:

leads to discovery of new ADC catabolites. The method is applicable to a variety of site-specific ADCs with conjugation sites in the Fab region, and to analysis of conventional ADCs via inter-chain disulfide conjugation.

Example 2: Protein Concentration Determination

An accurate protein concentration determination is essential for evaluating in vitro and in vivo efficacy, as well as toxicity, of protein-drug conjugates. The inventors have developed a method to determine protein concentration for ADCs comprising, for example, small molecule payloads that contribute to the protein's absorbance at 280 nm due to the presence of aromatic rings, and particularly when the extinction coefficient of the small molecule at 280 nm and/or its absorbance maximum are unknown. In this example, the protein concentration was determined independently of the conjugated payload by proteolytic digestion with Immunoglobulin-degrading enzyme of *Streptococcus* pyrogenes (IdeS), and subsequent LC-MS analysis.

Figure 11:
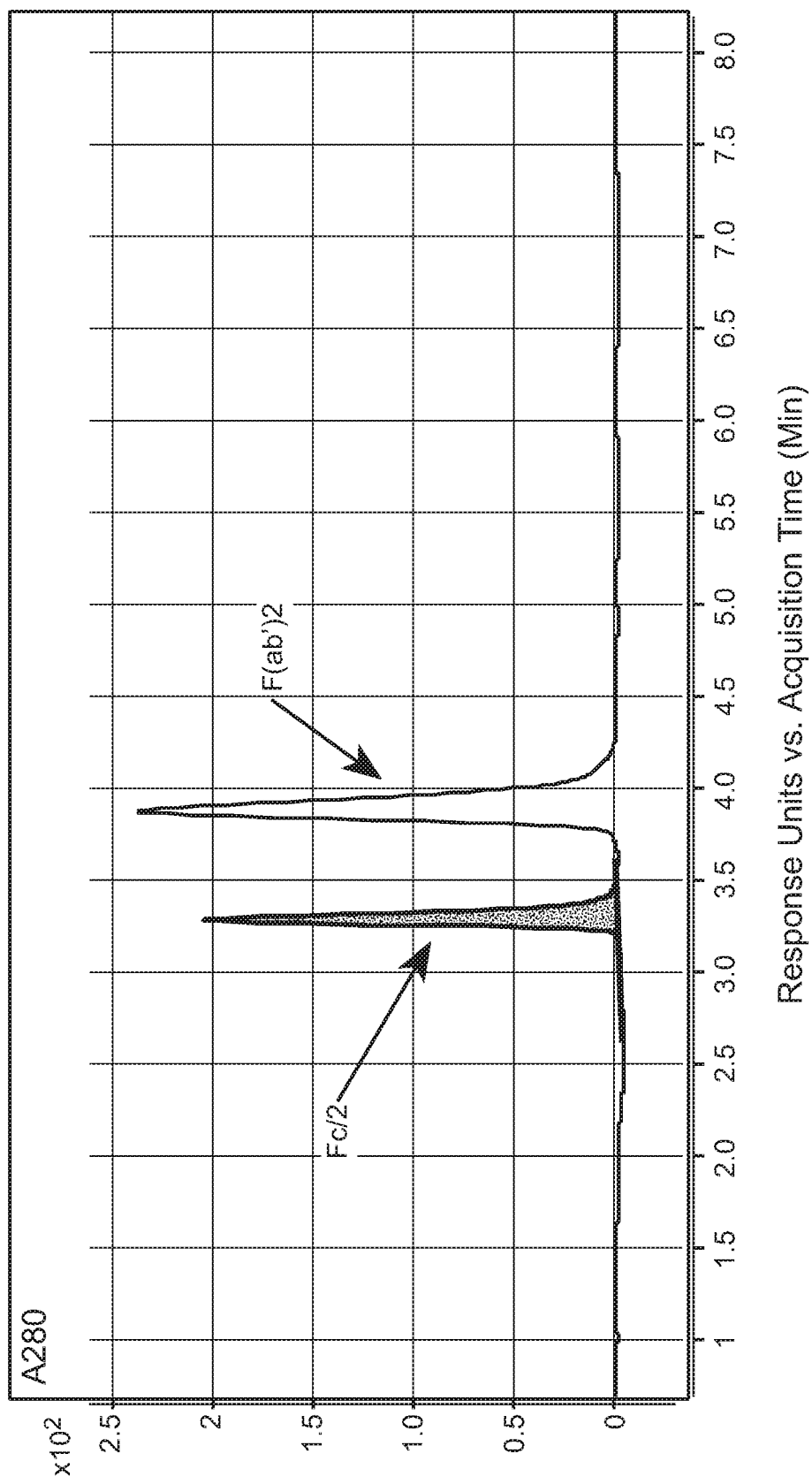
FIG. 11 shows an RP-LCMS analysis of a site-specific ADC digested with the IdeS proteolytic enzyme. The Fc/2 fragment elutes first and base-line resolves from drug containing F(ab')2. The peak area of the antibody fragment that does not contain the linker-drug is then used to calculate protein concentration.

IdeS cleaves human IgG1's with high specificity at a site below the hinge region generating F(ab')2 and Fc fragments (FIG. 1). These species can be chromatographically separated on reversed-phase (FIG. 11). Non-covalent interactions between the two arms of the Fc are disrupted by the acidity and organic solvent concentration of the mobile phases, resulting in an Fc/2 peak of approximately 25 kD in size. In ADCs where the drug payload is conjugated to

TABLE

| Changes and Improvements to the 1st-generation Assay | |
| --- | --- |
| Changes to the Assay | Improvements of the Assay |
| Reduced digestion time from overnight to 1 hr | Increase assay efficiency (2 days to 1 day) |
| Reduced digestion time from overnight to 1 hr | Minimized sample loss and therefore increased the assay sensitivity |
| Reduced and optimized incubation time for ECD immobilization, ADC and ECD binding, and on-bead digestion steps | Minimized unintended changes, e.g. DAR profile, drug modification or decomposition, and therefore kept the ADC integrity |
| Decreased the analyte size from 150 kDa for intact ADC to 100 kDa for F(ab')2 and m/z from 2000-3200 to 1600-2800 | Increased LC-MS sensitivity |
| Decreased the analyte size from 150 kDa (intact ADCs) to 100 kDa [F(ab')2 fragments] | Increased LC-MS resolution for identification of complex ADC catabolites |

The affinity capture LC-MS F(ab')2 assay was extended to analysis of conventional ADCs, where drug is bound via inter-chain disulfides. Without IdeS protease digestion, after overnight deglycosylation by PNGase F, LC separation was needed to elute the Light Chain (25 kD) and Heavy Chain (50 kD) fragments since Light Chain fragments (smaller-size) suppress the ionization/MS signal of Heavy Chain fragments (larger-size). With IdeS protease digestion, the Light Chain and Heavy Chain are of similar size (about 23-29 kDa) and can be eluted and analyzed at the same time with minimal MS bias against the Heavy Chain. When utilizing a generic capturing reagent such as, biotinylated anti-human F(ab')2 antibody, the affinity capture LC-MS F(ab')2 assay allowed for parallel comparison in ADC biotransformations across ADCs with same drugs conjugated to different antibodies. This comparative example demonstrates the potential of the IdeS protease digestion, 2nd-generation assay to accommodate low-dose, labile, and complex site-specific ADCs, e.g., TDCs, for more accurate and detailed biotransformation and PK information. Such information helps to optimize cytoxic drug design, facilitate development of appropriate PK bioanalytical strategies, and inter-chain disulfides or site-specifically to the F(ab')2 or Fc region, the resultant antibody fragment that is free of drug, either the Fc/2 or F(ab')2 fragment peak, can be used to quantitate the protein concentration of the sample. This method is useful to characterize both traditional ADCs conjugated via inter-chain disulfides as well as THIO-MAB™ (Genentech, Inc.) antibody drug conjugates (TDC) that have two engineered cysteine residues per antibody located in either the Fab or the Fc region for site-specific conjugation. Antibody-drug conjugates are digested with IdeS and then injected on reversed-phase LC-MS with detection at an absorbance of 280 nm. In the case of TDCs conjugated on the Fab and traditional ADCs, the antibody fragments that contain drug are chromatographically separated from the Fc/2 fragment allowing for the Fc/2 fragment peak area to be used for protein concentration quantitation. This value is interpolated using the linear regression of a standard curve of antibody standards digested with IdeS where starting concentration is plotted against Fc/2 peak area (FIG. 11). In the case of TDCs conjugated via engineered cysteines on the Fc, the drug containing Fc/2 fragment is chromatographically separated from the F(ab')2 fragment allowing for the F(ab')2 fragment peak area to be used for protein concentration quantitation. This value is interpolated using the linear regression of a standard curve of antibody standards digested with IdeS where starting concentration is plotted against F(ab')2 peak area (FIG. 11).

Figure 13B:
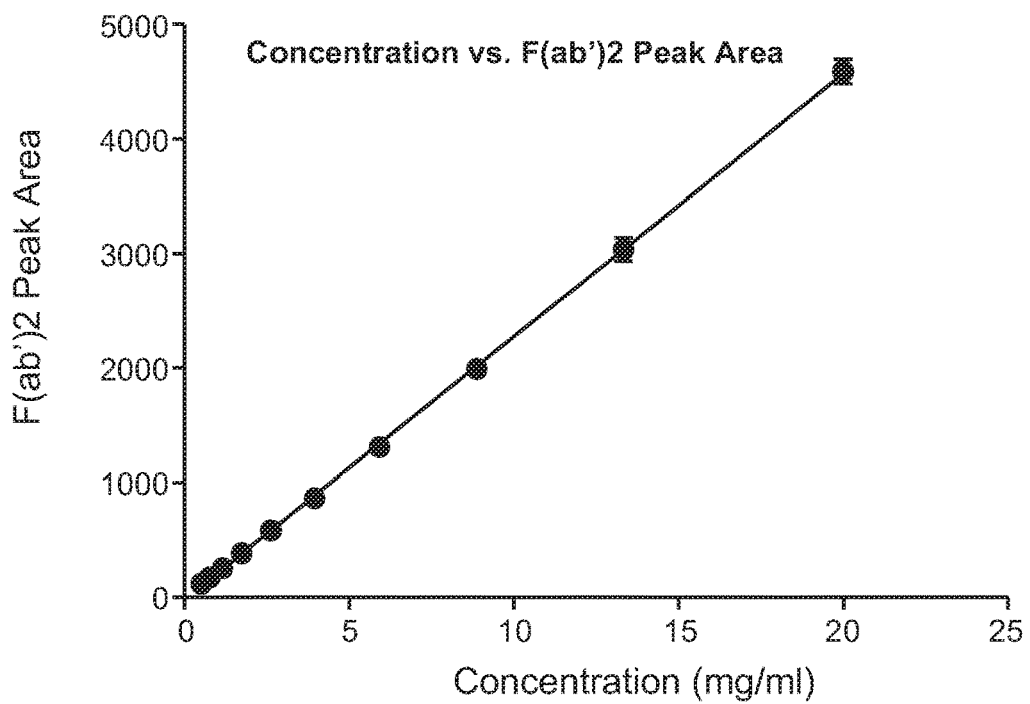
FIG. 13B shows a standard curve of (F(ab')2 peak area vs. concentration over a range of 0.5-20 mg/ml generated using Trastuzumab digested with IdeS protease. Protein concentration of TDCs site-specifically conjugated on the Fc can be determined using peak area of the F(ab')2 of the TDC (Bottom curve) and the linear regression.

Standard curves (Fc/2 peak areas vs. concentration; FIG. 13A) (F(ab')2 peak areas vs. concentration; FIG. 13B) over a range of 0.5-20 mg/ml were generated using trastuzumab digested with IdeS protease. Protein concentration of TDCs site-specifically conjugated on the F(ab) can be determined using peak area of the Fc/2 of the TDC (FIG. 13A) and the linear regression. Traditional ADCs conjugated on interchain disulfides can also be characterized using this method as the Fc/2 fragment is also without drug in these conjugates. Protein concentration of TDCs site-specifically conjugated on the Fc can be determined using peak area of the F(ab')2 of the TDC (FIG. 13B) and the linear regression.

Method

THIOMABs™ (Genentech, Inc.) with 2 engineered cysteine residues per antibody were incubated with a 3-fold molar excess of a thiol reactive linker-drug at pH 7.5 for 2 hours. Excess linker-drug was purified away by cation exchange and conjugates were formulated into a pH 5.5 buffer. The drug to antibody ratio (DAR) of the TDC was determined by LC-MS analysis using the abundance of the deconvoluted masses of drugged and un-drugged species (FIG. 12). All conjugates examined had a DAR of >1.7. Linker-drug payloads ranged from 700-1500 Da in size.

Thirty units (30 unit/μl) of IdeS (FABRICATOR™, Genovis AB) were added to 10 μl of antibody or antibody-drug conjugate that ranged in concentration from 0.52-20 mg/ml. The reaction mixtures were brought to a final volume of 50 μl with PBS with a final reaction pH of about pH 6.5. Samples where incubated at 37° C. for 1 hr before LC-MS analysis. Samples were analyzed on reversed phase high performance liquid chromatography (HPLC) using an HPLC system (Agilent 1260 infinity) coupled to an electrospray ionization time-of-flight mass spectrometer (Agilent 6224 TOF-LC). A volume of 10 μl of sample was injected on a PLRP-S 1000A°, 8 μm 50×2.1 mm column (Agilent) heated to 80° C. The gradient was generated using 0.05% trifluoroacetic acid (mobile phase A) and 0.05% trifluoroacetic acid in acetonitrile (mobile phase B) at a flow rate of 0.5 ml/min. The column was held at 5% B for 0.7 min, followed by a 4.3 min gradient from 30% B to 40% B. At 5 min, the concentration increased to 90% B where it was held for 1 min. The column was then re-equilibrated in 5% B for 2 min. Data was acquired and analyzed using Agilent MassHunter software.

Deconvoluted mass spectral data was used to confirm that all antibodies and antibody drug conjugates had been digested to completion and contained no intact antibody.

Figure 14:
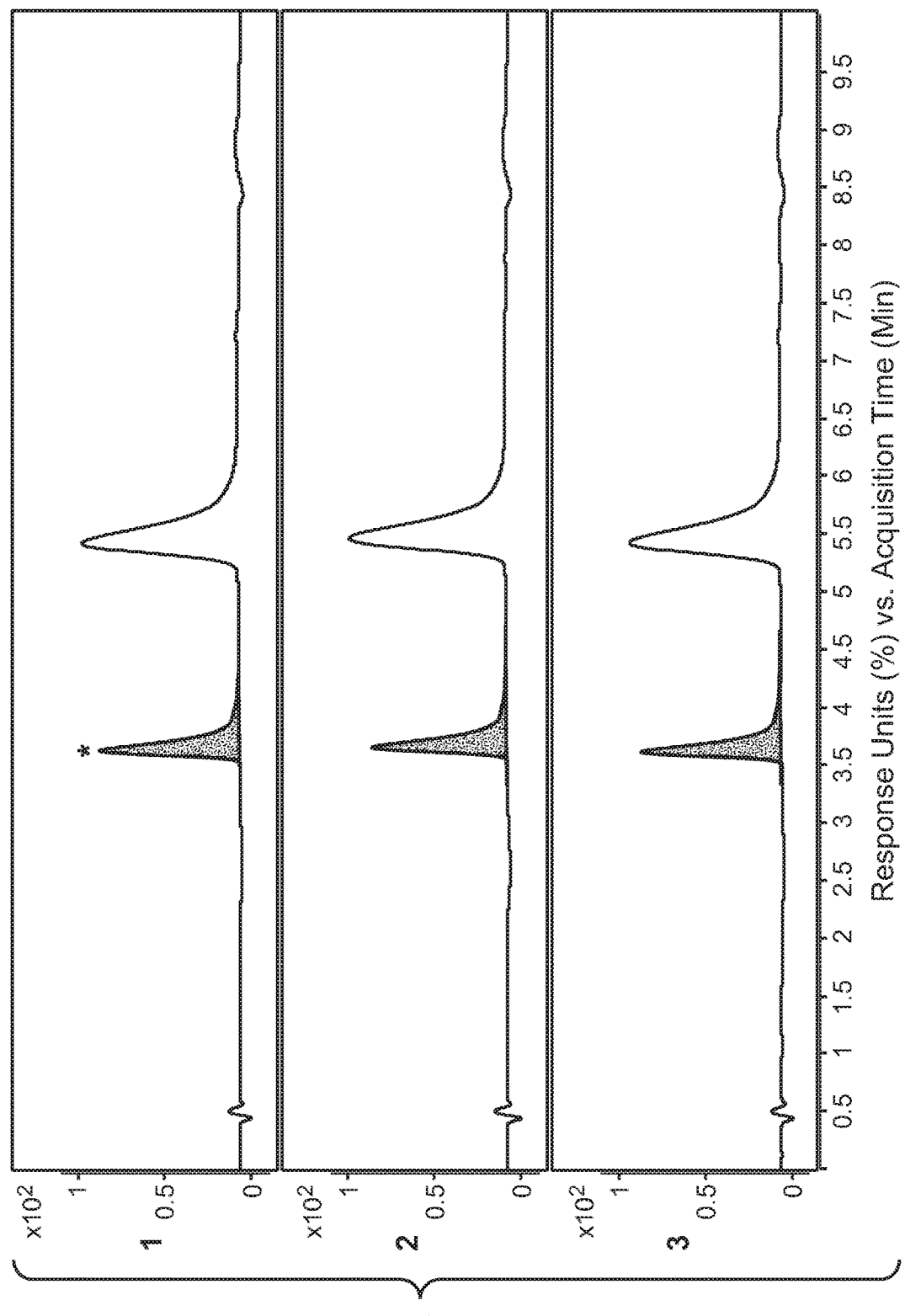
FIG. 14 shows a concentration determination of trastuzumab site-specifically conjugated at engineered cysteine K149C with linker-drug on the F(ab) at engineered cysteine K149C. The concentration was determined using Fc/2 peak areas (3 replicates) and linear regression from the standard curve.
Figure 15:
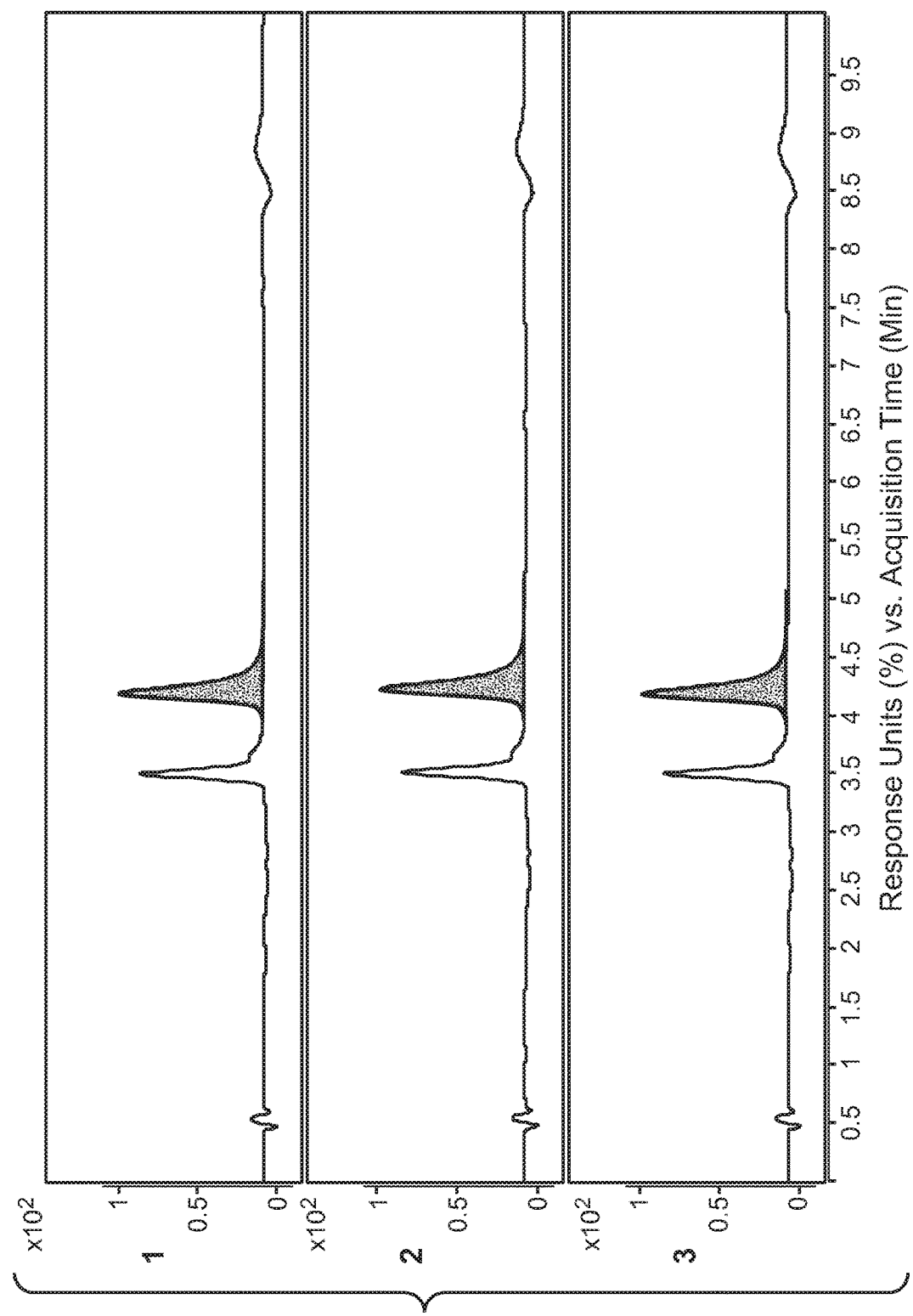
FIG. 15 shows a concentration determination of trastuzumab site-specifically conjugated at engineered cysteine S400C with linker-drug on the Fc at engineered cysteine S400C. The concentration was determined using F(ab')2 peak areas (3 replicates) and linear regression from the standard curve.
Figure 16:
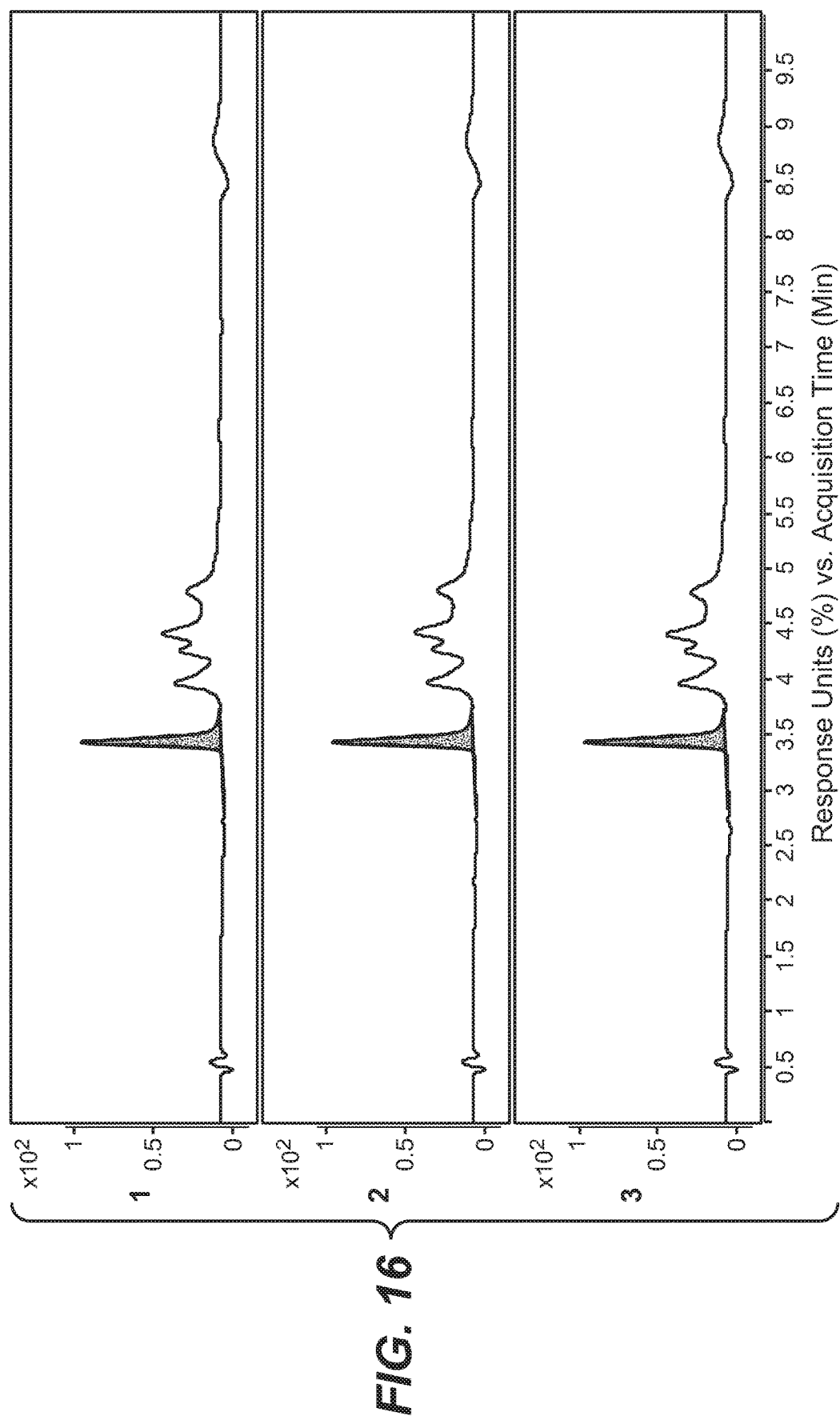
FIG. 16 shows a concentration determination of trastuzumab with linker-drug conjugated on inter-chain disulfides. The concentration was determined using Fc/2 peak areas (3 replicates) and linear regression from the standard curve. As the Fc/2 fragment contains no hinge disulfides, it contains no linker-drug.

Standard curves were developed using Trastuzumab (HERCEPTIN™; anti-Her2 human IgG1 antibody) digested with IdeS at known concentrations. Site-specific Trastuzumab constructs were prepared having:
1) linker-drug site-specifically conjugated on the F(ab) at engineered cysteine K149C (Conjugate A; FIG. 14);
2) linker-drug site-specifically conjugated on the Fc at engineered cysteine S400C (Conjugate B; FIG. 15); or,
3) linker-drug conjugated on inter-chain disulfides (Conjugate C; FIG. 16).

Trastuzumab was serially diluted by a factor of 1.5 from 20 mg/ml to 0.52 mg/ml in 20 mM histidine acetate pH 5.5 240 mM sucrose. This buffer was chosen for dilutions as it is the buffer used for final formulation of many ADCs and mimics the conditions of an experimental sample in the assay. Samples were diluted in triplicate to a total of ten concentrations.

A volume of 10 μl of each dilution was added to 39 μl of phosphate buffered saline pH 7.2, and 1 μl of IdeS (30 units/μl) to a total volume of 50 μl. The final pH of these samples was in the optimal activity range for IdeS activity. Samples where incubated at 37° C. for 1 hour. Samples were then run on LC-MS in order or increasing concentration. A volume of 10 μl of the antibody digests where injected onto a reversed phase column and gradient eluted to separate Fc/2 and F(ab')2 peaks. Samples that resulted in an injection of >5 μg of antibody where followed by blank runs of the same LC-MS method with no injection to ensure there was no sample carry-over to the next run.

Protein concentrations of antibody-drug conjugates were determined by proteolytic digestion with IdeS, and subsequent LC-MS analysis. A standard curve was developed using trastuzumab, digested with IdeS at known concentrations ranging from 0.52 mg/ml to 20 mg/ml (FIGS. 14-16). Standards were digested and run in triplicate with minimal error. Starting concentrations were plotted against peak areas resulting in a linear regression for the set of standards ($R^2$=0.9999) (FIG. 17). This linear regression equation was used to determine the protein concentration of unknown samples, according to the following tables:
1) for linker-drug site-specifically conjugated on the F(ab) (FIG. 14):

| Sample | Replicate | Fc/2 Peak Area | Concentration (mg/ml) | Average Concentration (mg/ml) | CV, % |
|---|---|---|---|---|---|
| Conjugate A | 1 | 1555.78 | 13.80 | 13.75 | 1.07 |
| | 2 | 1530.56 | 13.58 | | |
| | 3 | 1561.97 | 13.86 | | |

2) for linker-drug site-specifically conjugated on the Fc (FIG. 15)

| Sample | Replicate | F(ab')2 Peak Area | Concentration (mg/ml) | Average Concentration (mg/ml) | CV, % |
|---|---|---|---|---|---|
| Conjugate B | 1 | 719.98 | 3.23 | 3.22 | 0.39 |
| | 2 | 716.72 | 3.22 | | |
| | 3 | 714.16 | 3.21 | | |

3) for linker-drug conjugated on inter-chain disulfides (FIG. 16)

| Sample | Replicate | Fc/2 Peak Area | Concentration (mg/ml) | Average Concentration (mg/ml) | CV, % |
|---|---|---|---|---|---|
| Conjugate C | 1 | 428.21 | 3.81 | 3.83 | 0.79 |
| | 2 | 430.14 | 3.82 | | |
| | 3 | 434.91 | 3.87 | | |

The protein concentration of 81 TDCs was determined using this method as well as by the BCA, which is a widely accepted colorimetric assay for protein concentration determination. The concentration values determined by each method were plotted against each other showing a strong correlation, validating the accuracy and reproducibility of the IdeS digestion method (FIG. 17). The concentration values determined by this method can then be used to calculate the extinction coefficient of the TDC or ADC at an absorbance of A280 using the Beer-Lambert law.

FIG. 18A shows DAR profiling a TDC (PBD dimer drug, disulfide linker) standard mixture (DAR0:DAR2=1:1) by direct LC-MS assay, IdeS digestion, affinity capture LC-MS F(ab')2 assay, and PNGaseF, affinity capture LC-MS intact antibody assay with a standard deviation of 0.13, 0.09, and 0.14 for 3 replicates, respectively. Human plasma (100 μL) containing spiked TDC standard mixture was used for the affinity capture and 5 μL eluent was injected for LC-MS analysis.

FIG. 18B shows DAR (drug-antibody ratio) profiling of TDC standard mixtures (DAR0:DAR2=1:1) of TDC with PBD dimer (TDC1 and TDC4), anthracycline (TDC2) and CBI dimer (TDC5) drug moieties covalently attached to cysteine-engineered antibody with a disulfide linker by direct LC-MS, IdeS digestion affinity capture LC-MS F(ab')2 assay with IdeS digestion 1 hour, and affinity capture LC-MS F(ab')2 assay with PNGaseF digestion overnight (green). Human plasma (100 μL) containing spiked TDC standard mixture was used for the affinity capture and 5 μL elute was injected for LC-MS analysis. The error of measured DAR0:DAR2 for TDC2 was pronounced by the IdeS overnight digestion affinity capture LC-MS, indicating that prolonged on-bead incubation (e.g., overnight digestion) led to potential biased recoveries of different drug-loaded TDC2 species during sample preparation.

These methods provide a rapid, robust, and reproducible assay for protein concentration determination of ADCs regardless of the spectral properties of their conjugated payload.—Antibodies conjugated with other experimental payloads such as fluorophores can also be analyzed using this method to determine their protein concentration independent of the fluorophore or absorbance. Protein concentration of conventional ADCs may also be determined by this method, particularly for ADCs in which the payload is conjugated to inter-chain disulfides, as the Fc/2 region is devoid of these conjugation sites.

The assays of the invention include a relatively fast digestion step and continues to completion, without over-digestion. Thus, this methodology has significant advantages over the use of conventional proteases such as pepsin, papain, and endopeptidase Lysine C. For example, pepsin digestion of IgG1s is slow and occurs best below pH 5. Papain digestions are performed at neutral pH and the site of protein cleavage is not specific, and often leads to multiple protein cleavage events. Limited LysC digestion may over-digest the Fc region. IdeS has no risk of over-digestion as it cleaves IgG1 antibodies at one specific site on the heavy chain below the hinge region. In solution, IdeS is stable at 4° C. for up to one month. These characteristics contribute to the robust protein concentration assay demonstrated here.

For routine concentration measurements, the method can be conducted on HPLC without a mass spectrometer in-line. For example, a trastuzumab standard is digested and analyzed alongside test samples for quality control. Complete digestion can be confirmed in this assay as intact antibody has a known retention time and can be detected without mass spectral analysis. The peak area of the absorbance at 280 nm is then correlated directly with protein concentration, without the need for MS analysis.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method to detect and quantify antibody protein concentration and antibody-conjugated drug quantity in an antibody drug conjugate (ADC) comprising:
   a. digesting the ADC bound via the Fab region to a target antigen-paramagnetic bead capture media, where the ADC comprises at least one drug moiety linked to an antibody at a recombinantly-engineered site cysteine amino acid residue in the Fab region with IdeS protease that cleaves the ADC, to remove the Fc fragment and form a digested ADC composition comprising at least one peptide fragment that is not linked to the at least one drug moiety, and at least one peptide fragment that is linked to the at least one drug moiety, wherein the digesting comprises incubating the ADC with the IdeS protease for a time period of 1 hour; and,
   b. analyzing the digested ADC composition by a method comprising electrospray ionization liquid chromatography mass spectrometry.

2. The method of claim 1, wherein the antibody portion of the ADC is an antibody which binds to one or more tumor-associated antigens or cell-surface receptors selected from the group consisting of (1)-(53):
   (1) BMPR1B (bone morphogenetic protein receptor-type IB);
   (2) E16 (LAT1, SLC7A5);
   (3) STEAP1 (six transmembrane epithelial antigen of prostate);
   (4) MUC16 (0772P, CA125);
   (5) MPF (MPF, MSLN, SMR, megakaryocyte potentiating factor, mesothelin);
   (6) Napi2b (NAPI-3B, NPTIIb, SLC34A2, solute carrier family 34 (sodium phosphate), member 2, type II sodium-dependent phosphate transporter 3b);
   (7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
   (8) PSCA hlg (2700050C12Rik, C530008O16Rik, RIKEN cDNA 2700050C12, RIKEN cDNA 2700050C12 gene);
   (9) ETBR (Endothelin type B receptor);
   (10) MSG783 (RNF124, hypothetical protein FLJ20315);
   (11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
   (12) TrpM4 (BR22450, FLJ20041, TRPM4, TRPM4B, transient receptor potential cation channel, subfamily M, member 4);
   (13) CRIPTO (CR, CR1, CRGF, CRIPTO, TDGF1, teratocarcinoma-derived growth factor);
   (14) CD21 (CR2 (Complement receptor 2) or C3DR (C3d/Epstein Barr virus receptor) or Hs 73792);
   (15) CD79b (CD79B, CD79β, IGb (immunoglobulin-associated beta), B29);
   (16) FcRH2 (IFGP4, IRTA4, SPAP1A (SH2 domain containing phosphatase anchor protein 1a), SPAP1B, SPAP1C);
   (17) HER2;
   (18) NCA;
   (19) MDP;
   (20) IL20Rα;
   (21) Brevican;
   (22) EphB2R;
   (23) ASLG659;
   (24) PSCA;
   (25) GEDA;
   (26) BAFF-R (B cell-activating factor receptor, BLyS receptor 3, BR3);
   (27) CD22 (B-cell receptor CD22-B isoform);
   (28) CD79a (CD79A, CD79a, immunoglobulin-associated alpha);
   (29) CXCR5 (Burkitt's lymphoma receptor 1);
   (30) HLA-DOB (Beta subunit of MHC class II molecule (Ia antigen));
   (31) P2X5 (Purinergic receptor P2X ligand-gated ion channel 5);
   (32) CD72 (B-cell differentiation antigen CD72, Lyb-2);
   (33) LY64 (Lymphocyte antigen 64 (RP105), type I membrane protein of the leucine rich repeat (LRR) family);
   (34) FcRH1 (Fc receptor-like protein 1);
   (35) FcRH5 (IRTA2, Immunoglobulin superfamily receptor translocation associated 2);
   (36) TENB2 (putative transmembrane proteoglycan);
   (37) PMEL17 (silver homolog; SILV; D12S53E; PMEL17; SI; SIL);
   (38) TMEFF1 (transmembrane protein with EGF-like and two follistatin-like domains 1; Tomoregulin-1);
   (39) GDNF-Ra1 (GDNF family receptor alpha 1; GFRA1; GDNFR; GDNFRA; RETL1; TRNR1; RET1L; GDNFR-alpha1; GFR-ALPHA-1);
   (40) Ly6E (lymphocyte antigen 6 complex, locus E; Ly67, RIG-E, SCA-2,TSA-1);
   (41) TMEM46 (shisa homolog 2 (*Xenopus laevis*); SHISA2);
   (42) Ly6G6D (lymphocyte antigen 6 complex, locus G6D; Ly6-D, MEGT1);
   (43) LGR5 (leucine-rich repeat-containing G protein-coupled receptor 5; GPR49, GPR67);
   (44) RET (ret proto-oncogene; MEN2A; HSCR1; MEN2B; MTC1; PTC; CDHF12; Hs.168114; RET51; RET-ELE1);
   (45) LY6K (lymphocyte antigen 6 complex, locus K; LY6K; HSJ001348; FLJ35226);
   (46) GPR19 (G protein-coupled receptor 19; Mm.4787);
   (47) GPR54 (KISS1 receptor; KISS1R; GPR54; HOT7T175; AXOR12);
   (48) ASPHD1 (aspartate beta-hydroxylase domain containing 1; LOC253982);
   (49) Tyrosinase (TYR; OCAIA; OCA1A; tyrosinase; SHEP3);
   (50) TMEM118 (ring finger protein, transmembrane 2; RNFT2; FLJ14627);
   (51) GPR172A (G protein-coupled receptor 172A; GPCR41; FLJ11856; D15Ertd747e);
   (52) CD33; and
   (53) CLL-1.

3. The method of claim 1, wherein the drug moiety is linked to the antibody portion of the ADC through a linker and is selected from the group consisting of a peptide, a polyamide, a maytansinoid, dolastatin, auristatin, calicheamicin, pyrrolobenzodiazepine (PBD), PNU-159682, anthracyclines, duocarmycins, vinca alkaloids, taxanes, trichothecene, CC1065, duocarmycin, camptothecin, and elinafide.

4. The method of claim 1, wherein the digesting comprises incubating the ADC with the IdeS protease at a temperature between 20° C. and 45° C.; and at a pH between pH 5 and pH 9.

5. The method of claim 1, wherein the digesting comprises incubating the ADC with the IdeS protease at a pH of 7, and at a temperature of 37° C.

6. The method of claim 1, further comprising washing ADC bound to the target antigen-paramagnetic bead capture media to remove non-antibody proteins in contact with the ADC.

7. The method of claim 1, further comprising dephosphorylating ADC bound to the target antigen-paramagnetic bead capture media.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial sequence
<220> FEATURE:
<223> OTHER INFORMATION: sequence is synthesized

<400> SEQUENCE: 1

His Thr Cys Pro Pro Cys Pro Ala Pro Glu Leu Leu Gly Gly Pro
1               5                   10                  15

Ser Val Phe

<210> SEQ ID NO 2
<211> LENGTH: 17
<212> TYPE: PRT
<213> ORGANISM: Artificial sequence
<220> FEATURE:
<223> OTHER INFORMATION: sequence is synthesized

<400> SEQUENCE: 2

His Thr Cys Pro Pro Cys Pro Ala Pro Pro Val Ala Gly Pro Ser
1               5                   10                  15

Val Phe
```